United States Patent
Zhou et al.

(10) Patent No.: US 11,518,747 B2
(45) Date of Patent: *Dec. 6, 2022

(54) SOLID FORMS OF AN N-TERMINAL DOMAIN ANDROGEN RECEPTOR INHIBITOR AND USES THEREOF

(71) Applicant: ESSA Pharma, Inc., Vancouver (CA)

(72) Inventors: Han-Jie Zhou, Foster City, CA (US); Peter Virsik, Portola Valley, CA (US)

(73) Assignee: ESSA Pharma, Inc., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/732,081

(22) Filed: Apr. 28, 2022

(65) Prior Publication Data

US 2022/0259158 A1    Aug. 18, 2022

Related U.S. Application Data

(63) Continuation of application No. 17/526,660, filed on Nov. 15, 2021, now Pat. No. 11,358,938, which is a continuation of application No. 17/342,923, filed on Jun. 9, 2021, now Pat. No. 11,242,324, which is a continuation of application No. 17/233,161, filed on Apr. 16, 2021.

(60) Provisional application No. 63/011,671, filed on Apr. 17, 2020.

(51) Int. Cl.
| | |
|---|---|
| *A61K 31/505* | (2006.01) |
| *A61K 31/4164* | (2006.01) |
| *C07D 239/69* | (2006.01) |
| *C07D 239/42* | (2006.01) |
| *A61K 45/06* | (2006.01) |

(52) U.S. Cl.
CPC ............ *C07D 239/69* (2013.01); *A61K 45/06* (2013.01); *C07D 239/42* (2013.01); *C07B 2200/13* (2013.01)

(58) Field of Classification Search
CPC .......................... A61K 31/505; A61K 31/4164
USPC .................................................. 514/275, 398
See application file for complete search history.

(56) References Cited

U.S. PATENT DOCUMENTS

| | | | |
|---|---|---|---|
| 2,571,217 A | 10/1951 | Davis et al. | |
| 2,890,189 A | 6/1959 | Greenlee | |
| 3,074,974 A | 1/1963 | Gebura | |
| 3,162,615 A | 12/1964 | Bremmer | |
| 4,284,574 A | 8/1981 | Bagga | |
| 4,369,298 A | 1/1983 | Kida et al. | |
| 4,855,184 A | 8/1989 | Klun et al. | |
| 4,904,760 A | 2/1990 | Gaku et al. | |
| 5,043,375 A | 8/1991 | Henning et al. | |
| 5,155,196 A | 10/1992 | Kolb et al. | |
| 5,362,615 A | 11/1994 | Hagemann et al. | |
| 5,403,697 A | 4/1995 | Doessel et al. | |
| 5,753,730 A | 5/1998 | Nagata et al. | |
| 5,807,899 A | 9/1998 | Rolf et al. | |
| 5,998,674 A | 12/1999 | Taketani et al. | |
| 6,218,430 B1 | 4/2001 | Allegretto et al. | |
| 6,245,117 B1 | 6/2001 | Nishikawa et al. | |
| 7,183,323 B2 | 2/2007 | Chinn et al. | |
| 7,273,867 B2 | 9/2007 | Dorsch et al. | |
| 7,595,345 B2 | 9/2009 | Bunel et al. | |
| 7,666,868 B2 | 2/2010 | Maier et al. | |
| 7,674,795 B2 | 3/2010 | Mailliet et al. | |
| 8,048,888 B2 | 11/2011 | Wosikowski-Buters et al. | |
| 8,445,507 B2 | 5/2013 | Jung | |
| 8,455,477 B2 | 6/2013 | Katz | |
| 8,686,050 B2 | 4/2014 | Sadar et al. | |
| 9,173,939 B2 | 11/2015 | Andersen et al. | |
| 9,365,510 B2 | 6/2016 | Andersen et al. | |
| 9,375,496 B2 | 6/2016 | Andersen et al. | |
| 9,388,112 B2 | 7/2016 | Sadar et al. | |
| 9,862,667 B2 | 1/2018 | Sadar et al. | |
| 10,654,811 B2 | 5/2020 | Andersen et al. | |
| 11,059,795 B2 | 7/2021 | Zhou et al. | |
| 11,242,324 B2 | 2/2022 | Zhou et al. | |
| 11,345,670 B2 | 5/2022 | Andersen et al. | |
| 11,358,938 B2 * | 6/2022 | Zhou ..................... C07D 239/69 |
| 2003/0092724 A1 | 5/2003 | Kao et al. | |
| 2003/0105268 A1 | 6/2003 | Boriack et al. | |
| 2004/0049004 A1 | 3/2004 | Boriack et al. | |
| 2004/0243316 A1 | 12/2004 | Weinmann et al. | |
| 2008/0153837 A1 | 6/2008 | Mailliet et al. | |

(Continued)

FOREIGN PATENT DOCUMENTS

| | | |
|---|---|---|
| CA | 2206422 A1 | 6/1996 |
| CA | 2226469 A1 | 1/1997 |

(Continued)

OTHER PUBLICATIONS

Alabi, A. et al., "Quick and simple sample treatment for multiresidue analysis of bisphenols, bisphenol diglycidyl ethers and their derivatives in canned food prior to liquid chromatography and fluorescence detection," J. of Chromatography A, 2014, 1336, 23-33.
Alvarez, C. et al., "Conformational and Experimental Studies on the Dipole Moments of Models of Comblike Polymers", Macromolecules, 30(20): 6369-6375 (1997).
Anderson, R. et al., "Regression of Castrate-Recurrent Prostate Cancer by a Small-Molecule Inhibitor of the Amino-Terminus Domain of the Androgen Receptor", Cancer Cell, 17:535-546 (2010).
Anton, R. et al., Opinion of the scientific panel on food additives, flavourings, processing aids and materials in contact with food (AFC) on a request from the commission related to 2,2-bis(4-hydroxyphenyl)propane bis(2,3-epoxypropyl)ether (bisphenol A diglycidyl ether, BADGE), Ref. No. 13510 and 39700 (EFSA-Q-2003-178), The EFSA Journal, 86:1-40 (2004).

(Continued)

*Primary Examiner* — Raymond J Henley, III
(74) *Attorney, Agent, or Firm* — Cooley LLP

(57) ABSTRACT

The present invention relates to a crystalline form of Compound I, a salt, a solvate, or a solvate salt thereof or an amorphous form of Compound I, a salt, a solvate, or a solvate salt thereof. The present invention also provides compositions comprising the crystalline form and/or the amorphous form, therapeutic uses of the crystalline forms and/or the amorphous forms, and the compositions thereof.

30 Claims, 16 Drawing Sheets

(56) References Cited

U.S. PATENT DOCUMENTS

| | | |
|---|---|---|
| 2008/0193380 A1 | 8/2008 | Dalton et al. |
| 2008/0255395 A1 | 10/2008 | Dai et al. |
| 2009/0105349 A1 | 4/2009 | Barvian et al. |
| 2009/0246158 A1 | 10/2009 | Rudolph et al. |
| 2011/0230556 A1 | 9/2011 | Sadar et al. |
| 2013/0045204 A1 | 2/2013 | Sadar et al. |
| 2013/0109758 A1 | 5/2013 | Sadar et al. |
| 2013/0131167 A1 | 5/2013 | Sadar et al. |
| 2013/0245129 A1 | 9/2013 | Sadar et al. |
| 2013/0336962 A1 | 12/2013 | Andersen et al. |
| 2014/0248263 A1 | 9/2014 | Andersen et al. |
| 2014/0335080 A1 | 11/2014 | Andersen et al. |
| 2015/0010469 A1 | 1/2015 | Andersen et al. |
| 2015/0125389 A1 | 5/2015 | Andersen et al. |
| 2015/0210681 A1 | 7/2015 | Bourque et al. |
| 2016/0068466 A1 | 3/2016 | Andersen et al. |
| 2016/0367707 A1 | 12/2016 | Andersen et al. |
| 2017/0056336 A1 | 3/2017 | Sadar et al. |
| 2017/0121261 A1 | 5/2017 | Sadar et al. |
| 2017/0298033 A1 | 10/2017 | Andersen et al. |
| 2017/0368036 A1 | 12/2017 | Hattersley et al. |
| 2018/0064657 A1 | 3/2018 | Andersen et al. |
| 2018/0235925 A1 | 8/2018 | Andersen et al. |
| 2018/0327368 A1 | 11/2018 | Andersen et al. |
| 2019/0022093 A1 | 1/2019 | Wipf et al. |
| 2020/0123117 A1 | 4/2020 | Zhou et al. |
| 2020/0247763 A1 | 8/2020 | Zhou et al. |
| 2020/0281949 A1 | 9/2020 | Warner et al. |
| 2020/0325106 A1 | 10/2020 | Andersen et al. |
| 2021/0198213 A1 | 7/2021 | Zhou et al. |
| 2021/0323931 A1 | 10/2021 | Zhou et al. |
| 2021/0332016 A1 | 10/2021 | Zhou et al. |
| 2021/0387957 A1 | 12/2021 | Andersen et al. |
| 2022/0073472 A1 | 3/2022 | Zhou et al. |
| 2022/0105093 A1 | 4/2022 | Virsik et al. |
| 2022/0202780 A1 | 6/2022 | Virsik et al. |

FOREIGN PATENT DOCUMENTS

| | | |
|---|---|---|
| CA | 2339775 A1 | 3/2000 |
| CA | 2606262 A1 | 11/2006 |
| CA | 2728219 A1 | 1/2010 |
| CA | 2786319 A1 | 7/2011 |
| CN | 102083780 A | 6/2011 |
| CN | 103342892 A | 10/2013 |
| EP | 0056175 A1 | 7/1982 |
| EP | 0155238 A2 | 9/1985 |
| EP | 0293768 A1 | 12/1988 |
| EP | 0515128 A1 | 11/1992 |
| FR | 1389005 | 2/1965 |
| JP | B-S45-008432 | 3/1970 |
| JP | S56-5472 A | 1/1981 |
| JP | 63-196675 | 8/1988 |
| JP | 63-317539 A | 12/1988 |
| JP | H01-503541 | 11/1989 |
| JP | H02-4815 | 1/1990 |
| JP | 6-049473 A2 | 2/1994 |
| JP | 7-117349 A | 5/1995 |
| JP | 09-176240 A | 7/1997 |
| JP | H10133427 A | 5/1998 |
| JP | A-H10-316803 | 12/1998 |
| JP | 11-166087 A2 | 6/1999 |
| JP | 2000-072705 A2 | 3/2000 |
| JP | 2001-511170 A | 8/2001 |
| JP | 2005-325301 A | 11/2005 |
| JP | 2006-208607 A | 8/2006 |
| JP | 2006-265351 A2 | 10/2006 |
| JP | 2007-513089 A | 5/2007 |
| JP | 2007-290980 | 11/2007 |
| KR | 10-2011-0044216 A | 4/2011 |
| PL | 141793 B1 | 8/1987 |
| RU | 2454394 C2 | 6/2012 |
| SU | 638596 | 12/1978 |
| SU | 929630 | 5/1982 |
| WO | WO 1988/009782 A1 | 12/1988 |
| WO | WO 1996/16646 A1 | 6/1996 |
| WO | WO 1998/034930 A1 | 8/1998 |
| WO | WO 2000/001813 A2 | 1/2000 |
| WO | WO 2000/010958 A1 | 3/2000 |
| WO | WO 2001/088013 A2 | 11/2001 |
| WO | WO 2002/005813 A2 | 1/2002 |
| WO | WO 2003/004481 A1 | 1/2003 |
| WO | WO 2005/042464 A1 | 5/2005 |
| WO | WO 2005/077967 A1 | 8/2005 |
| WO | WO 2007/079078 A1 | 7/2007 |
| WO | WO 2008/101806 A2 | 8/2008 |
| WO | WO 2010/000066 A1 | 1/2010 |
| WO | WO 2011/082487 A1 | 7/2011 |
| WO | WO 2011/082488 A1 | 7/2011 |
| WO | WO 2012/139039 A2 | 10/2012 |
| WO | WO 2012/145328 A1 | 10/2012 |
| WO | WO 2012/145330 A1 | 10/2012 |
| WO | WO 2013/028572 A1 | 2/2013 |
| WO | WO 2013/028791 A1 | 2/2013 |
| WO | WO 2014/011220 A2 | 1/2014 |
| WO | WO 2014/179865 A1 | 11/2014 |
| WO | WO 2015/031984 A1 | 3/2015 |
| WO | WO 2016/058080 A1 | 4/2016 |
| WO | WO 2016/058082 A1 | 4/2016 |
| WO | WO 2016/112455 A1 | 7/2016 |
| WO | WO 2016/141458 A1 | 9/2016 |
| WO | WO 2017/177307 A1 | 10/2017 |
| WO | WO 2017/210771 A1 | 12/2017 |
| WO | WO 2018/045450 A1 | 3/2018 |
| WO | WO 2018/157232 A1 | 9/2018 |
| WO | WO 2019/226991 A1 | 11/2019 |
| WO | WO 2020/081999 A1 | 4/2020 |
| WO | WO 2020/198710 A1 | 10/2020 |
| WO | WO 2020/198711 A1 | 10/2020 |
| WO | WO 2020/198712 A1 | 10/2020 |

OTHER PUBLICATIONS

Antonarakis et al., "Androgen receptor variant-driven prostate cancer: clinical implications and therapeutic targeting," Prostate Cancer and Prostatic Diseases (2016), 1-11.

Antonarakis et al., "Targeting the N-Terminal Domain of the Androgen Receptor: A New Approach for the Treatment of Advanced Prostate Cancer," The Oncologist 2016;21:1-9.

Auzou et al., European Journal of Medicinal Chemistry, 9(5):548-554 (1974) (with English Abstract).

Balbay, M.D. et al., "Highly Metastatic Human Prostate Cancer Growing within the Prostate of Athymic Mice Overexpresses Vascular Endothelial Growth Factor", Clinical Cancer Research, 5:783-789 (1999).

Banker (ed.) et al., Modern Pharmaceutics, Third Edition, Revised and Expanded, Marcel Dekker, Inc., 1997, pp. 451 and 596.

Banuelos et al., "Sintokamide A is a novel antagonist of androgen receptor that uniquely binds activation function-1 in its amino-terminal domain," The Journal of Biological Chemistry, vol. 291, No. 42, pp. 22231-22243, Oct. 14, 2016.

Bao, B. et al., "Androgen signaling is required for the vitamin D-mediated growth inhibition in human prostate cancer cells", Oncogene, 23:3350-3360 (2004).

Berge, S.M. et al., "Pharmaceutical Salts", Pharmaceutical Sciences, 66(1):1-19 (1977).

Berger, U. et al., "Identification of Derivatives of Bisphenol A Diglycidyl Ether and Novolac Glycidyl Ether in Can Coatings by Liquid Chromatography/Ion Trap Mass Spectrometry," Journal of AOAC International, Food Chemical Contaminants, 83(6): 1367-1376 (2000).

Biles, J.E. et al., "Determination of the Diglycidyl Ether of Bisphenol A and its Derivatives in Canned Foods", J. Agric. Food Chem., 47:1965-1969 (1999).

Bisson, W.H. et al., "Discovery of antiandrogen activity of nonsteroidal scaffolds of marketed drugs", PNAS, 104(29):11927-11932 (2007).

Blaszczyk, N. et al., "Osteoblast-Derived factors Induce Androgen-Independent Proliferation and Expression of Prostate-Specific Antigen in Human Prostate Cancer Cells", Clin. Cancer Res., 10:1860-1869 (2004).

(56) References Cited

OTHER PUBLICATIONS

Bodei, et al., "Radionuclide Therapy with Iodine-125 and Other Auger-Electron-Emitting Radionuclides: Experimental Models and Clinical Applications." Cancer Biother. & Radiopharm. (2003); 18(6): 861-877.
Bohler, Paul et al., "Identification of Migrants from Coatings of Food Cans and Tubes: Reaction Products of Bisphenol-A-Diglycidyl Ether (BADGE) with Phenols and Solvents", Mitt. Gebiete Lebensm. Hyg., 89:529-547 (1998).
Brand et al., "EPI-001 is a selective peroxisome proliferator-activated receptor-gamma modulator with inhibitory effects on androgen receptor expression and activity in prostate cancer." Oncotarget (2015); 6(6): 3811-3824.
Brzozowski, Z. et al., "Precursors for bisphenolic resins", CAPLUS Database Accession No. 1990:36690, Document No. 112:33690, (1987), 1 page (Abstract).
Bruckheimer, E.M. et al., "Apoptosis in prostate carcinogenesis A growth regulator and a therapeutic target", Cell Tissue Res, 301:153-162 (2000).
Cascini, et al., "$^{124}$Iodine: A Longer-Life Positron Emitter Isotope—New Opportunities in Molecular Imaging." Hindawi Publishing Corp.Biomed. Res. Int. (2014); vol. 2014, Article ID 672094, 7 pages.
Chang, C. et al., "Development of Peptide Antagonists for the Androgen Receptor Using Combinatorial Peptide Phage Display", Molecular Endocrinology, 19(10):2478-2490 (2005).
Choi, K. M. et al., "New Families of Photocurable Oligomeric Fluoromonomers for Use in Dental Composites", Chemistry of Materials, 8(12):2704-2707 (1996).
Clinton, G.M. et al., "Estrogen action in human ovarian cancer", Critical Reviews in Oncology/Hematology, 25:1-9 (1997).
Crivello, J. V. et al., "Synthesis and photopolymerization of multi-functional propenyl ether monomers," Database CAPLUS [online], Chemical Abstracts Service, Columbus, Ohio, US, XP002729292, retrieved from STN CA Caesar Accession No. 1994-606067 (1994), 3 pages.
Crivello, J. V. et al., "Synthesis and photopolymerization of multi-functional propenyl ether monomers", Journal of Macromolecular Science, Pure and Applied Chemistry, A31(9):1105-1119 (1994).
Cook, W. D., "Fracture and Structure of Highly Crosslinked Polymer Composites", Journal of Applied Polymer Science, 42:1259-1269 (1991).
Culig, Zoran et al., "Androgen Receptor Activation in Prostatic Tumor Cell Lines by Insulin-like Growth Factor-I, Keratinocyte Growth Factor, and Epidermal Growth Factor", Cancer Research, 54:5474-5478 (1994).
Danquah, M. et al., "Micellar Delivery of Bicalutamide and Embelin for Treating Prostate Cancer", Pharmaceutical Research, 26:2081-2092 (2009).
Das, Debasish et al., "Sulfonic acid functionalized mesoporous MCM-41 silica as a convenient catalyst for Bisphenol-A synthesis", Chemical Communications, pp. 2178-2179 (2001).
De Mol et al., "EPI-001, a compound active against castration-resistant prostate cancer, targets transactivation unit 5 of the androgen receptor," ACS Chem. Biol., 2016, 11, 9, 2499-2505.
De Santis, M et al., "Practical Guidance on the Role of Corticosteroids in the Treatment of Metastatic Castration-resistant Prostate Cancer," Urology, 2016, vol. 96, pp. 156-164.
Dehm, S. et al., "Ligand-independent Androgen Receptor Activity is Activation Function-2-independent and Resistant to Antiandrogens in Androgen Refractory Prostate Cancer Cells", The Journal of Biological Chemistry, 281 (38):27882-27893 (2006).
Dehm, S. et al., "Splicing of a Novel Androgen Receptor Exon Generates a Constitutively Active Androgen Receptor that Mediates Prostate Cancer Therapy Resistance", Cancer Research, 68:5469-5477 (2008).
Edmondson, R.J., et al., "The human ovarian surface epithelium is an androgen responsive tissue", British Journal of Cancer, 86:879-885 (2002).

Estebanez-Perpiñá, E. et al., "A surface on the androgen receptor that allosterically regulates coactivator binding," PNAS, 104(41):16074-16079 (2007).
Estebanez-Perpiñá, E. et al., "The Molecular Mechanisms of Coactivator Utilization in Ligand-dependent Transactivation by the Androgen Receptor," The Journal of Biological Chemistry, 280(9):8060-8068 (2005).
Fehlberg S. et al., "Bisphenol A diglycidyl ether induces apoptosis in tumor cells independently of peroxisome proliferator-activated receptor-.gamma., in caspase-dependent and -independent manners," Biochem. J., 362:573-578 (2002).
Gallart-Ayala, H. et al., "The analysis of bisphenol A-diglycidyl ether (BADGE), bisphenol F-diglycidyl ether (BFDGE) and their derivatives in canned food and beverages by LC-MS/MS", Thermo Fisher Scientific Inc., 4 pages (2011).
Garuti, L., et al., "Irreversible Protein Kinase Inhibitors", Current Medicinal Chemistry, 18:2981-2994 (2011).
Garcia et al., "Determination of compounds from epoxy resins in food simulants by HPLC-fluorescence." Chromatographia, 58(5-6): 337-342 (2003).
Gleave, Martin et al., "Acceleration of Human Prostate Cancer Growth in Vivo by Factors Produced by Prostate and Bone Fibroblasts", Cancer Research, 51:3753-3761 (1991).
Gregory, Christopher et al., "Epidermal Growth Factor Increases Coactivation of the Androgen Receptor in Recurrent Prostate Cancer", The Journal of Biological Chemistry, 279(8):7119-7130 (2004).
Guinan, P.D. et al., "Impotence Therapy and Cancer of the Prostate", The American Journal of Surgery, 131:599-600 (1976).
Guo, Zhiyong et al., "A Novel Androgen Receptor Splice Variant Is Up-regulated during Prostate Cancer Progression and Promotes Androgen Depletion—Resistant Growth", Cancer Research, 69:2305-13 (2009).
Haggstrom, Stina et al., "Testosterone Induces Vascular Endothelial Growth Factor Synthesis in the Ventral Prostate in Castrated Rats", The Journal of Urology, 161:1620-1625 (1999).
Harper et al., "Expression of Androgen Receptor and Growth Factors in Premalignant Lesions of the Prostate", Journal of Pathology, 186:169-177 (1998).
He, B. et al., "Activation Function 2 in the Human Androgen Receptor Ligand Binding Domain Mediates Interdomain Communication with the $NH_2$-terminal Domain", The Journal of Biological Chemistry, 274(52):37219-37225 (1999).
He, B. et al., "Structural Basis for Androgen Receptor Interdomain and Coactivator Interactions Suggests a Transition in Nuclear Receptor Activation Function Dominance", Molecular Cell, 16:425-438 (2004).
Henke, H., "Selektive praparative gelchromatographische Trennung niedermolekularer Verbindungen an Sephadex LH-20", Journal of Chromatography, 254: 296-308 (1983).
Heinlein, Cynthia A., et al., "Androgen Receptor in Prostate Cancer", Endocrine Reviews, 25(2):276-308 (2004).
Helzlsouer, Kathy J., et al., "Serum Gonadotropins and Steroid Hormones and the Development of Ovarian Cancer", JAMA, 274(24):1926-1930 (1995).
Horoszewicz, J.S. et al., "LNCaP Model of Human Prostatic Carcinoma", Cancer Research, 43:1809-1818 (1983).
Hu, R. et al., "Ligand-Independent Androgen Receptor Variants Derived from Splicing of Cryptic Exons Signify Hormone-Refractory Prostate Cancer", Cancer Research, 69:16-22 (2009).
Huber, P.R. et al., "Prostate Specific Antigen. Experimental and Clinical Observations", Scand. J. Urol Nephrol., 104:33-39 (1987).
Hur, E. et al., "Recognition and Accommodation at the Androgen Receptor Coactivator Binding Interface", PLoS Biology, 2(9)(e274):1303-1312 (2004).
Imamura et al., "An imaging agent to detect androgen receptor and its active splice variants in prostate cancer," JCI Insight. 2016;1(11):e87850 15 pages.
Imamura et al., "Androgen receptor targeted therapies in castration-resistant prostate cancer: Bench to clinic," International Journal of Urology (2016), 23(8):654-65.

(56) References Cited

OTHER PUBLICATIONS

Isaacs, J.T., et al., "New Biochemical Methods to Determine Androgen Sensitivity of Prostatic Cancer: The Relative Enzymatic Index (REI)", Prostate Cancer and Hormone Receptors, pp. 133-144 (1979).
Isaacs, J.T., "Antagonistic Effect of Androgen on Prostatic Cell Death", The Prostate, 5:545-557 (1984).
Jackson, J. A. et al., "Prostatic Complications of Testosterone Replacement Therapy", Arch Intern Med., 149:2365-2366 (1989).
Japanese Patent Application No. 2016-512175, Notice of Reasons for Rejection dated Jun. 21, 2016 (and English translation), 12 pages.
Jenster, G. et al., "Domains of the Human Androgen Receptor Involved in Steroid Binding, Transcriptional Activation, and Subcellular Localization", Molecular Endocrinology, 5:1396-1404 (1991).
Jenster, G., et al. "Identification of two transcription activation units in the N-terminal domain of the human androgen receptor." Journal of Biological Chemistry (1995); 270. 13: 7341-7346.
Jia, L. et al., "Androgen Receptor Signaling: Mechanism of Interleukin-6 Inhibition", Cancer Research, 64:2619-2626 (2004).
Jia, L. et al., "Androgen Receptor-Dependent PSA Expression in Androgen-Independent Prostate Cancer Cells Does Not Involve Androgen Receptor Occupancy of the PSA Locus", Cancer Research, 65:8003-8008 (2005).
Kaighn, M.E. et al., "Prostate Carcinoma: Tissue Culture Cell Lines", National Cancer Institute Monograph No. 49, pp. 17-21 (1978).
Kato, M. et al., "Cotargeting androgen receptor splice variants and mTOR signaling pathway for the treatment of castration-resistant prostate cancer," Clin Cancer Res, Jun. 2016, vol. 22, pp. 2744-2754.
Kemppainen, J. A. et al., "Distinguishing Androgen Receptor Agonists and Antagonists: Distinct Mechanisms of Activation by Medroxyprogesterone Acetate and Dihydrotestosterone", Mol. Endocrinol., 13:440-454 (1999).
Kim, D. et al., "Androgen Receptor Expression and Cellular Proliferation During Transition from Androgen-Dependent to Recurrent Growth after Castration in the CWR22 Prostate Cancer Xenograft", American Journal of Pathology, 160(1):219-226 (2002).
Kolbel, M. et al., "Design of Liguid Crystalline Block Molecules with Nonconventional Mesophase Morphologies: Calamitic Bolaamphiphiles with Lateral Alkyl Chains", J. Am. Chem. Soc., 123:6809-6818 (2001).
Kumar, S. et al., "Synthesis of new crown analogs derived from bisphenol," Indian Journal Chemistry, 36B:656-661 (1997).
L'Heureux, A. et al., "Aminodifluorosulfinium Salts: Selective Fluorination Reagents with Enhanced Thermal Stability and Ease of Handling", J. Org. Chem, 75:3401-3411 (2010).
Langley, E. et al., "Evidence for an Anti-parallel Orientation of the Ligand-activated Human Androgen Receptor Dimer", The Journal of Biological Chemistry, 270(50):29983-29990 (1995).
Lannoye, G.S. et al., "N-Fluoroalkylated and N-alkylated analogs of the dopaminergic D-2 receptor antagonist raclopride", J. Med. Chem., 33(9):2430-2437 (1990).
Leepipatpiboon, N. et al., "Simultaneous determination of bisphenol-A-diglycidyl ether, bisphenol-F-diglycidyl ether, and their derivatives in oil-in-water and agueous-based canned foods by high-performance liguid chromatography with fluorescence detection." Journal of Chromatography A (2005); 1073.1: 331-339.
Levoin et al., "Determination of the binding mode and interacting amino-acids for dibasic H3 receptor antagonists", Bioorganic & Medicinal Chemistry, 21 (2013) 4526-4529 and LEVOIN et al., "Supporting Information—Determination of the binding mode and interacting amino-acids for dibasic H3 receptor agonists", Bioorganic & Medicinal Chemistry, vol. 21, Jan. 2013, pp. S1-S3.
Loren, J.C. et al., "Synthesis of achiral and racemic catenanes based on terpyridine and a directionalized terpyridine mimic, pyridyl-phenanthroline", Org. Biomol. Chem., 3(17):3105-3116 (2005).

Louie, M.C. et al., "Androgen-induced recruitment of RNA polymerase II to a nuclear receptor13 p160 coactivator complex", PNAS, 100(5):2226-2230 (2003).
Makary, P., "Principles of salt formation." UK Journal of Pharmaceutical and Biosciences (2014); 2(4): 01-04.
Marriott et al., "Pharmaceutical Compounding and Dispensing," Second Edition, Pharmaceutical Press, 305 pages (2005).
Martin, S.J. et al., "A new precursor for the radiosynthesis of [$^{18}$F]FLT", Nuclear Medicine and Biology, 29:263-273 (2002).
Martin, S.K. et al., "N-terminal targeting of androgen receptor variant enhances response of castration resistant prostate cancer to taxane chemotherapy," Molecular Oncology, 2015, vol. 9, pp. 628-639.
Masiello, D. et al., "Bicalutamide Functions as an Androgen Receptor Antagonist by Assembly of a Transcriptionally Inactive Receptor", The Journal of Biological Chemistry, 277(29):26321-26326 (2002).
Mathur, A et al., "Subverting ER-Stress towards Apoptosis by Nelfinavir and Curcumin Coexposure Augments Docetaxel Efficacy in Castration Resistant Prostate Cancer Cells," PLoS ONE (2014) 9(8):e103109, 14 pages.
Mawji et al., "Preparation of ester derivatives of bisphenol-related compounds as androgen receptor modulators", CAPLUS Database Accession No. 2014:1909735, Document No. 161:737220, Entered on Jan. 6, 2015, 7 pages (Abstract).
McClurg, UL et al., "The novel anti-androgen candidate galeterone targets deubiquitinating enzymes, USP12 and USP46, to control prostate cancer growth and survival," Oncotarget, 2018, vol. 9, No. 38, pp. 24992-25007.
Melnyk, O. et al., "Neutralizing Anti-Vascular Endothelial Growth Factor Antibody Inhibits Further Growth of Established Prostate Cancer and Metastases in a Pre-Clinical Model", The Journal of Urology, 161:960-963 (1999).
Miller, J.I. et al., "The Clinical Usefulness of Serum Prostate Specific Antigen After Hormonal Therapy of Metastatic Prostate Cancer", The Journal of Urology, 147:956-961 (1992).
Mitsiades, C.S. et al., "Molecular biology and cellular physiology of refractoriness to androgen ablation therapy in advanced prostate cancer", Expert Opin. Investig. Drugs, 10(6):1099-1115 (2001).
Lima, Lidia M., and Barreiro, Eliezer J. "Bioisosterism: a useful strategy for molecular modification and drug design." Current Medicinal Chemistry (2005); 12.1: 23-49.
Myung, J-K et al., "An androgen receptor N-terminal domain antagonist for treating prostate cancer", The Journal of Clinical Investigation, 123(7):2948-2960 (2013).
Nakazawa, H. et al., "In vitro assay of hydrolysis and chlorohydroxy derivatives of bisphenol A diglycidyl ether for estrogenic activity", Food and Chemical Toxicology, 40:1827-1832 (2002).
Nazareth, L.V. et al, "Activation of the Human Androgen Receptor through a Protein Kinase A Signaling Pathway", The Journal of Biological Chemistry, 271 (33):19900-19907 (1996).
Nedolya, N. A. et al., Zhurnal Organicheskoi Khimii, 30(8): 1163-1166 (1994) (non-English document).
Nishikawa et al., "Epichlorohydrin derivative-based modifier of cellulose fibers and modification method of cellulose fibers,"0 Accession No. 2000:98153 CAPLUS (2009).
Noble, R. L., "The development of prostatic adenocarcinoma in Nb Rats following prolonged sex hormone administration", Cancer Research, 37:1929-1933 (1977).
Noble, R. L., "Sex steroids as a cause of adenocarcinoma of the dorsal prostate in Nb Rats, and their influence on the growth of transplants", Oncology, 34:138-141 (1977).
Ogawa, Y. et al., "Estrogenic activities of chemicals related to food contact plastics and rubbers tested by the yeast two-hybrid assay," Food Additives and Contaminants, 23:4, 422-430 (2006).
Paris, F. et al., "Phenylphenols, biphenols, bisphenol-A and 4-tert-octyphenol exhibit α and β estrogen activities and antiandrogen activity in reporter cell lines," Molecular and Cellular Endocrinology, 193:43-49 (2002).
Patani and LaVoie, "Bioisosterism: A Rational Approach in Drug Design", Chem. Rev., 96: 3147-3176 (1996).
Penczek, P. et al., "Synthesis and cyclotrimerization of dipropargyl derivatives of diepoxides," Database CAPLUS [Online] Chemical

(56) References Cited

OTHER PUBLICATIONS

Abstracts Service, Columbus, Ohio, retrieved from STN CA Caesar Accession No. 1995:741510 (1995), 2 pages.
Penczek, P. et al., "Synthesis and cyclotrimerization of dipropargyl derivatives of diepoxides," Polimery, (Warsaw), 40(5):274-277 (1995).
Petersen, H. et al., "Determination of bisphenol A diglycidyl ether (BADGE) and its derivatives in food: identification and quantification by internal Standard", Eur. Food Res. Technol., 216:355-364 (2003).
Poouthree, K. et al., "Comparison of resolution in microemulsion EKC and MEKC employing suppressed electroosmosis: Application to bisphenol-A-diglycidyl ether and its derivatives", Electrophoresis, 28920):3705-3711 (2007).
Poustka, J. et al., "Determination and occurrence of bisphenol A, bisphenol A diglycidyl ether, and bisphenol F diglycidyl ether, including their derivatives, in canned foodstuffs' from the Czech retail market," Czech J. Food Sci., 25(4):221-229 (2006).
Poustková et al., "Stability of bisphenol A diglycidyl ether and bisphenol F diglycidyl ether in water-based food simulants." European Food Research and Technology, 219(5): 534-539 (2004).
PubChem Compound Summary for CID 15305867, '4-Acetyl-4'-ethylbiphenyl', U.S. National Library of Medicine, Feb. 9, 2007, pp. 1-17; retrieved from https://pubchem.ncbi.nlm.nih.gov/compound/15305867.
PubChem Compound Summary for CID 18533308, '2-[4-[[4-(Aminomethoxy)phenyl]methyl]-2-methylphenoxy]acetic acid', U.S. National Library of Medicine, Dec. 4, 2007, pp. 1-15 retrieved from https://pubchem.ncbi.nlm.nih.gov/compound/18533308.
Qin et al., "Discovery of QCA570 as an Exceptionally Potent and Efficacious Proteolysis Targeting Chimera (PROTAC) Degrader of the Bromodomain and Extra-Terminal (BET) Proteins Capable of Inducing Complete and Durable Tumor Regression," J Med Chem. 2018. Vol. 61(15), pp. 6665-6704.
Quayle, S. et al., "Androgen receptor decoy molecules block the growth of prostate cancer", PNAS, 104(4):1331-1336 (2007).
Raina et al., "PROTAC-induced BET protein degradation as a therapy for castration-resistant prostate cancer," PNAS, Jun. 28, 2016, vol. 113, No. 26, pp. 7124-7129.
Rao, B.R. et al., "Endocrine Factors in Common Epithelial Ovarian Cancer", Endocrine Reviews, 12(1):14-26 (1991).
Reader, C. E. L., "Epoxy Resin Derivatives for Stoving Systems", Surface Coatings Australia, 25(10):6-9 (1988).
Reid, J. et al., "Conformational Analysis of the Androgen Receptor Amino-terminal Domain Involved in Transactivation," The Journal of Biological Chemistry, 277:20079-20086 (2002).
Risch, H.A., "Hormonal Etiology of Epithelial Ovarian Cancer, With a Hypothesis Concerning the Role of Androgens and Progesterone", Journal of the National Cancer Institute, 90(23):1774-1786 (1998).
Riu, A. et al., "Characterization of Novel Ligands of ERα, Erβ, and PPARγ: The Case of Halogenated Bisphenol A and Their Conjugated Metabolites", Toxicology Sciences, 122(2): 372-382 (2011).
Roberts, J. T. et al., "Adenocarcinoma of Prostate in 40-Year-Old Body-Builder", Lancet, 2:742 (1986).
Roberts et al., "Emerging drugs for hepatocellular carcinoma," Expert Opin Emerg Drugs, 11(3):469-487 (2006).
Rokicki, G. et al., "Reactions of 4-chloromethyl-1,3-dioxolan-2-one with phenols as a new route to polyols and cyclic carbonates", Journal f. prakt. Chemie., 327:718-722 (1985).
Ross, R.K. et al., "Androgen Metabolism and Prostate Cancer: Establishing a Model of Genetic Susceptibility", European Urology, 35:355-361 (1999).
Roulin et al., "Targeting renal cell carcinoma with NVP-BEZ235, a dual PI3K/mTOR inhibitor, in combination with sorafenib," Mol Cancer, 10:90 (2011), 12 pages.
Rusu, E. et al.: "Photosensitive compounds with chloromethyl groups", Revue Roumaine de Chimie, 45(5):451-456 (2000).
Sadar, M., "Androgen-independent Induction of Prostate-specific Antigen Gene Expression via Cross-talk between the Androgen Receptor and Protein Kinase A signal Transduction Pathways," The Journal of Biological Chemistry, 274(12):7777-7783 (1999).
Sadar, M. et al., "Prostate cancer: molecular biology of early progression to androgen independence", Endocrine-Related Cancer, 6:487-502 (1999).
Sadar, M.D. et al., "Characterization of a New in Vivo Hollow Fiber Model for the Study of Progression of Prostate Cancer to Androgen Independence", Molecular Cancer Therapeutics, 1:629-637 (2002).
Sato, N. et al., "Intermittent Androgen Suppression Delays Progression to Androgen-independent Regulation of Prostate-specific Antigen Gene in the LNCaP Prostate Tumour Model", J. Steroid Biochem. Mol. Biol., 58:139-146 (1996).
Sato, N. et al., "A Metastatic and Androgen-sensitive Human Prostate Cancer Model Using Intraprostatic Inoculation of LNCaP Cells in SCID Mice", Cancer Research, 57:1584-1589 (1997).
Satoh, K. et al., "Study on Anti-Androgenic Effects of Bisphenol a Diglycidyl Ether (BADGE), Bisphenol F Diglycidyl Ether (BFDGE) and Their Derivatives Using Cells Stably Transfected with Human Androgen Receptor, AR-EcoScreen", Food and Chemical Toxicology, 42:983-993 (2004).
Schaefer, A. et al., "Migration from can coatings: Part 3. Synthesis, identification and quantification of migrating epoxy-based substances below 1000 Da", Food Additives and Contaminants, 21(4):390-405 (2004).
Schellhammer, "An evaluation of bicalutamide in the treatment of prostate cancer." Expert Opinion on Pharmacotherapy, 3(9): 1313-1328 (2002).
Sharp et al., "Targeting Androgen Receptor Aberrations in Castration-Resistant Prostate Cancer," Clin Cancer Res., Sep. 1, 2016 ;22(17):4280-4282.
Silverman, R. B., The Organic Chemistry of Drug Design and Drug Action, Academic Press, Inc., Harcourt Brace Jovanovich, pp. 15-20, 9 pages (1992).
Snoek, R. et al., "Induction of Cell-free, In Vitro Transcription by Recombinant Androgen Receptor Peptides", J. Steroid Biochem. Mol. Biol., 59:243-250 (1996).
Stanciuc et al., "Reaction of Pyrylium Salts with Nucleophiles. 23: Triarylethene Derivatives Containing an Oxyalkyleneamino or Oxyalkylene-N-pyridinium Side Chain", Journal of Pharmaceutical Sciences, vol. 82, No. 9, Sep. 1993, pp. 927-933.
Still, W. C. et al., "Rapid Chromatographic Technique for Preparative Separations with Moderate Resolution", J. Org. Chem., 43(14):2923-2925 (1978).
STN Structure Search, dated Oct. 30, 2014 citing PL 135932, 3 pages.
Strub and McKim, "Dimethyl Sulfoxide USP, PhEur in Approved Pharmaceutical Products and Medical Devices", PharmaTech.com, 6 pages (2008). http://www.pharmtech.com/print/224268 ?page=full&rel=canonical.
Sun, S. et al., "Castration resistance in human prostate cancer is conferred by a frequently occurring androgen receptor splice variant", The Journal of Clinical Investigation, 120(8):2715-30 (2010).
Tanji, N. et al., "Growth Factors: Roles in Andrology", Archives of Andrology, 47:1-7 (2001).
Taplin, M.E. et al., "Selection for Androgen Receptor Mutations in Prostate cancers Treated with Androgen Antagonist", Cancer Research, 59:2511-2515 (1999).
Taskeen, A. et al., "Analysis of bisphenol A in canned food: A mini review", Asian Journal of Chemistry, 22(5):4133-4135 (2010).
Thomson, A.A., "Role of androgens and fibroblast growth factors in prostatic development", Reproduction, 121:187-195 (2001).
Ueda, T. et al., "Activation of the Androgen Receptor N-terminal Domain by Interleukin-6 via MAPK and STAT3 Signal Transduction Pathways", The Journal of Biological Chemistry, 277(9)7076-7085 (2002).
Ueda, T. et al., "Ligand-independent Activation of the Androgen Receptor by Interleukin-6 and the Role of Steroid Receptor Coactivator-1 in Prostate cancer Cells", The Journal of Biological Chemistry, 277(41): 38087-38094 (2002).
Uematsu, Y. et al., "Chlorohydrins of bisphenol A diglycidyl ether (BADGE) and bisphenol F diglycidyl ether (BFDGE) in canned foods and ready-to-drink coffees from the Japanese market", Food Additives and Contaminants, 18(2):177-185 (2001).

(56) References Cited

OTHER PUBLICATIONS

Van Der Kwast, T.H. et al., "Androgen Receptors in Endocrine-Therapy-Resistant Human Prostate Cancer", Inter. J. Cancer, 48:189-193 (1991).
Van Scherpenzeel, M. et al., "Nanomolar affinity, iminosugar-based chemical probes for specific labeling of lysosomal glucocerebrosidase", Bioorganic & Medicinal Chemistry, 18:267-273 (2010).
Venkatesh, Srini, and Lipper, Robert A. "Role of the development scientist in compound lead selection and optimization." Journal of Pharmaceutical Sciences (2000); 89.2: 145-154.
Vippagunta et al., "Crystalline solids," Advanced Drug Delivery Reviews (2001) 48: 3-26.
Walfried et al., "Bisphenol F-Diglycidylether (BFDGE) und Folgeprodukte in Konservenfullgutern: Synthese und Analytik," Deutsche Lebensmittel-Rundschau, vol. 96, No. 11, 2000, pp. 417-422 (with English abstract).
Wang, G. et al., "Identification of genes targeted by the androgen and PKA signaling pathways in prostate cancer cells", Oncogene, 25:7311-7323 (2006).
Wang, Q. et al., "Spatial and Temporal Recruitment of Androgen Receptor and Its Coactivators Involves Chromosomal Looping and Polymerase Tracking", Molecular Cell, 19:631-642 (2005).
Wetherill, Y. B. et al., "In vitro molecular mechanisms of bisphenol A action," Reproductive Toxicology, 24:178-198 (2007).
Wiedmann and Naqwi, "Pharmaceutical salts: Theory, use in solid dosage forms and in situ preparation in an aerosol." Asian Journal of Pharmaceutical Sciences (2016); 11(6): 722-734.
Wilcox and Cowart, "New Approaches to Synthetic Receptors. Synthesis and Host Properties of a Water Soluble Macrocyclic Analog of Troger's Base", Tetrahedron Letters, 27(46): 5563-5566 (1986).
Wilding, G., "The Importance of Steroid Hormones in Prostate Cancer", Cancer Surveys, 14:113-130 (1992).
Wilson, J.D. et al., "Long-Term Conseguences of Castration in Men: Lessons from the Skoptzy and the Eunuchs of the Chinese and Ottoman Courts", The Journal of Clinical Endocrinology & Metabolism, 84:4324-4331 (1999).
Wolff (ed.) et al., Burger's Medicinal Chemistry and Drug Discovery, Fifth Edition, vol. I: Principles and Practice, 1995, pp. 975-977..
Wong, C. et al., "Steroid Reguirement for Androgen Receptor Dimerization and DNA Binding", J. Bioi. Chern., 268(25):19004-19012 (1993).
Xu, X. et al, "Synthesis and Stability Study of Dental Monomers Containing Methacrylamidoethyl Phosphonic Acids", Journal of Polymer Science: Part A Polymer Chemistry, 45:99-110 (2007).
Yang et al., "Targeting Androgen Receptor Activation Function-1 with EPI to Overcome Resistance Mechanisms in Castration-Resistant Prostate Cancer," Clin Cancer Res; 22(17) Sep. 1, 2016, 4466-4477.
Ye, Deyong, "An Introduction to Computer-Aided Drug Design", 3 pages, Jan. 31, 2004 (non-English document).
Yonekubo, J. et al., "Concentrations of Bisphenol A, Bisphenol A Diglycidyl Ether, and Their Derivatives in Canned Foods in Japanese Markets," J. Agric. Food Chem., 2008, 56, 2041-2047.
Yong, Eu Leong, et al. "Molecular basis of androgen receptor diseases." Annals of Medicine (2000); 32.1: 15-22.
Zuhayra, M. et al., "New approach for the synthesis of [$^{18}$F]fluoroethyltyrosine for cancer imaging: Simple, fast, and high yielding automated synthesis", Bioorganic & Medicinal Chemistry, 17:7441-7448 (2009).
Extended European Search Report in Application No. EP 12768410.8 dated Sep. 22, 2014, 10 pages.
Extended European Search Report in Application No. EP 14793978.9 dated Sep. 1, 2016, 8 pages.
Supplementary European Search Report in EP Application No. 09771876.1 dated Jun. 20, 2011, 5 pages.
Supplementary European Search Report in EP Application No. 11731645.5 dated Jun. 20, 2013, 11 pages.
Extended European Search Report in Application No. EP 14843037.4 dated Mar. 8, 2017, 5 pages.
Extended European Search Report in Application No. EP 17177010.0 dated Oct. 20, 2017, 10 pages.
Extended European Search Report in Application No. 16736999.0 dated May 24, 2018, 14 pages.
Extended European Search Report in Application No. 21212648.6 dated Feb. 21, 2022, 8 pages.
Extended European Search Report for European Application No. 17781660.0 dated Oct. 31, 2019, 8 pages.
Decision of Refusal for Japanese Application No. 2011-515039, dated Dec. 2, 2014, 18 pages (English translation).
International Search Report for International Application No. PCT/CA2009/000902 dated Sep. 1, 2009, 4 pages.
Written Opinion for International Application No. PCT/CA2009/000902 dated Sep. 1, 2009, 6 pages.
International Preliminary Report on Patentability for International Application No. PCT/CA2009/000902 dated Jan. 5, 2011, 7 pages.
International Search Report for International Application No. PCT/US2012/032584 dated Jul. 31, 2012, 3 pages.
Written Opinion for International Application No. PCT/US2012/032584 dated Jul. 31, 2012, 5 pages.
International Preliminary Report on Patentability for PCT/US2012/032584 dated Oct. 8, 2013, 6 pages.
International Search Report for International Application No. PCT/US2012/033959 dated Jul. 18, 2012, 3 pages.
Written Opinion for International Application No. PCT/US2012/033959 dated Jul. 18, 2012, 7 pages.
International Preliminary Report on Patentability for International Application No. PCT/US2012/033959 dated Oct. 22, 2013, 8 pages.
International Search Report for International Application No. PCT/US2012/033957 dated Jul. 18, 2012, 3 pages.
Written Opinion for International Application No. PCT/US2012/033957 dated Jul. 18, 2012, 5 pages.
International Preliminary Report on Patentability for International Application No. PCT/US2012/033957 dated Oct. 22, 2013, 6 pages.
International Search Report for International Application No. PCT/CA2011/000019 dated Mar. 21, 2011, 7 pages.
Written Opinion for International Application No. PCT/CA2011/000019 dated Mar. 21, 2011, 7 pages.
International Preliminary Report on Patentability for International Application No. PCT/CA2011/000019 dated Jul. 10, 2012, 8 pages.
International Search Report for International Application No. PCT/CA2011/000021 dated Apr. 18, 2011, 8 pages.
Written Opinion for International Application No. PCT/CA2011/000021 dated Apr. 18, 2011, 7 pages.
International Preliminary Report on Patentability for International Application No. PCT/CA2011/000021 dated Jul. 10, 2012, 8 pages.
International Search Report for International Application No. PCT/US2012/051481 dated Nov. 26, 2012, 4 pages.
Written Opinion for International Application No. PCT/US2012/051481 dated Nov. 26, 2012, 7 pages.
International Preliminary Report on Patentability for International Application No. PCT/US2012/051481 dated Feb. 25, 2014, 8 pages.
International Search Report for International Application No. PCT/US2012/051923 dated Jan. 28, 2013, 4 pages.
Written Opinion for International Application No. PCT/US2012/051923 dated Jan. 28, 2013, 8 pages.
International Preliminary Report on Patentability for International Application No. PCT/US2012/051923 dated Feb. 25, 2014, 9 pages.
International Search Report and Written Opinion for International Application No. PCT/CA2014/000414 dated Aug. 5, 2014, 6 pages.
International Preliminary Report on Patentability for International Application No. PCT/CA2014/000414 dated Nov. 10, 2015, 7 pages.
International Search Report and Written Opinion for International Application No. PCT/CA2014/000685 dated Dec. 4, 2014, 13 pages.
International Preliminary Report on Patentability for International Application No. PCT/CA2014/000685 dated Mar. 15, 2016, 7 pages.
International Search Report and Written Opinion for International Application No. PCT/CA2015/000533 dated Dec. 18, 2015, 11 pages.

(56) References Cited

OTHER PUBLICATIONS

International Preliminary Report on Patentability for International Application No. PCT/CA2015/000533 dated Apr. 18, 2017, 7 pages.
International Search Report and Written Opinion for International Application No. PCT/CA2015/000535 dated Dec. 23, 2015, 9 pages.
International Preliminary Report on Patentability for International Application No. PCT/CA2015/000535 dated Apr. 18, 2017, 6 pages.
International Search Report and Written Opinion for International Application No. PCT/CA2016/000008 dated Mar. 15, 2016, 13 pages.
International Preliminary Report on Patentability for International Application No. PCT/CA2016/000008 dated Jul. 18, 2017, 7 pages.
International Search Report and Written Opinion for International Application No. PCT/CA2016/000070 dated Jun. 2, 2016, 10 pages.
International Search Report and Written Opinion for International Application No. PCT/CA2017/000083 dated Aug. 3, 2017, 14 pages.
International Preliminary Report on Patentability for International Application No. PCT/CA2016/000070 dated Sep. 12, 2017, 6 pages.
International Search Report and Written Opinion for International Application No. PCT/CA2017/000141 dated Sep. 1, 2017, 11 pages.
International Search Report and Written Opinion for International Application No. PCT/CA2017/000201 dated Dec. 8, 2017, 9 pages.
International Search Report and Written Opinion for International Application No. PCT/US2019/057034 dated Feb. 6, 2020, 10 pages.
International Search Report and Written Opinion for International Application No. PCT/US2020/025545 dated Jul. 9, 2020, 11 pages.
International Search Report and Written Opinion for International Application No. PCT/US2020/025542 dated Aug. 14, 2020, 10 pages.
International Search Report and Written Opinion for International Application No. PCT/US2020/025539 dated Aug. 18, 2020, 11 pages.
International Search Report and Written Opinion for International Application No. PCT/US2021/027771 dated Jul. 9, 2021, 8 pages.
International Search Report and Written Opinion for International Application No. PCT/US2021/050644 dated Feb. 3, 2022, 8 pages.
Auberson et al., "Ligand Specific Efficiency (LSE) Index for PET Tracer Optimization," ChemMedChem, vol. 11, No. 13, Jul. 5, 2016, pp. 1415-1427.
Osuka et al., "Synthesis and Photoexcited-State Dynamics of Aromatic Group-Bridged Carotenoid-Porphyrin Dyads and Carotenoid-Porphyrin-Pyromeilitimide Triads," J. Am. Chem. Soc. 1993, 115, 9439-9452.
Extended European Search Report for European Application No. 19873360.2 dated Jun. 15, 2022, 10 pages.
International Search Report and Written Opinion for International Application No. PCT/US2022/025016, dated Jun. 29, 2022, 9 pages.
PubChem Compound Summary for CID 146484310, 'N-[4-[[4-[2-[3-chloro-4-(2-chloroethoxy)-5-cyanophenyl]propan-2-yl]phenoxy]methyl]pyrimidin-2yl]methanesulfonamide', U.S. National Library of Medicine, Jun. 27, 2020, 8 pages; retrieved from https://pubchem.ncbi.nlm.nih.gov/compound/146484310.

* cited by examiner

SOLID FORMS OF AN N-TERMINAL DOMAIN ANDROGEN RECEPTOR INHIBITOR AND USES THEREOF

CROSS-REFERENCE TO RELATED APPLICATIONS

This application is a continuation of U.S. application Ser. No. 17/526,660, filed Nov. 15, 2021, which is a continuation of U.S. application Ser. No. 17/342,923, filed Jun. 9, 2021, now U.S. Pat. No. 11,242,324, which is a continuation of U.S. application Ser. No. 17/233,161, filed Apr. 16, 2021, which claims the benefit of U.S. Provisional Application No. 63/011,671, filed Apr. 17, 2020, the disclosures of each of which is incorporated by reference herein in its entirety.

FIELD OF THE INVENTION

The present disclosure relates to solid forms of Compound I or a pharmaceutically acceptable salt and/or solvate thereof, pharmaceutical compositions comprising the crystalline form, and therapeutic uses thereof. In particular, the present disclosure relates to solid forms of Compound I or a pharmaceutically acceptable salt and/or solvate thereof, which are useful for treating various diseases, including cancers such as prostate cancer.

BACKGROUND OF THE INVENTION

Androgens mediate their effects through the androgen receptor (AR). Androgens play a role in a wide range of developmental and physiological responses and are involved in male sexual differentiation, maintenance of spermatogenesis, and male gonadotropin regulation (R. K. Ross, G. A. Coetzee, C. L. Pearce, J. K. Reichardt, P. Bretsky, L. N. Kolonel, B. E. Henderson, E. Lander, D. Altshuler & G. Daley, *Eur Urol* 35, 355-361 (1999); A. A. Thomson, *Reproduction* 121, 187-195 (2001); N. Tanji, K. Aoki & M. Yokoyama, *Arch Androl* 47, 1-7 (2001)). Several lines of evidence show that androgens are associated with the development of prostate carcinogenesis. Firstly, androgens induce prostatic carcinogenesis in rodent models (R. L. Noble, *Cancer Res* 37, 1929-1933 (1977); R. L. Noble, *Oncology* 34, 138-141 (1977)) and men receiving androgens in the form of anabolic steroids have a higher incidence of prostate cancer (J. T. Roberts & D. M. Essenhigh, *Lancet* 2, 742 (1986); J. A. Jackson, J. Waxman & A. M. Spiekerman, *Arch Intern Med* 149, 2365-2366 (1989); P. D. Guinan, W. Sadoughi, H. Alsheik, R. J. Ablin, D. Alrenga & I. M. Bush, *Am J Surg* 131, 599-600 (1976)). Secondly, prostate cancer does not develop if humans or dogs are castrated before puberty (J. D. Wilson & C. Roehrborn, *J Clin Endocrinol Metab* 84, 4324-4331 (1999); G. Wilding, *Cancer Surv* 14, 113-130 (1992)). Castration of adult males causes involution of the prostate and apoptosis of prostatic epithelium while eliciting no effect on other male external genitalia (E. M. Bruckheimer & N. Kyprianou, *Cell Tissue Res* 301, 153-162 (2000); J. T. Isaacs, *Prostate* 5, 545-557 (1984)). This dependency on androgens provides the underlying rationale for treating prostate cancer with chemical or surgical castration also known as androgen ablation therapy (ABT) or androgen deprivation therapy (ADT).

Androgen receptor (AR) is a transcription factor that plays dual roles in breast cancer cells: promoting or inhibiting proliferation depending on expression and activity of estrogen receptor-alpha. Expression of AR is detected in up to 90% of all breast cancers.

Androgens also play a role in female diseases such as polycystic ovary syndrome as well as cancers. One example is ovarian cancer where elevated levels of androgens are associated with an increased risk of developing ovarian cancer (K. J. Helzlsouer, A. J. Alberg, G. B. Gordon, C. Longcope, T. L. Bush, S. C. Hoffman & G. W. Comstock, *JAMA* 274, 1926-1930 (1995); R. J. Edmondson, J. M. Monaghan & B. R. Davies, *Br J Cancer* 86, 879-885 (2002)). The AR has been detected in a majority of ovarian cancers (H. A. Risch, *J Natl Cancer Inst* 90, 1774-1786 (1998); B. R. Rao & B. J. Slotman, *Endocr Rev* 12, 14-26 (1991); G. M. Clinton & W. Hua, *Crit Rev Oncol Hematol* 25, 1-9 (1997)), whereas estrogen receptor-alpha (ERa) and the progesterone receptor are detected in less than 50% of ovarian tumors.

The only effective treatment available for advanced prostate cancer is the withdrawal of androgens which are essential for the survival of prostate luminal cells. Androgen ablation therapy causes a temporary reduction in tumor burden concomitant with a decrease in serum prostate-specific antigen (PSA). Unfortunately, prostate cancer can eventually grow again in the absence of testicular androgens (castration-resistant disease) (Huber et al 1987 *Scand J. Urol Nephrol.* 104, 33-39). Castration-resistant prostate cancer that is still driven by AR is biochemically characterized before the onset of symptoms by a rising titre of serum PSA (Miller et al 1992 *J. Urol.* 147, 956-961). Once the disease becomes castration-resistant most patients succumb to their disease within two years.

The AR has distinct functional domains that include the carboxy-terminal ligand-binding domain (LBD), a DNA-binding domain (DBD) comprising two zinc finger motifs, and an N-terminus domain (NTD) that contains two transcriptional activation units (tau1 and tau5) within activation function-1 (AF-1). Binding of androgen (ligand) to the LBD of the AR results in its activation such that the receptor can effectively bind to its specific DNA consensus site, termed the androgen response element (ARE), on the promoter and enhancer regions of "normally" androgen regulated genes, such as PSA, to initiate transcription. The AR can be activated in the absence of androgen by stimulation of the cAMP-dependent protein kinase (PKA) pathway, with interleukin-6 (IL-6) and by various growth factors (Culig et al 1994 *Cancer Res.* 54, 5474-5478; Nazareth et al 1996 *J. Biol. Chem.* 271, 19900-19907; Sadar 1999 *J. Biol. Chem.* 274, 7777-7783; Ueda et al 2002 A *J. Biol. Chem.* 277, 7076-7085; and Ueda et al 2002 B *J. Biol. Chem.* 277, 38087-38094). The mechanism of ligand-independent transformation of the AR has been shown to involve: 1) increased nuclear AR protein suggesting nuclear translocation; 2) increased AR/ARE complex formation; and 3) the AR-NTD (Sadar 1999 *J. Biol. Chem.* 274, 7777-7783; Ueda et al 2002 A *J. Biol. Chem.* 277, 7076-7085; and Ueda et al 2002 B *J. Biol. Chem.* 277, 38087-38094). The AR can be activated in the absence of testicular androgens by alternative signal transduction pathways in castration-resistant disease, which is consistent with the finding that nuclear AR protein is present in secondary prostate cancer tumors (Kim et al 2002 *Am. J. Pathol.* 160, 219-226; and van der Kwast et al 1991 *Inter. J. Cancer* 48, 189-193).

Clinically available inhibitors of the AR include non-steroidal antiandrogens such as bicalutamide (Casodex™), nilutamide, flutamide, and enzalutamide. There is also a class of steroidal antiandrogens, such as cyproterone acetate and spironolactone. Both steroidal and non-steroidal antiandrogens target the LBD of the AR and predominantly fail presumably due to poor affinity and mutations that lead to activation of the AR by these same antiandrogens (Taplin, M. E., Bubley, G. J., Kom Y. J., Small E. J., Uptonm M., Rajeshkumarm B., Balkm S. P., *Cancer Res.*, 59, 2511-2515 (1999)), and constitutively active AR splice variants. Antiandrogens have no effect on the constitutively active AR splice variants that lack the ligand-binding domain (LBD) and are associated with castration-recurrent prostate cancer (Dehm S M, Schmidt L J, Heemers H V, Vessella R L, Tindall D J., *Cancer Res* 68, 5469-77, 2008; Guo Z, Yang X, Sun F, Jiang R, Linn D E, Chen H, Chen H, Kong X, Melamed J, Tepper C G, Kung H J, Brodie A M, Edwards J, Qiu Y., *Cancer Res.* 69, 2305-13, 2009; Hu et al 2009 *Cancer Res.* 69, 16-22; Sun et al 2010 *J. Clin Invest.* 2010 120, 2715-30) and resistant to abiraterone and enzalutamide (Antonarakis et al., *N Engl J Med.* 2014, 371, 1028-38; Scher et al *JAMA Oncol.* 2016 doi: 10.1001). Conventional therapy has concentrated on androgen-dependent activation of the AR through its C-terminal domain.

Other relevant AR antagonists previously reported (see, WO 2010/000066, WO 2011/082487; WO 2011/082488; WO 2012/145330; WO 2015/031984; WO 2016/058080; and WO 2016/058082) that bind to full-length AR and/or truncated AR splice variants that are currently being developed include: AR degraders such as niclosamide (Liu C et al 2014), galeterone (Njar et al 2015; Yu Z at al 2014), and ARV-330/Androgen receptor PROTAC (Neklesa et al 2016 *J Clin Oncol* 34 suppl 2S; abstr 267); AR DBD inhibitor VPC-14449 (Dalal K et al 2014 *J Biol Chem.* 289(38): 26417-29; Li H et al 2014 *J Med Chem.* 57(15):6458-67); antiandrogens apalutamide (Clegg N J et al 2012), ODM-201 (Moilanen A M et al 2015), ODM-204 (Kallio et al *J Clin Oncol* 2016 vol. 34 no. 2_suppl 230), TAS3681 (Minamiguchi et al 2015 *J Clin Oncol* 33, suppl 7; abstr 266); and AR NTD inhibitors 3E10-AR44lbsAb (Goicochea N L et al 2015), and sintokamide (Sadar et al 2008; Banuelos et al 2016).

The AR-NTD is also a target for drug development (e.g. WO 2000/001813; Myung et al. *J. Clin. Invest* 2013, 123, 2948), since the NTD contains Activation-Function-1 (AF-1) which is the essential region required for AR transcriptional activity (Jenster et al 1991. *Mol Endocrinol.* 5, 1396-404). The AR-NTD importantly plays a role in activation of the AR in the absence of androgens (Sadar, M. D. 1999 *J. Biol. Chem.* 274, 7777-7783; Sadar M D et al 1999 *Endocr Relat Cancer.* 6, 487-502; Ueda et al 2002 *J. Biol. Chem.* 277, 7076-7085; Ueda 2002 *J. Biol. Chem.* 277, 38087-38094; Blaszczyk et al 2004 *Clin Cancer Res.* 10, 1860-9; Dehm et al 2006 *J Biol Chem.* 28, 27882-93; Gregory et al 2004 *J Biol Chem.* 279, 7119-30). The AR-NTD is important in hormonal progression of prostate cancer as shown by application of decoy molecules (Quayle et al 2007, *Proc Natl Acad Sci USA.* 104,1331-1336).

While the crystal structure has been resolved for the AR C-terminus LBD, this has not been the case for the NTD due to its high flexibility and intrinsic disorder in solution (Reid et al 2002 *J. Biol. Chem.* 277, 20079-20086) thereby hampering virtual docking drug discovery approaches. Compounds that modulate AR, potentially through interaction with NTD domain, include the bisphenol compounds disclosed in published PCT Nos: WO 2010/000066, WO 2011/082487; WO 2011/082488; WO 2012/145330; WO 2012/139039; WO 2012/145328; WO 2013/028572; WO 2013/028791; WO 2014/179867; WO 2015/031984; WO 2016/058080; WO 2016/058082; WO 2016/112455; WO 2016/141458; WO 2017/177307; WO 2017/210771; WO 2018/045450; WO 2019/226991; WO 2020/081999, and WO 2020/198710, which are hereby incorporated by reference in their entireties.

Transcriptionally active androgen receptor plays a major role in CRPC in spite of reduced blood levels of androgen (Karantanos, T. et al *Oncogene* 2013, 32, 5501-5511; Harris, W. P. et al *Nature Clinical Practice Urology*, 2009, 6, 76-85). AR mechanisms of resistance to ADT include: overexpression of AR (Visakorpi, T. et al *Nature Genetics* 1995, 9, 401-406; Koivisto, P. et al *Scandinavian Journal of Clinical and Laboratory Investigation Supplementum* 1996, 226, 57-63); gain-of-function mutations in the AR LBD (Culig Z. et al *Molecular Endocrinology* 1993, 7, 1541-1550); intratumoral androgen synthesis (Cai, C. et al *Cancer Research* 2011, 71, 6503-6513); altered expression and function of AR coactivators (Ueda, T. et al *The Journal of Biological Chemistry* 2002, 277, 38087-38094; Xu J. et al *Nature Reviews Cancer* 2009, 9, 615-630); aberrant post-translational modifications of AR (Gioeli D. et al *Molecular and Cellular Endocrinology* 2012, 352, 70-78; van der Steen T. et al *International Journal of Molecular Sciences* 2013, 14, 14833-14859); and expression of AR splice variants (AR-Vs) which lack the ligand-binding domain (LBD) (Karantanos, T. et al *Oncogene* 2013, 32, 5501-5511; Andersen R. J. et al Cancer Cell 2010, 17, 535-546; Myung J. K. et al *The Journal of Clinical Investigation* 2013, 123, 2948-2960; Sun S. et al *The Journal of Clinical Investigation* 2010, 120, 2715-2730). Anti-androgens such as bicalutamide and enzalutamide target AR LBD, but have no effect on truncated constitutively active AR-Vs such as AR-V7 (Li Y. et al *Cancer Research* 2013, 73, 483-489). Expression of AR-V7 is associated with resistance to current hormone therapies (Li Y. et al *Cancer Research* 2013, 73, 483-489; Antonarakis E. S. et al *The New England Journal of Medicine* 2014, 371, 1028-1038).

SUMMARY OF THE INVENTION

The present disclosure relates to a crystalline form of an androgen receptor modulator, Compound I, or a pharmaceutically acceptable salt, solvate, or solvate salt thereof.

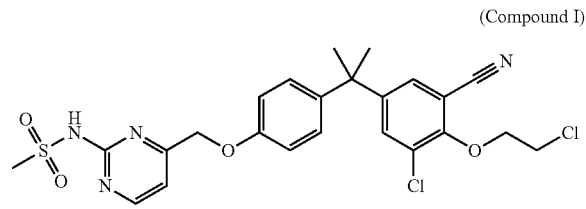 [SMILES: CC(C)(c1ccc(OCc2ccnc(NS(C)(=O)=O)n2)cc1)c1cc(Cl)c(OCCCl)c(C#N)c1]

(Compound I)

In one embodiment, Compound I is an androgen receptor N-terminal domain inhibitor.

The present disclosure relates to a crystalline form of Compound I or a pharmaceutically acceptable salt, solvate, or solvate salt thereof. In one embodiment, the crystalline form is anhydrous or non-solvated. In one embodiment of the crystalline form, Compound I is not present as a pharmaceutically acceptable salt.

In one embodiment of the present disclosure, the crystalline form of Compound I or a pharmaceutically acceptable salt, solvate, or solvate salt thereof exhibits an X-ray powder diffraction (XRPD) pattern comprising peaks at about 17.48±0.2, 20.78±0.2, and 21.80±0.2 degrees two-theta. In one embodiment, the XRPD pattern further comprises peaks at about 5.19±0.2 and 12.94±0.2 degrees two-theta. In one embodiment, the XRPD pattern further comprises at least two peaks selected from about 17.80±0.2, 18.74±0.2, 19.57±0.2, 22.59±0.2, 25.28±0.2, or 29.95±0.2 degrees two-theta.

In one embodiment of the present disclosure, the crystalline form of Compound I or a pharmaceutically acceptable salt, solvate, or solvate salt thereof exhibits an XRPD pattern comprising peaks in Table 1B. In one embodiment, the XRPD peaks at about 5.19±0.2, 12.94±0.2, 17.48±0.2, 20.78±0.2, and 21.80±0.2 degrees two-theta have peak intensities of at least 35%.

In one embodiment of the present disclosure, the crystalline form of Compound I is Form A exhibiting an XRPD pattern substantially similar to FIG. 1, provided that peaks at 27.3±0.2 and 31.7±0.2 degrees two-theta are excluded.

In one embodiment of the present disclosure, the crystalline form of Compound I or a pharmaceutically acceptable salt, solvate, or solvate salt thereof exhibits a differential scanning calorimetry (DSC) thermogram comprising an endotherm peak which onset at about 182° C.

In one embodiment of the present disclosure, the crystalline form of Compound I or a pharmaceutically acceptable salt, solvate, or solvate salt thereof exhibits a thermogravimetric analysis (TGA) thermogram comprising a change in slope which onset at about 284° C.

In one embodiment of the present disclosure, the crystalline form of Compound I or a pharmaceutically acceptable salt, solvate, or solvate salt thereof has a purity in the range of about 80% to about 99%. In one embodiment of the present disclosure, the crystalline form of Compound I or a pharmaceutically acceptable salt, solvate, or solvate salt thereof has a purity of about 95% or higher. In one embodiment, the crystalline form has a purity of about 97% or higher. In one embodiment, the crystalline form has a purity of about 99% or higher.

The present disclosure relates to an amorphous form of Compound I or a pharmaceutically acceptable salt, solvate, or solvate salt thereof. In one embodiment, the amorphous form is anhydrous or non-solvated. In one embodiment of the amorphous form, Compound I is not present as a pharmaceutically acceptable salt. In another embodiment, the amorphous form of Compound I or a pharmaceutically acceptable salt, solvate, or solvate salt thereof is in a pharmaceutical composition. In a specific embodiment, the pharmaceutical composition comprises Compound I in a solid dispersion.

In one embodiment of the present disclosure, the amorphous form of Compound I exhibits an XRPD pattern substantially similar to FIG. 7 (third spectrum from bottom), provided that peaks at 27.3±0.2 and 31.7±0.2 degrees two-theta are excluded.

The present disclosure relates to an amorphous form of Compound I or a pharmaceutically acceptable salt, solvate, or solvate salt thereof which exhibits a differential scanning calorimetry (DSC) thermogram comprising an exotherm peak at about 91° C. In one embodiment, the amorphous form exhibits a differential scanning calorimetry (DSC) thermogram comprising an endotherm peak which onset at about 178° C.

The present disclosure relates to an amorphous form of Compound I or a pharmaceutically acceptable salt, solvate, or solvate salt thereof which exhibits a glass transition temperature at about 61° C.

The present disclosure relates to an amorphous form of Compound I or a pharmaceutically acceptable salt, solvate, or solvate salt thereof which exhibits a thermogravimetric analysis (TGA) thermogram comprising a change in slope which onset at about 280° C.

In one embodiment of the present disclosure, the amorphous form of Compound I or a pharmaceutically acceptable salt, solvate, or solvate salt thereof has a purity in the range of about 80% to about 99%. In one embodiment of the present disclosure, the amorphous form of Compound I or a pharmaceutically acceptable salt, solvate, or solvate salt thereof has a purity of about 95% or higher. In one embodiment, the amorphous form has a purity of about 97% or higher. In one embodiment, the amorphous form has a purity of about 99% or higher.

The present disclosure also relates to a composition comprising any one of the crystalline forms or the amorphous forms of Compound I or a pharmaceutically acceptable salt, solvate, or solvate salt thereof as disclosed herein, and a pharmaceutically acceptable carrier.

In one embodiment, the compositions disclosed herein comprises a crystalline form is Form A. In one embodiment, the composition further comprises an amorphous form of Compound I or a pharmaceutically acceptable salt, solvate, or solvate salt thereof.

In one embodiment, any one of the compositions disclosed herein can further comprising an additional therapeutic agent. In one embodiment, any one of the compositions disclosed herein can further comprising one or more additional therapeutic agents.

The present disclosure also relates to a method for treating cancer comprising administering any one of the crystalline forms or the amorphous forms of Compound I or a pharmaceutically acceptable salt, solvate, or solvate salt thereof as disclosed herein. In one embodiment, the cancer is selected from prostate cancer, breast cancer, ovarian cancer, bladder cancer, pancreatic cancer, hepatocellular cancer, endometrial cancer, or salivary gland carcinoma. In one embodiment, the cancer is prostate cancer. In one embodiment, the prostate cancer is primary or localized prostate cancer, locally advanced prostate cancer, recurrent prostate cancer, advanced prostate cancer, metastatic prostate cancer, non-metastatic castration-resistant prostate cancer, metastatic castration-resistant prostate cancer, and hormone-sensitive prostate cancer. In one embodiment, the prostate cancer is metastatic castration-resistant prostate cancer. In one embodiment, the prostate cancer expresses full-length androgen receptor or truncated androgen receptor splice variant.

The present disclosure also relates to a method for modulating androgen receptor activity, administering any one of the crystalline forms or the amorphous forms of Compound I or a pharmaceutically acceptable salt, solvate, or solvate salt thereof as disclosed herein. In one embodiment, the modulating androgen receptor activity is for treating a condition or disease selected from prostate cancer, breast cancer, ovarian cancer, bladder cancer, pancreatic cancer, hepatocellular cancer, endometrial cancer, salivary gland carcinoma, hair loss, acne, hirsutism, ovarian cysts, polycystic ovary disease, precocious puberty, spinal and bulbar muscular atrophy, or age-related macular degeneration.

DETAILED DESCRIPTION

Figure 1:
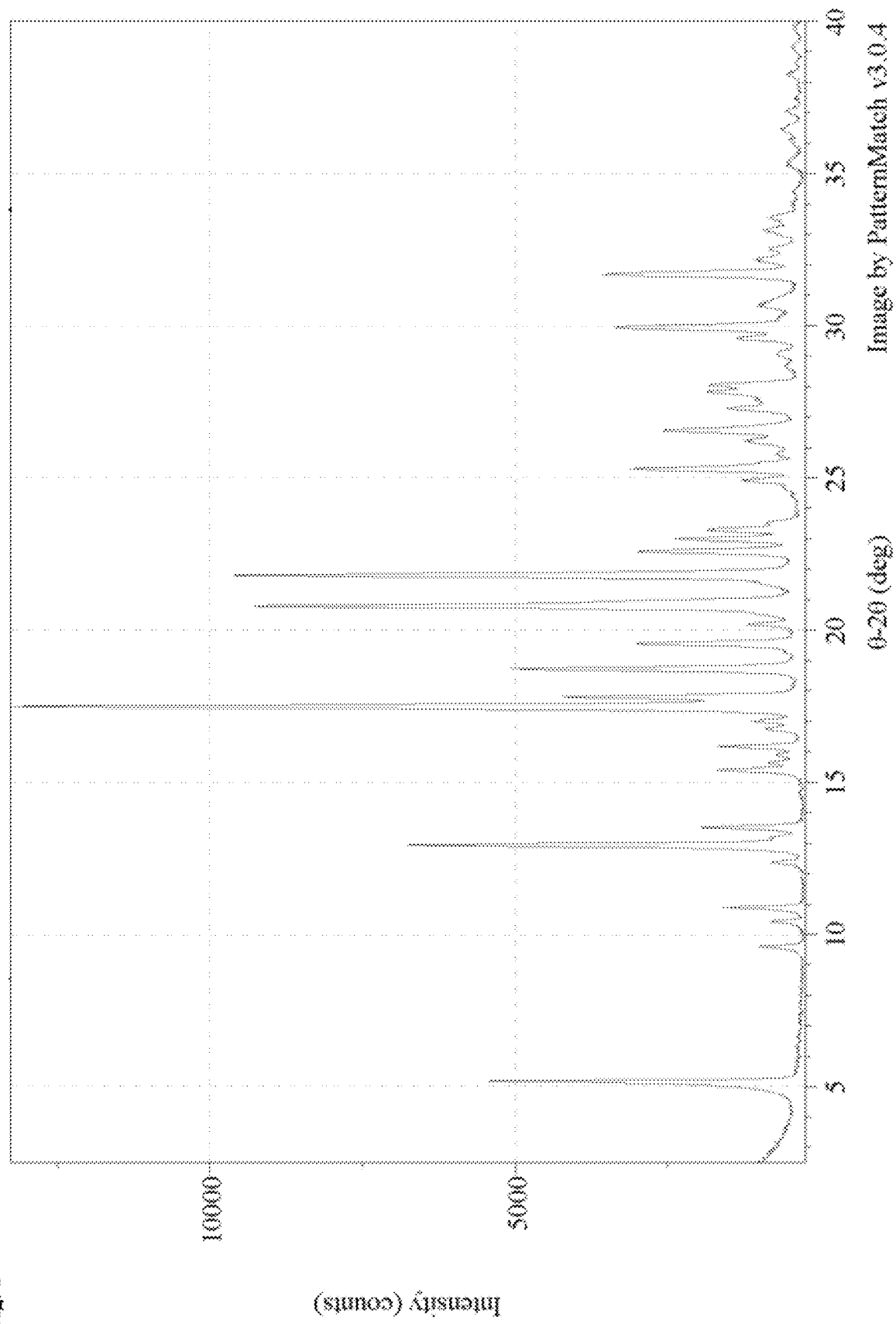
FIG. 1 shows X-ray powder diffraction (XRPD) spectrum of crystalline Form A of Compound I.

All publications, patents and patent applications, including any drawings and appendices therein are incorporated by reference in their entirety for all purposes to the same extent as if each individual publication, patent or patent application, drawing, or appendix was specifically and individually indicated to be incorporated by reference in its entirety for all purposes.

Definitions

While the following terms are believed to be well understood by one of ordinary skill in the art, the following definitions are set forth to facilitate explanation of the presently disclosed subject matter.

Compound I is N-{4-[(4-{2-[3-chloro-4-(2-chloroethoxy)-5-cyanophenyl]propan-2-yl}phenoxy)methyl]pyrimidin-2-yl}methanesulfonamide having the structure shown below. Compound I is disclosed in WO 2020/081999, which is hereby incorporated by reference in its entirety. In one embodiment, Compound I is an androgen receptor N-terminal domain inhibitor.

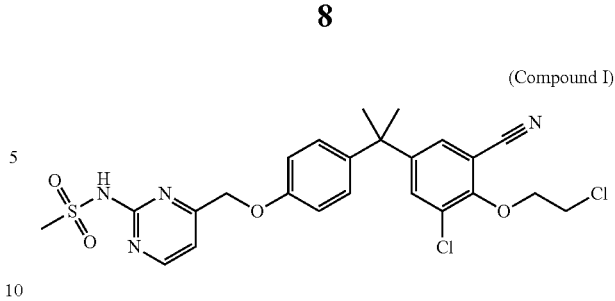

(Compound I)

Throughout the present specification, the terms "about" and/or "approximately" may be used in conjunction with numerical values and/or ranges. The term "about" is understood to mean those values near to a recited value. Furthermore, the phrases "less than about [a value]" or "greater than about [a value]" should be understood in view of the definition of the term "about" provided herein. The terms "about" and "approximately" may be used interchangeably.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

The term "a" or "an" refers to one or more of that entity; for example, "a androgen receptor modulator" refers to one or more androgen receptor modulators or at least one androgen receptor modulator. As such, the terms "a" (or "an"), "one or more" and "at least one" are used interchangeably herein. In addition, reference to "an inhibitor" by the indefinite article "a" or "an" does not exclude the possibility that more than one of the inhibitors is present, unless the context clearly requires that there is one and only one of the inhibitors.

As used herein, the verb "comprise" as is used in this description and in the claims and its conjugations are used in its non-limiting sense to mean that items following the word are included, but items not specifically mentioned are not excluded. The present invention may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The term "pharmaceutically acceptable salts" includes both acid and base addition salts. Pharmaceutically acceptable salts include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Those skilled in the art will further recognize that acid addition salts may be prepared by reaction of the compounds with the appropriate inorganic or organic acid via any of a number of known methods.

As used herein, "solvate" means a complex formed by solvation (the combination of solvent molecules with molecules or ions of the active agent of the present invention), or an aggregate that consists of a solute ion or molecule (the active agent of the present invention) with one or more solvent molecules. In the present invention, the preferred solvate is hydrate. Examples of hydrate include, but are not limited to, hemihydrate, monohydrate, dihydrate, trihydrate, hexahydrate, etc. It should be understood by one of ordinary skill in the art that the pharmaceutically acceptable salt of the present compound may also exist in a solvate form (solvate salt). The solvate is typically formed via hydration which is either part of the preparation of the present compound or through natural absorption of moisture by the anhydrous compound of the present invention. Solvates including hydrates may be consisting in stoichiometric ratios, for example, with two, three, four salt molecules per solvate or per hydrate molecule. Another possibility, for example, that two salt molecules are stoichiometric related to three, five, seven solvent or hydrate molecules. Solvents used for crystallization, such as alcohols, especially methanol and ethanol; aldehydes; ketones, especially acetone; esters, e.g. ethyl acetate; may be embedded in the crystal grating. Preferred are pharmaceutically acceptable solvents.

The term "treating" means one or more of relieving, alleviating, delaying, reducing, improving, or managing at least one symptom of a condition in a subject. The term "treating" may also mean one or more of arresting, delaying the onset (i.e., the period prior to clinical manifestation of the condition) or reducing the risk of developing or worsening a condition.

An "effective amount" means the amount of a formulation according to the invention that, when administered to a patient for treating a state, disorder or condition is sufficient to effect such treatment. The "effective amount" will vary depending on the active ingredient, the state, disorder, or condition to be treated and its severity, and the age, weight, physical condition and responsiveness of the mammal to be treated.

The term "therapeutically effective" applied to dose or amount refers to that quantity of a compound or pharmaceutical formulation that is sufficient to result in a desired clinical benefit after administration to a patient in need thereof.

As used herein, a "subject" can be a human, non-human primate, mammal, rat, mouse, cow, horse, pig, sheep, goat, dog, cat and the like. The subject can be suspected of having or at risk for having a cancer, such as prostate cancer, breast cancer, ovarian cancer, salivary gland carcinoma, or endometrial cancer, or suspected of having or at risk for having acne, hirsutism, alopecia, benign prostatic hyperplasia, ovarian cysts, polycystic ovary disease, precocious puberty, spinal and bulbar muscular atrophy, or age-related macular degeneration. Diagnostic methods for various cancers, such as prostate cancer, breast cancer, ovarian cancer, bladder cancer, pancreatic cancer, hepatocellular cancer, salivary gland carcinoma, or endometrial cancer, and diagnostic methods for acne, hirsutism, alopecia, benign prostatic hyperplasia, ovarian cysts, polycystic ovary disease, precocious puberty, spinal and bulbar muscular atrophy, or age-related macular degeneration and the clinical delineation of cancer, such as prostate cancer, breast cancer, ovarian cancer, bladder cancer, pancreatic cancer, hepatocellular cancer, salivary gland carcinoma, or endometrial cancer, diagnoses and the clinical delineation of acne, hirsutism, alopecia, benign prostatic hyperplasia, ovarian cysts, polycystic ovary disease, precocious puberty, spinal and bulbar muscular atrophy, or age-related macular degeneration are known to those of ordinary skill in the art.

"Mammal" includes humans and both domestic animals such as laboratory animals (e.g., mice, rats, monkeys, dogs, etc.) and household pets (e.g., cats, dogs, swine, cattle, sheep, goats, horses, rabbits), and non-domestic animals such as wildlife and the like.

All weight percentages (i.e., "% by weight" and "wt. %" and w/w) referenced herein, unless otherwise indicated, are measured relative to the total weight of the pharmaceutical composition.

As used herein, "substantially" or "substantial" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking, the nearness of completion will be so as to have the same overall result as if absolute and total completion were obtained. The use of "substantially" is equally applicable when used in a negative connotation to refer to the complete or near complete lack of action, characteristic, property, state, structure, item, or result. For example, a composition that is "substantially free of" other active agents would either completely lack other active agents, or so nearly completely lack other active agents that the effect would be the same as if it completely lacked other active agents. In other words, a composition that is "substantially free of" an ingredient or element or another active agent may still contain such an item as long as there is no measurable effect thereof.

Polymorphism can be characterized as the ability of a compound to crystallize into different crystal forms, while maintaining the same chemical formula. A crystalline polymorph of a given drug substance is chemically identical to any other crystalline polymorph of that drug substance in containing the same atoms bonded to one another in the same way, but differs in its crystal forms, which can affect one or more physical properties, such as stability, solubility, melting point, bulk density, flow properties, bioavailability, etc.

As used herein, the term "solid dispersion" is a system in a solid state (as opposed to a liquid or gaseous state) comprising at least two components, wherein one component is dispersed more or less evenly throughout the other component or components (homogenous mix). Generally, a solid dispersion formulation of a therapeutically active agent(s) refers to a dispersion mixture of the therapeutically active agent(s) in an inert carrier. Inert carriers can be a crystalline carrier (such as sugars), a polymeric carrier (such as HPMCAS), or a mixture of surfactants and polymers. Typically, a solid dispersion of a therapeutically active agent increases the surface area of the therapeutically active agent and enhances drug solubility and/or dissolution rate.

The following description includes information that may be useful in understanding the present invention. It is not an admission that any of the information provided herein is prior art or relevant to the presently claimed inventions, or that any publication specifically or implicitly referenced is prior art.

Solid Forms of Compound I

In one embodiment, the present disclosure relates to solid forms of Compound I or a pharmaceutically acceptable salt, solvate, or solvate salt thereof. In one embodiment, the solid form is for Compound I (not a salt, not a solvate, not a solvate salt). In one embodiment, the solid form is for a pharmaceutically acceptable salt of Compound I. In one embodiment, the solid form is for a pharmaceutically acceptable solvate of Compound I. In one embodiment, the solid form is for a pharmaceutically acceptable solvate salt of Compound I. In one embodiment the solid form is amorphous or crystalline form.

In another embodiment, the amorphous form of Compound I or a pharmaceutically acceptable salt, solvate, or solvate salt thereof is in a pharmaceutical composition. In a specific embodiment, the pharmaceutical composition comprises Compound I in a solid dispersion.

In one embodiment, the solid form of Compound I is crystalline Form A. In one embodiment, the solid form of Compound I is amorphous form. In one embodiment, the solid form of Compound I is Material B. In one embodiment, the solid form of Compound I is Material C. In one embodiment, the solid form of Compound I is Material D.

In one embodiment, the present disclosure relates to an isolated solid form of Compound I or a pharmaceutically acceptable salt, solvate, or solvate salt thereof. In one embodiment, the isolated solid form is an isolated crystalline form of Compound I or a pharmaceutically acceptable salt, solvate, or solvate salt thereof. In one embodiment, the isolated solid form is an isolated crystalline Form A of Compound I. In one embodiment, the isolated solid form is an isolated amorphous form of Compound I or a pharmaceutically acceptable salt, solvate, or solvate salt thereof. In one embodiment, the isolated solid form is an isolated amorphous form of Compound I.

In one embodiment, the solid form of Compound I or a pharmaceutically acceptable salt, solvate, or solvate salt thereof has a purity of at least about 75%, at least about 80%, at least about 85%, at least about 90%, at least about 95%, at least about 97%, at least about 98%, or at least about 99%. In one embodiment, the solid form of Compound I or a pharmaceutically acceptable salt, solvate, or solvate salt thereof has a purity of at least about 75%, at least about 80%, at least about 85%, at least about 90%, at least about 95%, at least about 97%, at least about 98%, or at least about 99% with respect to one specific solid form of Compound I or a pharmaceutically acceptable salt, solvate, or solvate salt thereof.

In one embodiment, the solid form of Compound I or a pharmaceutically acceptable salt, solvate, or solvate salt thereof has a purity of at least about 99.9%, about 99.8%, about 99.7%, about 99.6%, about 99.5%, about 99.4%, about 99.3%, about 99.2%, about 99.1%, about 99.0%, about 98%, about 97%, about 96%, about 95%, about 94%, about 93%, about 92%, about 91%, or about 90%. In one embodiment, the solid form of Compound I or a pharmaceutically acceptable salt, solvate, or solvate salt thereof has a purity of at least about 99.9%, about 99.8%, about 99.7%, about 99.6%, about 99.5%, about 99.4%, about 99.3%, about 99.2%, about 99.1%, about 99.0%, about 98%, about 97%, about 96%, about 95%, about 94%, about 93%, about 92%, about 91%, or about 90% with respect to one specific solid form of Compound I or a pharmaceutically acceptable salt, solvate, or solvate salt thereof.

In one embodiment, the solid form of Compound I or a pharmaceutically acceptable salt, solvate, or solvate salt thereof has a purity of about 75% to about 99%. In one embodiment, the solid form of Compound I or a pharmaceutically acceptable salt, solvate, or solvate salt thereof has a purity of about 80% to about 99%. In one embodiment, the solid form of Compound I or a pharmaceutically acceptable salt, solvate, or solvate salt thereof has a purity of about 85% to about 99%. In one embodiment, the solid form of Compound I or a pharmaceutically acceptable salt, solvate, or solvate salt thereof has a purity of about 90% to about 99%. In one embodiment, the solid form of Compound I or a pharmaceutically acceptable salt, solvate, or solvate salt thereof has a purity of about 95% to about 99%.

In one embodiment, the solid form of Compound I or a pharmaceutically acceptable salt, solvate, or solvate salt thereof has a purity of about 75% to about 99% with respect to one specific solid form of Compound I or a pharmaceutically acceptable salt, solvate, or solvate salt thereof. In one embodiment, the solid form of Compound I or a pharmaceutically acceptable salt, solvate, or solvate salt thereof has a purity of about 80% to about 99% with respect to one specific solid form of Compound I or a pharmaceutically acceptable salt, solvate, or solvate salt thereof. In one embodiment, the solid form of Compound I or a pharmaceutically acceptable salt, solvate, or solvate salt thereof has a purity of about 85% to about 99% with respect to one specific solid form of Compound I or a pharmaceutically acceptable salt, solvate, or solvate salt thereof. In one embodiment, the solid form of Compound I or a pharmaceutically acceptable salt, solvate, or solvate salt thereof has a purity of about 90% to about 99% with respect to one specific solid form of Compound I or a pharmaceutically acceptable salt, solvate, or solvate salt thereof. In one embodiment, the solid form of Compound I or a pharmaceutically acceptable salt, solvate, or solvate salt thereof has a purity of about 95% to about 99% with respect to one specific solid form of Compound I or a pharmaceutically acceptable salt, solvate, or solvate salt thereof.

In one embodiment, the specific solid form of Compound I or a pharmaceutically acceptable salt, solvate, or solvate salt thereof with high purity is crystalline Form A of Compound I. In one embodiment, the specific solid form of Compound I or a pharmaceutically acceptable salt, solvate, or solvate salt thereof with high purity is an amorphous form of Compound I.

In one embodiment, the present disclosure relates to solid forms of Compound I or a pharmaceutically acceptable salt, solvate, or solvate salt thereof, wherein the solid form comprises one or more solid forms of Compound I or a pharmaceutically acceptable salt, solvate, or solvate salt thereof. In one embodiment, the solid form of the present disclosure comprises one or more forms selected from the group consisting of: crystalline Form A of Compound I, amorphous form of Compound I, Material B of Compound I, Material C of Compound I, and Material D of Compound I.

Crystalline Form of Compound I

In one embodiment, the present disclosure relates to a crystalline form of Compound I or a pharmaceutically acceptable salt, solvate, or solvate salt thereof. In one embodiment, the present disclosure relates to an anhydrous or non-solvated crystalline form of Compound I or a pharmaceutically acceptable salt thereof. In one embodiment, the present disclosure relates to an anhydrous or non-solvated crystalline form of Compound I (not a salt). In one embodiment, the present disclosure relates to a crystalline form of Compound I (not a salt). In one embodiment, the present disclosure relates to a crystalline form of Compound I, which is Form A.

In one embodiment, the crystalline forms are characterized by the interlattice plane intervals determined by an X-ray powder diffraction (XRPD) pattern. The spectrum of XRPD is typically represented by a diagram plotting the intensity of the peaks versus the location of the peaks, i.e., diffraction angle 2θ (two-theta) in degrees. The intensities are often given in parenthesis with the following abbreviations: very strong=vst; strong=st; medium=m; weak=w; and very weak=vw. The characteristic peaks of a given XRPD can be selected according to the peak locations and their relative intensity to conveniently distinguish this crystalline structure from others. The % intensity of the peaks relative to the most intense peak may be represented as I/Io.

Those skilled in the art recognize that the measurements of the XRPD peak locations and/or intensity for a given crystalline form of the same compound will vary within a margin of error. The values of degree 2θ allow appropriate error margins. Typically, the error margins are represented by "±". For example, the degree 2θ of about 17.48±0.2" denotes a range from about 17.46 to 17.50 degree 2θ. Depending on the sample preparation techniques, the calibration techniques applied to the instruments, human operational variation, and etc., those skilled in the art recognize that the appropriate error of margins for a XRPD can be about ±0.7; ±0.6; ±0.5; ±0.4; ±0.3; ±0.2; ±0.1; ±0.05; or less.

Additional details of the methods and equipment used for the XRPD analysis are described in the Examples section.

In one embodiment, the crystalline forms are characterized by Differential Scanning Calorimetry (DSC). The DSC thermogram is typically expressed by a diagram plotting the normalized heat flow in units of Watts/gram ("W/g") versus the measured sample temperature in degree Celsius. The DSC thermogram is usually evaluated for extrapolated onset and end (outset) temperatures, peak temperature, and heat of fusion. A peak characteristic value of a DSC thermogram is often used as the characteristic peak to distinguish this crystalline structure from others.

Those skilled in the art recognize that the measurements of the DSC thermogram for a given crystalline form of the same compound will vary within a margin of error. The values of a single peak characteristic value, expressed in degree Celsius, allow appropriate error margins. Typically, the error margins are represented by "±". For example, the single peak characteristic value of about "17.48±0.2" denotes a range from about 17.46 to 17.50. Depending on the sample preparation techniques, the calibration techniques applied to the instruments, human operational variations, and etc., those skilled in the art recognize that the appropriate error of margins for a single peak characteristic value can be ±2.5; ±2.0; ±1.5; ±1.0; ±0.5; or less.

Additional details of the methods and equipment used for the DSC thermogram analysis are described in the Examples section.

In one embodiment, the crystalline forms are characterized by Dynamic Vapor Sorption (DVS). The DVS profile is typically expressed by a diagram plotting the sample relative humidity (RH) versus the change in mass (%). The DVS profile provides information on hygroscopicity of the crystalline form at different RH conditions.

Additional details of the methods and equipment used for DVS are described in the Examples section.

In one embodiment, the present disclosure relates to Form A, which is a crystalline form of Compound I that is anhydrous or non-solvated. In one embodiment, Form A is more stable than other crystalline forms of Compound I, pharmaceutically acceptable salt, solvate, or solvate salt thereof. In one embodiment, Form A exhibits high stability. In one embodiment, Form A is the most thermodynamically stable form.

In one embodiment, Form A of crystalline form of Compound I may comprise of a mixture of one or more forms of polymorphs of Compound I. In some embodiments, the crystalline form of Compound I may comprise of substantially pure form of one polymorph type. In one embodiment, the crystalline form of Compound I may comprise of over about 99.9%, about 99.8%, about 99.7%, about 99.6%, about 99.5%, about 99.4%, about 99.3%, about 99.2%, about 99.10%, or about 99.0% of Form A. In another embodiment, the crystalline form of Compound I may comprise over about 99%, 98%, 97%, 96%, 95%, 94%, 93%, 92%, 91%, or 90% of Form A. In some embodiments, the crystalline form of Compound I may comprise over about 90%, 85%, 80%, 75%, 70%, 65%, 60%, 55%, 50%, 45%, or 40% of Form A.

In one embodiment, crystalline Form A of Compound I exhibits an XRPD pattern comprising peaks at about 17.48, 20.78, and 21.80 degrees two-theta with the margin of error of about ±0.5; about ±0.4; about ±0.3; about ±0.2; about ±0.1; about ±0.05; or less. In another embodiment, the XRPD of the crystalline Form A of Compound I further comprises peaks at about 5.19 and 12.94 degrees two-theta with the margin of error of about ±0.5; about ±0.4; about ±0.3; about ±0.2; about ±0.1; about ±0.05; or less. In further embodiment, the crystalline Form A of Compound I further comprises at least two peaks selected from about 17.80, 18.74, 19.57, 22.59, 25.28, or 29.95 degrees two-theta with the margin of error of about ±0.5; about ±0.4; about ±0.3; about ±0.2; about ±0.1; about ±0.05; or less. In further embodiment, the crystalline Form A of Compound I further comprises at least three peaks selected from about 17.80, 18.74, 19.57, 22.59, 25.28, or 29.95 degrees two-theta with the margin of error of about ±0.5; about ±0.4; about ±0.3; about ±0.2; about ±0.1; about ±0.05; or less. In further embodiment, the crystalline Form A of Compound I further comprises at least four peaks selected from about 17.80, 18.74, 19.57, 22.59, 25.28, or 29.95 degrees two-theta with the margin of error of about ±0.5; about ±0.4; about ±0.3; about ±0.2; about ±0.1; about ±0.05; or less. In further embodiment, the crystalline Form A of Compound I further comprises at least five peaks selected from about 17.80, 18.74, 19.57, 22.59, 25.28, or 29.95 degrees two-theta with the margin of error of about ±0.5; about ±0.4; about ±0.3; about ±0.2; about ±0.1; about ±0.05; or less. In further embodiment, the crystalline Form A of Compound I further comprises peaks at about 17.80, 18.74, 19.57, 22.59, 25.28, and 29.95 degrees two-theta with the margin of error of about ±0.5; about ±0.4; about ±0.3; about ±0.2; about ±0.1; about ±0.05; or less.

In one embodiment, crystalline Form A of Compound I exhibits an XRPD pattern comprising peaks at about 17.48±0.2, 20.78±0.2, and 21.80±0.2 degrees two-theta. In one embodiment, crystalline Form A of Compound I exhibits an XRPD pattern comprising peaks having intensity of at least 50% at about 17.48±0.2, 20.78±0.2, and 21.80±0.2 degrees two-theta. In one embodiment, crystalline Form A of Compound I exhibits an XRPD pattern comprising peaks having intensity of at least 60% at about 17.48±0.2, 20.78±0.2, and 21.80±0.2 degrees two-theta. In one embodiment, crystalline Form A of Compound I exhibits an XRPD pattern comprising peaks having intensity of at least 65% at about 17.48±0.2, 20.78±0.2, and 21.80±0.2 degrees two-theta.

In one embodiment, crystalline Form A of Compound I exhibits an XRPD pattern comprising peaks at about 5.19±0.2 and 12.94±0.2 degrees two-theta. In one embodiment, crystalline Form A of Compound I exhibits an XRPD pattern comprising peaks having intensity of at least 30% at about 5.19±0.2 and 12.94±0.2 degrees two-theta. In one embodiment, crystalline Form A of Compound I exhibits an XRPD pattern comprising peaks having intensity of at least 35% at about 5.19±0.2 and 12.94±0.2 degrees two-theta. In one embodiment, crystalline Form A of Compound I exhibits an XRPD pattern comprising peaks having intensity of at least 40% at about 5.19±0.2 and 12.94±0.2 degrees two-theta. In one embodiment, crystalline Form A of Compound I exhibits an XRPD pattern comprising peaks having intensity of at least 35% at about 5.19±0.2, 12.94±0.2, 17.48±0.2, 20.78±0.2, and 21.80±0.2 degrees two-theta.

In one embodiment, crystalline Form A of Compound I exhibits an XRPD pattern comprising at least two peaks selected from about 17.80±0.2, 18.74±0.2, 19.57±0.2, 22.59±0.2, 25.28±0.2, or 29.95±0.2 degrees two-theta. In one embodiment, crystalline Form A of Compound I exhibits an XRPD pattern comprising peaks at about 17.80±0.2, 18.74±0.2, 19.57±0.2, 22.59±0.2, 25.28±0.2, and 29.95±0.2 degrees two-theta. In one embodiment, crystalline Form A of Compound I exhibits an XRPD pattern comprising peaks having intensity of at least 15% at about 17.80±0.2, 18.74±0.2, 19.57±0.2, 22.59±0.2, 25.28±0.2, and 29.95±0.2 degrees two-theta. In one embodiment, crystalline Form A of Compound I exhibits an XRPD pattern comprising peaks having intensity of at least 20% at about 17.80±0.2, 18.74±0.2, 19.57±0.2, 22.59±0.2, 25.28±0.2, and 29.95±0.2 degrees two-theta.

In one embodiment, crystalline Form A of Compound I exhibits an XRPD pattern comprising peaks having intensity of at least 30% at about 5.19±0.2, 12.94±0.2, 17.48±0.2, 17.80±0.2, 18.74±0.2, 20.78±0.2, and 21.80±0.2 degrees two-theta. In one embodiment, crystalline Form A of Compound I exhibits an XRPD pattern comprising peaks having intensity of at least 35% at about 5.19±0.2, 12.94±0.2, 17.48±0.2, 18.74±0.2, 20.78±0.2, and 21.80±0.2 degrees two-theta.

In one embodiment, the crystalline Form A of Compound exhibits an XRPD comprising peaks shown in Table 1A below. In one embodiment, the crystalline Form A of Compound I exhibits an XRPD comprising peaks shown in Table 1B below.

TABLE 1A

XRPD Table of Form A of Compound I

| °2θ | d space (Å) | Intensity (%) |
|---|---|---|
| 5.19 ± 0.20 | 17.013 ± 0.655 | 41 |
| 9.60 ± 0.20 | 9.206 ± 0.191 | 8 |
| 10.42 ± 0.20 | 8.483 ± 0.162 | 6 |
| 10.89 ± 0.20 | 8.118 ± 0.149 | 12 |
| 12.38 ± 0.20 | 7.144 ± 0.115 | 6 |
| 12.94 ± 0.20 | 6.836 ± 0.105 | 51 |
| 13.17 ± 0.20 | 6.715 ± 0.101 | 6 |
| 13.52 ± 0.20 | 6.544 ± 0.096 | 15 |
| 15.40 ± 0.20 | 5.749 ± 0.074 | 13 |
| 15.64 ± 0.20 | 5.661 ± 0.072 | 7 |
| 15.90 ± 0.20 | 5.569 ± 0.070 | 5 |
| 16.17 ± 0.20 | 5.477 ± 0.067 | 13 |
| 16.75 ± 0.20 | 5.289 ± 0.063 | 7 |
| 17.01 ± 0.20 | 5.208 ± 0.061 | 8 |
| 17.48 ± 0.20 | 5.069 ± 0.058 | 100 |
| 17.80 ± 0.20 | 4.979 ± 0.055 | 32 |
| 18.74 ± 0.20 | 4.731 ± 0.050 | 38 |
| 19.57 ± 0.20 | 4.532 ± 0.046 | 23 |
| 20.20 ± 0.20 | 4.392 ± 0.043 | 9 |
| 20.78 ± 0.20 | 4.271 ± 0.041 | 70 |
| 21.80 ± 0.20 | 4.074 ± 0.037 | 73 |
| 22.59 ± 0.20 | 3.933 ± 0.034 | 23 |
| 22.99 ± 0.20 | 3.865 ± 0.033 | 18 |
| 23.29 ± 0.20 | 3.816 ± 0.032 | 14 |
| 23.53 ± 0.20 | 3.778 ± 0.032 | 7 |
| 24.91 ± 0.20 | 3.572 ± 0.028 | 10 |
| 25.28 ± 0.20 | 3.528 ± 0.027 | 23 |
| 25.82 ± 0.20 | 3.448 ± 0.026 | 5 |

TABLE 1A-continued

XRPD Table of Form A of Compound I

| °2θ | d space (Å) | Intensity (%) |
|---|---|---|
| 26.21 ± 0.20 | 3.397 ± 0.025 | 9 |
| 26.57 ± 0.20 | 3.352 ± 0.025 | 19 |
| 27.29 ± 0.20 | 3.265 ± 0.023 | 12 |
| 27.83 ± 0.20 | 3.203 ± 0.023 | 14 |
| 28.06 ± 0.20 | 3.177 ± 0.022 | 13 |
| 28.68 ± 0.20 | 3.110 ± 0.021 | 4 |
| 29.09 ± 0.20 | 3.067 ± 0.021 | 5 |
| 29.59 ± 0.20 | 3.016 ± 0.020 | 10 |
| 29.95 ± 0.20 | 2.981 ± 0.019 | 25 |

TABLE 1B

XRPD Table of Form A of Compound I

| °2θ | d space (Å) | Intensity (%) |
|---|---|---|
| 5.19 ± 0.20 | 17.013 ± 0.655 | 41 |
| 12.94 ± 0.20 | 6.836 ± 0.105 | 51 |
| 17.48 ± 0.20 | 5.069 ± 0.058 | 100 |
| 17.80 ± 0.20 | 4.979 ± 0.055 | 32 |
| 18.74 ± 0.20 | 4.731 ± 0.050 | 38 |
| 19.57 ± 0.20 | 4.532 ± 0.046 | 23 |
| 20.78 ± 0.20 | 4.271 ± 0.041 | 70 |
| 21.80 ± 0.20 | 4.074 ± 0.037 | 73 |
| 22.59 ± 0.20 | 3.933 ± 0.034 | 23 |
| 25.28 ± 0.20 | 3.520 ± 0.027 | 23 |
| 29.95 ± 0.20 | 2.981 ± 0.019 | 25 |

In one specific embodiment, the crystalline Form A of Compound I exhibits an XRPD pattern that is substantially similar to FIG. 1. In one embodiment, the XRPD spectrum presented in FIG. 1 contains small amount of NaCl. In one embodiment, the XRPD peaks at 27.3±0.2 and at 31.7±0.2 degrees two-theta in FIG. 1 is attributed to the presence of small amount of NaCl. In one embodiment, the XRPD peaks at 27.3±0.2 degrees two-theta in Table 1A is attributed to the presence of small amount of NaCl.

In one embodiment, the crystalline Form A of Compound I exhibits an XRPD pattern that is substantially similar to FIG. 1 provided that peaks at 27.3±0.2 and at 31.7±0.2 degrees two-theta are excluded as not being part of the characterization of Form A. In one embodiment, the crystalline Form A of Compound I exhibits an XRPD pattern comprising peaks shown in Table 1A, provided that peaks at 27.3±0.2 degrees two-theta are excluded as not being part of the characterization of Form A.

Figure 2:
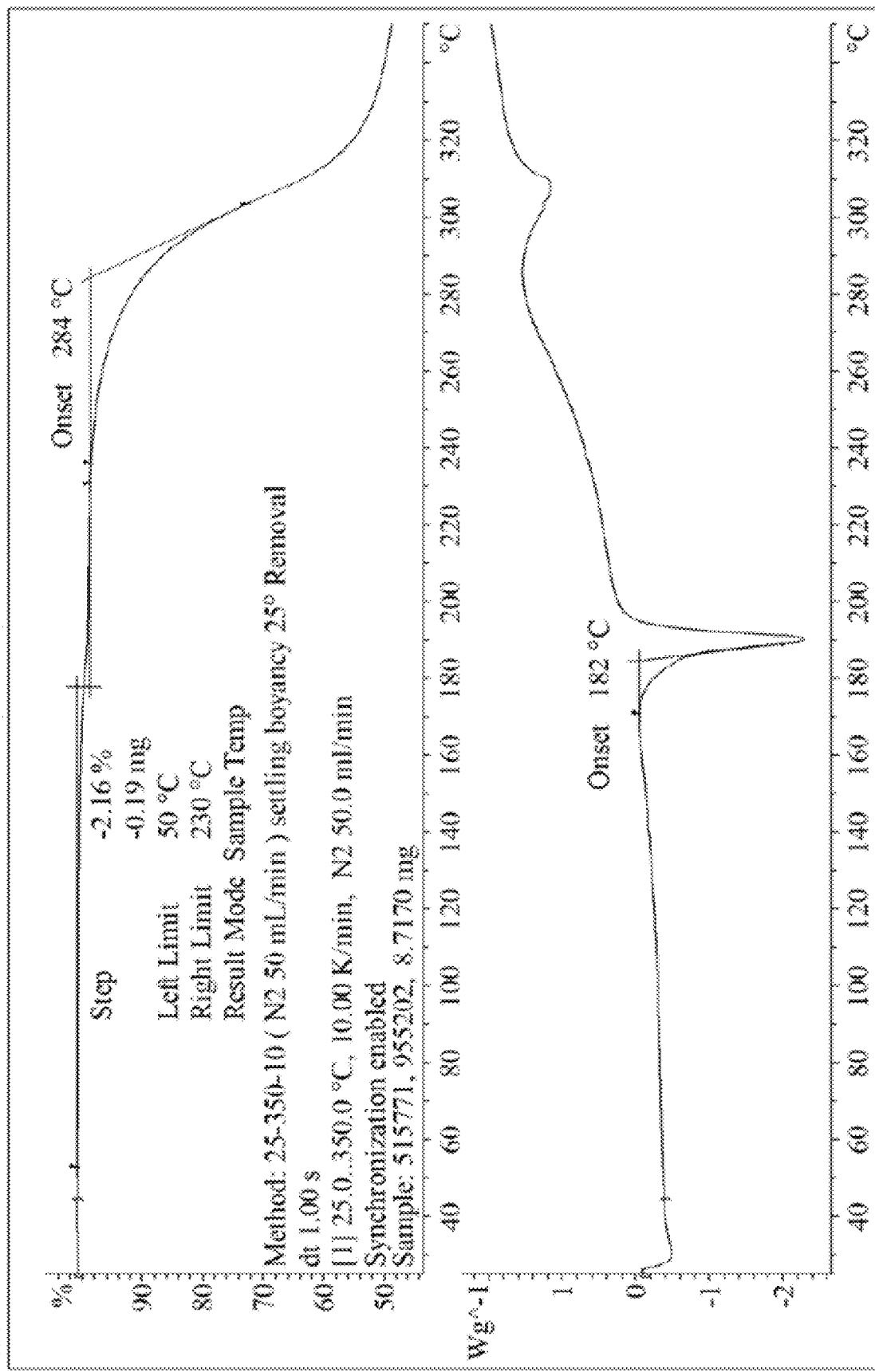
FIG. 2 shows thermogravimetric analysis (TGA)/differential scanning calorimetry (DSC) thermograms of crystalline Form A of Compound I.

In one embodiment, the crystalline Form A of Compound I exhibits a TGA thermogram substantially similar to FIG. 2 (top). In one embodiment, crystalline Form A of Compound I shows change in the slope of a TGA thermogram starting at about 284° C. (onset). Without bound to any theory, this change in the slope of the TGA thermogram is likely associated with the decomposition of crystalline Form A of Compound I.

In one embodiment, the crystalline Form A of Compound I exhibits a DSC thermogram comprising an endotherm peak at about 182° C. (onset) with the error of margin of about ±2.5; about ±2.0; about ±1.5; about ±1.0; about ±0.5; or less. In one embodiment, the crystalline Form A of Compound I exhibits a DSC thermogram comprising an endotherm peak at about 185° C. (peak) with the error of margin of about ±2.5; about ±2.0; about ±1.5; about ±1.0; about ±0.5; or less. In one embodiment, the crystalline Form A of Compound I exhibits a DSC thermogram that is substantially similar to FIG. 2 (bottom).

In one embodiment, crystalline Form A of Compound I can be obtained as a suitable single crystal. In one embodiment, single crystals of Form A has a crystal system that is monoclinic and the space group is P2$_1$/c. In one embodiment, the cell parameters and the calculated volume of the single crystals of Form A are about: a=17.5550±0.0002 Å, b=10.96169±0.00013 Å, c=13.7961±0.0002 Å, α=90°, β=104.5717±0.0015°, γ=90°, and V=2569.40±0.06 Å$^3$. In one embodiment, single crystals of Form A has a density of about 1.384 g/cm$^3$.

Amorphous Form of Compound I

In one embodiment, the present disclosure relates to solid forms of Compound I or a pharmaceutically acceptable salt, solvate, or solvate salt thereof. In one embodiment, the present disclosure relates to an amorphous form of Compound I or a pharmaceutically acceptable salt, solvate, or solvate salt thereof. In one embodiment, the present disclosure relates to an amorphous form of anhydrous or non-solvated Compound I or a pharmaceutically acceptable salt thereof. In one embodiment, the present disclosure relates to an amorphous form of anhydrous or non-solvated Compound I (not a salt). In one embodiment, the present disclosure relates to an amorphous form of Compound I (not a salt, not a solvate, not a solvate salt).

In another embodiment, the amorphous form of Compound I or a pharmaceutically acceptable salt, solvate, or solvate salt thereof is in a pharmaceutical composition. In a specific embodiment, the pharmaceutical composition comprises Compound I in a solid dispersion.

Figure 6:
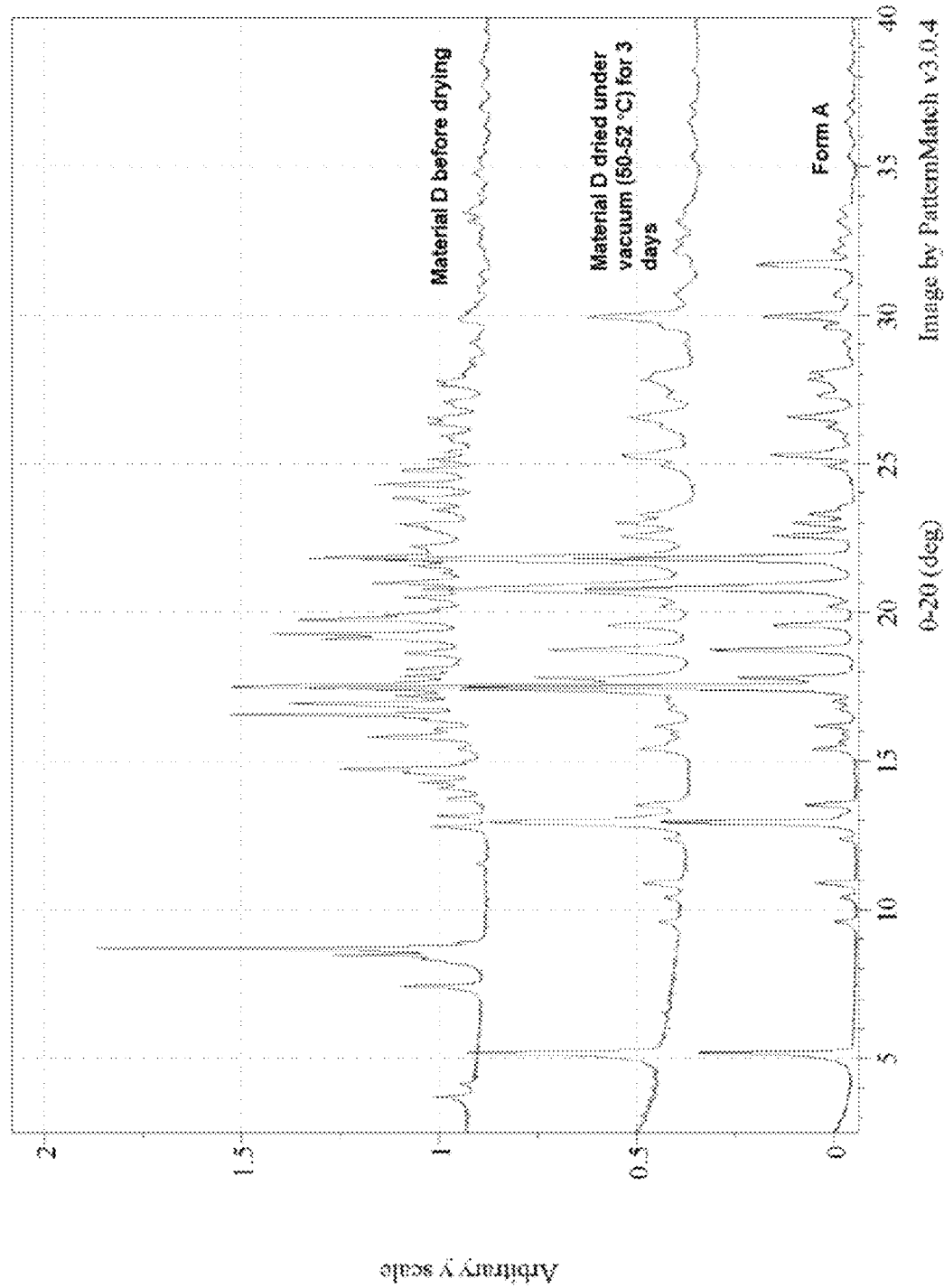
FIG. 6 shows XRPD spectrum overlay of Compound I in crystalline Form A, Material D before drying, and Material D after drying under vacuum at 50-52° C. for 3 days.

In one embodiment, the amorphous form of Compound I exhibits an XRPD pattern that is substantially similar to FIG. 6, third spectrum from the bottom, excluding peaks attributed to the presence of NaCl at about 27 and at about 32 degrees two-theta.

In one embodiment, the amorphous form of Compound I exhibits a glass transition (T$_g$) at about 61° C. with the error of margin of about ±2.5; about ±2.0; about ±1.5; about ±1.0; about ±0.5; or less, as a step change in the reversing heat flow signal. In one embodiment, the glass transition temperature is measured by temperature modulated DSC (TMDSC). In one embodiment, the amorphous form of Compound I exhibits a DSC thermogram comprising an exotherm peak at about 91° C. (peak) with the error of margin of about ±2.5; about ±2.0; about ±1.5; about ±1.0; about ±0.5; or less. In one embodiment, the amorphous form of Compound I exhibits a DSC thermogram comprising an endotherm peak at about 178° C. (onset) with the error of margin of about ±2.5; about ±2.0; about ±1.5; about ±1.0; about ±0.5; or less. In one embodiment, the amorphous form of Compound I exhibits a DSC thermogram that is substantially similar to FIG. 7.

Figure 8:
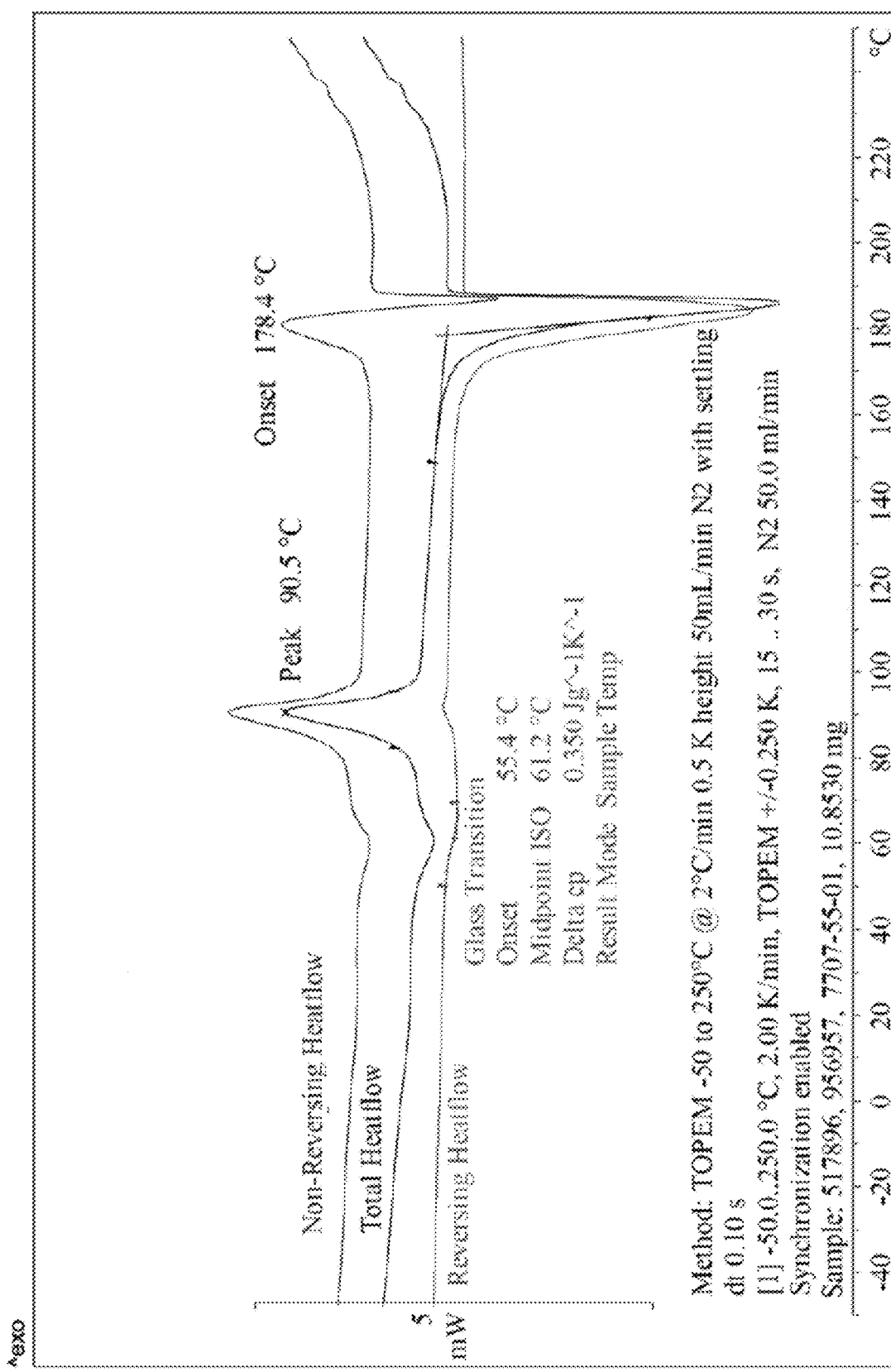
FIG. 8 shows a temperature modulated DSC thermogram of an amorphous form of Compound I.

In one embodiment, the amorphous form of Compound I exhibits a TGA thermogram substantially similar to FIG. 8. In one embodiment, amorphous form of Compound I shows change in the slope of TGA thermogram starting at about 280° C. (onset). Without bound to any theory, this change in the slope of the TGA thermogram is likely associated with the decomposition of the amorphous form of Compound I.

In some embodiments, the amorphous form of Compound I exhibits a glass transition temperature (Tg) in the range of about 60° C. to about 180° C. as measured by differential scanning calorimeter. In some embodiments, the amorphous form of Compound I exhibits a glass transition temperature (Tg) in the range of about 60° C. to about 90° C. as measured by differential scanning calorimeter. In some embodiments, the amorphous form of Compound I exhibits a glass transition temperature (Tg) in the range of about 70° C. to about 80° C. as measured by differential scanning calorimeter. In a specific embodiment, the amorphous form of Compound I is in a pharmaceutical composition, or in a more specific embodiment, a solid dispersion composition.

Figure 13:
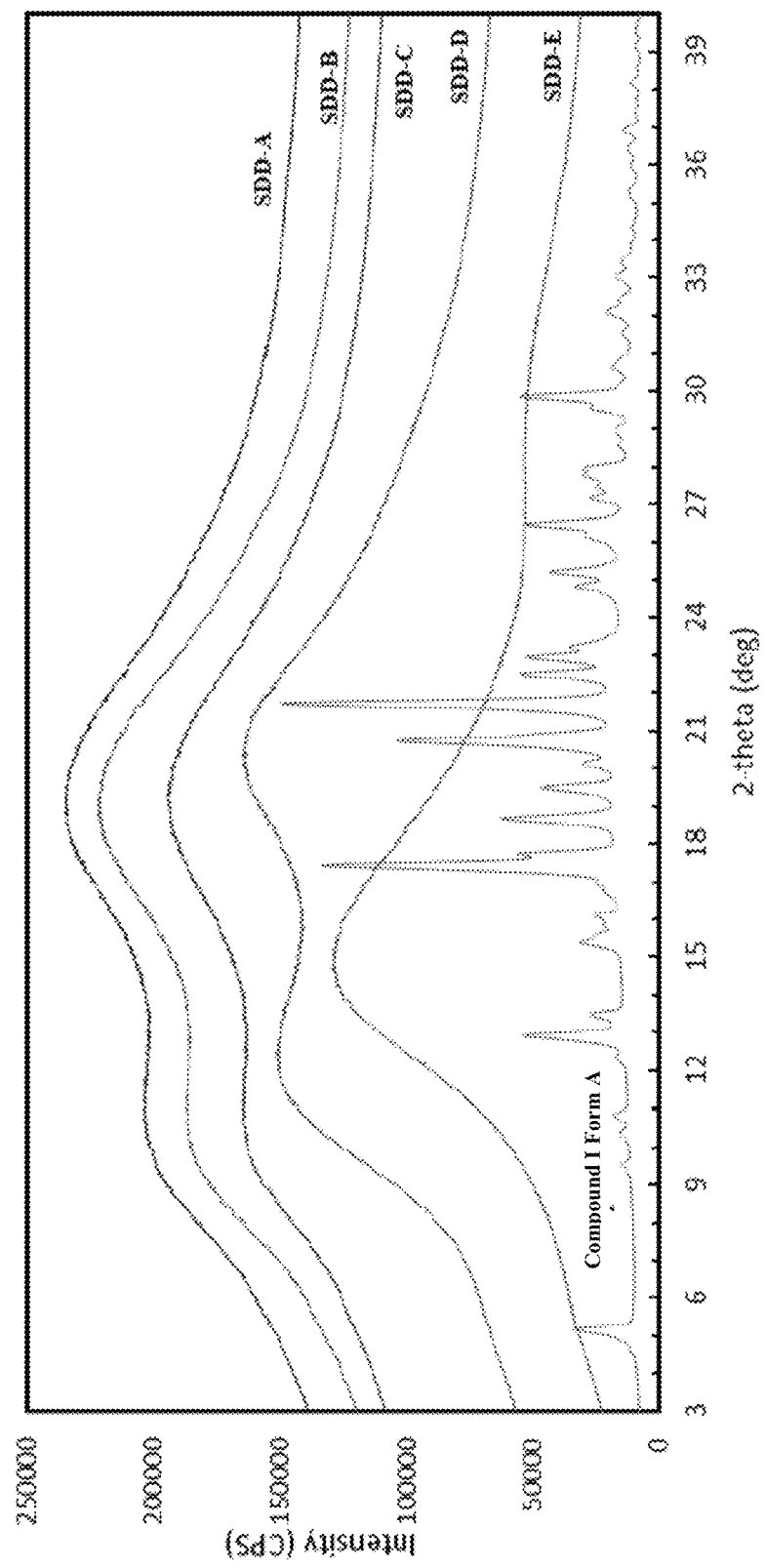
FIG. 13 shows XRPD spectrum overlay of SDD compositions A-E and Form A of Compound I.
Figure 15:
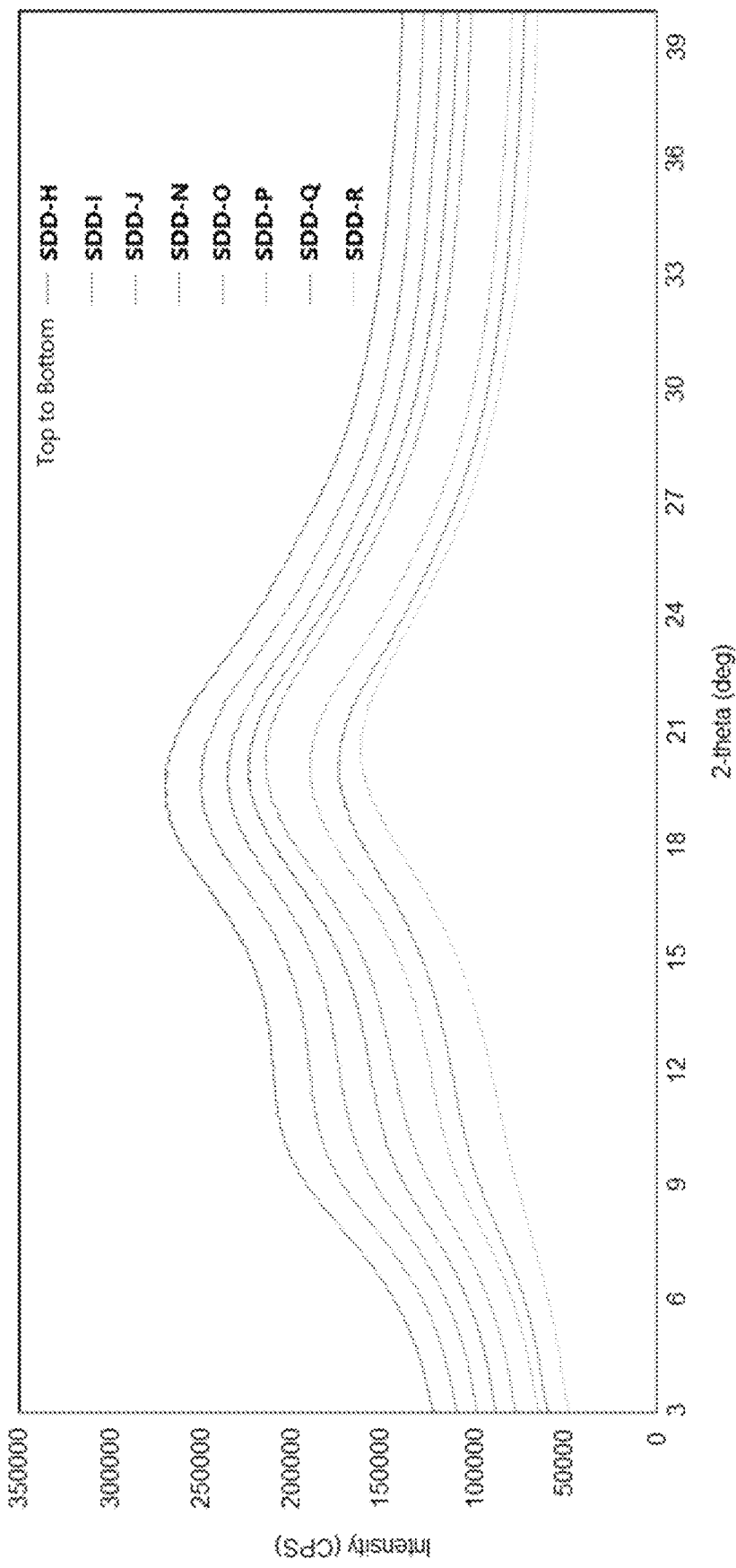
FIG. 15 shows XRPD spectrum overlay of SDD compositions H-J and N-R Compound I.

In some embodiments, the amorphous form of Compound I exhibits an X-ray powder diffraction (XRPD) pattern substantially similar to any one of the patterns shown in FIGS. 13 and 15. In a specific embodiment, the amorphous form of Compound I is in a pharmaceutical composition, or in a more specific embodiment, a solid dispersion composition.

In some embodiments, the amorphous form of Compound I exhibits an XRPD pattern substantially similar to a pattern labeled as SDD-A, SDD-B, SDD-C, SDD-D, or SDD-E in FIG. 13 or a pattern labeled as SDD-H, SDD-I, SDD-J, SDD-N, SDD-O, SDD-O, SDD-P, SDD-Q, or SDD-R in FIG. 15. In some embodiments, the amorphous form of Compound I exhibits an XRPD pattern substantially similar to a pattern labeled as SDD-H, SDD-I, SDD-J, SDD-N, SDD-O, SDD-O, SDD-P, SDD-Q, or SDD-R in FIG. 15. In a specific embodiment, the amorphous form of Compound I is in a pharmaceutical composition, or in a more specific embodiment, a solid dispersion composition.

Figure 14:
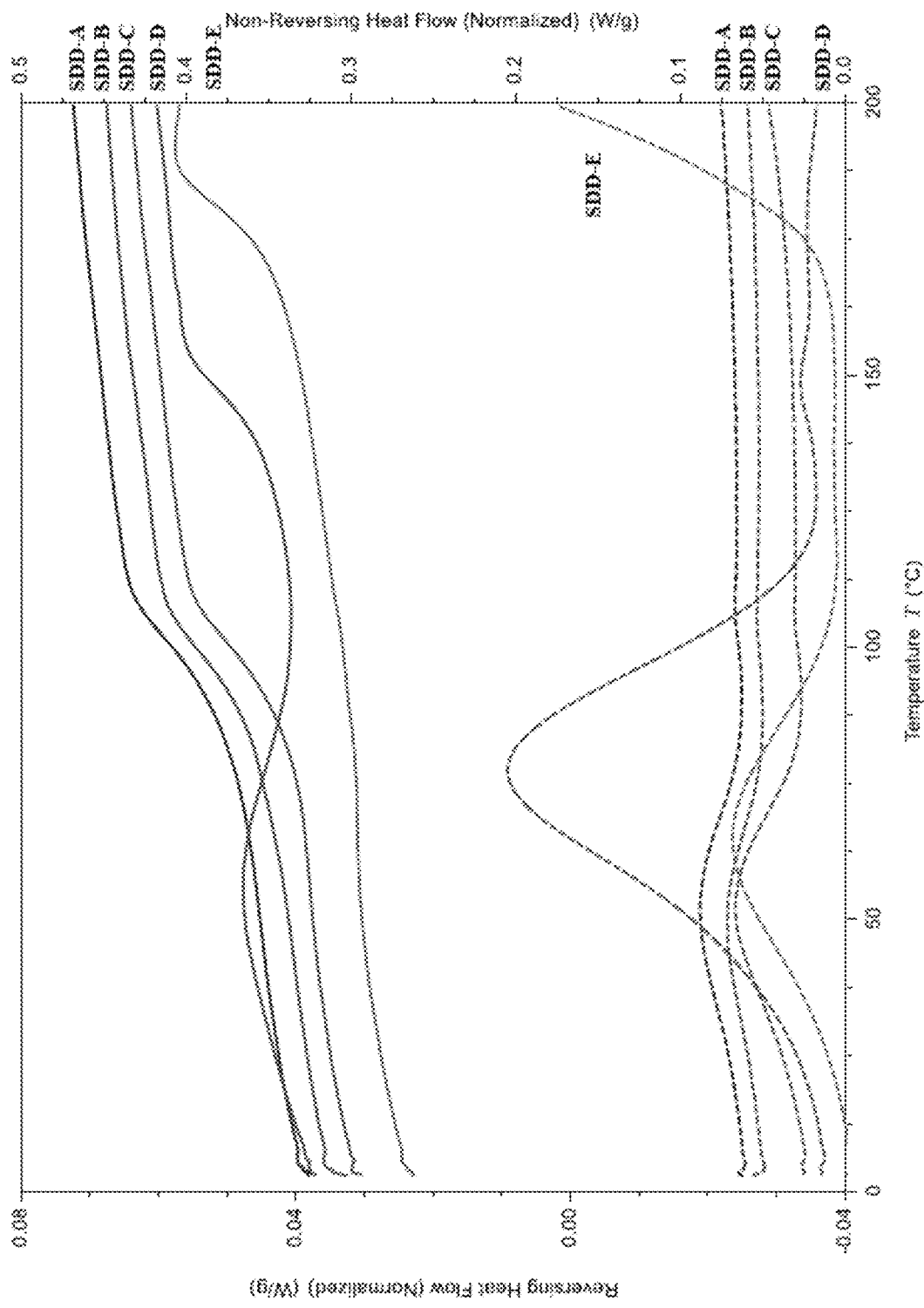
FIG. 14 shows modulated DSC thermogram overlay of SDD compositions A-E of Compound I.

In some embodiments, the amorphous form of Compound I exhibits a modulated differential scanning calorimetry (mDSC) thermogram substantially similar to the thermogram labeled as SDD-A, SDD-B, SDD-C, SDD-D, or SDD-E in FIG. 14. In a specific embodiment, the amorphous form of Compound I is in a pharmaceutical composition, or in a more specific embodiment, a solid dispersion composition.

Pharmaceutical Compositions and Formulations

In another embodiment, the present invention provides a pharmaceutical composition comprising a therapeutically effective amount of a crystalline form of Compound I, or a pharmaceutically acceptable salt, solvate, or solvate salt thereof, as disclosed herein, as the active ingredient, combined with a pharmaceutically acceptable excipient or carrier. In one embodiment, the present invention provides a pharmaceutical composition comprising a therapeutically effective amount of a crystalline Form A of Compound I. In one embodiment, the present invention provides a pharmaceutical composition comprising a therapeutically effective amount of a crystalline Form A of Compound I and a pharmaceutically acceptable excipient or carrier. The excipients are added to the formulation for a variety of purposes.

In one embodiment of the present disclosure, the pharmaceutical composition comprises Compound I or a pharmaceutically acceptable salt, solvate, or solvate salt thereof as a mixture of different forms. In one embodiment, the pharmaceutical composition comprises crystalline Form A of Compound I in about 99.9%, about 99.8%, about 99.7%, about 99.6%, about 99.5%, about 99.4%, about 99.3%, about 99.2%, about 99.1%, or about 99.0% of the total amount of Compound I or a pharmaceutically acceptable salt, solvate, or solvate salt thereof. In one embodiment, the pharmaceutical composition comprises crystalline Form A of Compound I in about 99%, 98%, 97%, 96%, 95%, 94%, 93%, 92%, 91%, or 90% of the total amount of Compound I or a pharmaceutically acceptable salt, solvate, or solvate salt thereof.

In one embodiment, the pharmaceutical composition comprises crystalline Form A of Compound I in about 90%, 85%, 80%, 75%, 70%, 65%, 60%, 55%, 50%, 45%, 40%, 35%, 30%, 25%, or 20% of the total amount of Compound I or a pharmaceutically acceptable salt, solvate, or solvate salt thereof. In one embodiment, the pharmaceutical composition comprises crystalline Form A of Compound I in about 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 18%, or 20% of the total amount of Compound I or a pharmaceutically acceptable salt, solvate, or solvate salt thereof.

In one embodiment, the present invention provides a pharmaceutical composition comprising a therapeutically effective amount of an amorphous form of Compound I, or a pharmaceutically acceptable salt, solvate, or solvate salt thereof, as disclosed herein, as the active ingredient, combined with a pharmaceutically acceptable excipient or carrier.

In one embodiment, the pharmaceutical composition comprises an amorphous form of Compound I in about 99.9%, about 99.8%, about 99.7%, about 99.6%, about 99.5%, about 99.4%, about 99.3%, about 99.2%, about 99.1%, or about 99.0% of the total amount of Compound I or a pharmaceutically acceptable salt, solvate, or solvate salt thereof. In one embodiment, the pharmaceutical composition comprises an amorphous form of Compound I in about 99%, 98%, 97%, 96%, 95%, 94%, 93%, 92%, 91%, or 90% of the total amount of Compound I or a pharmaceutically acceptable salt, solvate, or solvate salt thereof. In one embodiment, the pharmaceutical composition comprises an amorphous form of Compound I in about 90%, 85%, 80%, 75%, 70%, 65%, 60%, 55%, 50%, 45%, 40%, 35%, 30%, 25%, or 20% of the total amount of Compound I or a pharmaceutically acceptable salt, solvate, or solvate salt thereof. In one embodiment, the pharmaceutical composition comprises an amorphous form of Compound I in about 0.1%, 0.2%, 0.3%, 0.4%, 0.5%, 0.6%, 0.7%, 0.8%, 0.9%, 1%, 1.5%, 2%, 2.5%, 3% 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 18%, or 20% of the total amount of Compound I or a pharmaceutically acceptable salt, solvate, or solvate salt thereof.

In one embodiment of the present disclosure, the pharmaceutical composition comprises a mixture of a crystalline form and an amorphous form of Compound I or a pharmaceutically acceptable salt, solvate, or solvate salt thereof. In one embodiment, the mixture comprises an amorphous form of Compound I in about 99%, 98%, 97%, 96%, 95%, 94%, 93%, 92%, 91%, or 90% and a crystalline form of Compound I in about 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10%, wherein the amount represents the percentage of the total amount of Compound I or a pharmaceutically acceptable salt, solvate, or solvate salt thereof in the mixture. In one embodiment, the mixture comprises an amorphous form of Compound I in about 90%, 85%, 80%, 75%, 70%, 65%, 60%, 55%, 50%, 45%, 40%, 35%, 30%, 25%, or 20% and a crystalline form of Compound I in about 10%, 15%, 20%, 25%, 30%, 35%, 40%, 45%, 50%, 55%, 60%, 65%, 70%, 75%, or 80%, wherein the amount represents the percentage of the total amount of Compound I or a pharmaceutically acceptable salt, solvate, or solvate salt thereof in the mixture. In one embodiment, the mixture comprises a crystalline form of Compound I in about 99%, 98%, 97%, 96%, 95%, 94%, 93%, 92%, 91%, or 90% and an amorphous form of Compound I in about 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10%, wherein the amount represents the percentage of the total amount of Compound I or a pharmaceutically acceptable salt, solvate, or solvate salt thereof in the mixture. In one embodiment, the mixture comprises a crystalline form of Compound I in about 90%, 85%, 80%, 75%, 70%, 65%, 60%, 55%, 50%, 45%, 40%, 35%, 30%, 25%, or 20% and an amorphous form of Compound I in about 10%, 15%, 20%, 25%, 30%, 35%, 40%, 45%, 50%, 55%, 60%, 65%, 70%, 75%, or 80%, wherein the amount represents the percentage of the total amount of Compound I or a pharmaceutically acceptable salt, solvate, or solvate salt thereof in the mixture. In one embodiment, the crystalline form of Compound I is Form A.

In one embodiment, the Compound I can be present in the pharmaceutical composition as a pharmaceutically acceptable salt. In one embodiment, the Compound I can be present in the pharmaceutical composition as a pharmaceutical solvate. In one embodiment, the Compound I can be present in the pharmaceutical composition as a pharmaceutical solvate salt. In one embodiment, the Compound I can be present in the pharmaceutical composition as an amorphous form. In one embodiment, the Compound I can be present in the pharmaceutical composition as a crystalline form that is not Form A. In one embodiment, the Compound I can be present in the pharmaceutical composition as a crystalline form that is not Form A that is anhydrous Compound I. In one embodiment, the Compound I can be present in the pharmaceutical composition as a crystalline form that is not Form A that is anhydrous free base of Compound I.

In one embodiment, a pharmaceutical composition, as described herein, further comprises one or more additional therapeutically active agents. In one embodiment, one or more additional therapeutically active agents are selected from therapeutics useful for treating cancer, neurological disease, a disorder characterized by abnormal accumulation of α-synuclein, a disorder of an aging process, cardiovascular disease, bacterial infection, viral infection, mitochondrial related disease, mental retardation, deafness, blindness, diabetes, obesity, autoimmune disease, glaucoma, Leber's Hereditary Optic Neuropathy, and rheumatoid arthritis. In one embodiment, one or more additional therapeutically active agents are selected from therapeutics useful for treating prostate cancer of breast cancer.

In some embodiments, the one or more additional therapeutic agents is a poly (ADP-ribose) polymerase (PARP) inhibitor including but not limited to olaparib, niraparib, rucaparib, talazoparib; an androgen receptor ligand-binding domain inhibitor including but not limited to enzalutamide, apalutamide, darolutamide, bicalutamide, nilutamide, flutamide, ODM-204, TAS3681; an inhibitor of CYP17 including but not limited to galeterone, abiraterone, abiraterone acetate; a microtubule inhibitor including but not limited to docetaxel, paclitaxel, cabazitaxel (XRP-6258); a modulator of PD-1 or PD-L1 including but not limited to pembrolizumab, durvalumab, nivolumab, atezolizumab; a gonadotropin releasing hormone agonist including but not limited to cyproterone acetate, leuprolide; a 5-alpha reductase inhibitor including but not limited to finasteride, dutasteride, turosteride, bexlosteride, izonsteride, FCE 28260, SKF105,111; a vascular endothelial growth factor inhibitor including but not limited to bevacizumab (Avastin); a histone deacetylase inhibitor including but not limited to OSU-HDAC42; an integrin alpha-v-beta-3 inhibitor including but not limited to VITAXIN; a receptor tyrosine kinase including but not limited to sunitumib; a phosphoinositide 3-kinase inhibitor including but not limited to alpelisib, buparlisib, idealisib; an anaplastic lymphoma kinase (ALK) inhibitor including but not limited to crizotinib, alectinib; an endothelin receptor A antagonist including but not limited to ZD-4054; an anti-CTLA4 inhibitor including but not limited to MDX-010

(ipilimumab); an heat shock protein 27 (HSP27) inhibitor including but not limited to OGX 427; an androgen receptor degrader including but not limited to ARV-330, ARV-110; a androgen receptor DNA-binding domain inhibitor including but not limited to VPC-14449; a bromodomain and extra-terminal motif (BET) inhibitor including but not limited to BI-894999, GSK25762, GS-5829; an N-terminal domain inhibitor including but not limited to a sintokamide; an alpha-particle emitting radioactive therapeutic agent including but not limited to radium 233 or a salt thereof; niclosamide; or related compounds thereof; a selective estrogen receptor modulator (SERM) including but not limited to tamoxifen, raloxifene, toremifene, arzoxifene, bazedoxifene, pipindoxifene, lasofoxifene, enclomiphene; a selective estrogen receptor degrader (SERD) including but not limited to fulvestrant, ZB716, OP-1074, elacestrant, AZD9496, GDC0810, GDC0927, GW5638, GW7604; an aromatase inhibitor including but not limited to anastrazole, exemestane, letrozole; selective progesterone receptor modulators (SPRM) including but not limited to mifepristone, lonaprison, onapristone, asoprisnil, lonaprisnil, ulipristal, telapristone; a glucocorticoid receptor inhibitor including but not limited to mifepristone, COR108297, COR125281, ORIC-101, PT150; HER2 receptor antagonist including but not limited to trastuzumab, neratinib; or a mammalian target of rapamycin (mTOR) inhibitor including but not limited to everolimus, temsirolimus, an AKT inhibitor including but not limited to MK-2206; a Bcl-2 inhibitor including but not limited to venetoclax; an aurora kinase inhibitor including but not limited to alisertib; a Wnt-targeting antagonist including but not limited to DKK-1-4 proteins (Dikhopf), secreted Frazzle related proteins (sFRP); a CYP11a inhibitor including but not limited to ODM-208; a selective androgen receptor N-terminal domain inhibitor including but not limited to LY2452473; or EZH2 inhibitor including but not limited to CPI-1205. In another embodiment, the second therapeutically active agent is a nonsteroidal antiandrogen (NSAA).

In one embodiment, pharmaceutical composition comprises a) enzalutamide, apalutamide, or darolutamide, b) a crystalline Form A of Compound I, or a pharmaceutically acceptable salt, solvate, or solvate salt thereof, and c) a pharmaceutically acceptable carrier or excipient. In one embodiment, pharmaceutical composition comprises a) enzalutamide, b) a crystalline Form A of Compound I, or a pharmaceutically acceptable salt, solvate, or solvate salt thereof, and c) a pharmaceutically acceptable carrier or excipient.

In one embodiment, pharmaceutical composition comprises a) enzalutamide, apalutamide, or darolutamide, b) an amorphous form of Compound I, or a pharmaceutically acceptable salt, solvate, or solvate salt thereof, and c) a pharmaceutically acceptable carrier or excipient. In one embodiment, pharmaceutical composition comprises a) enzalutamide, b) an amorphous form of Compound I, or a pharmaceutically acceptable salt, solvate, or solvate salt thereof, and c) a pharmaceutically acceptable carrier or excipient.

In one embodiment, pharmaceutical composition comprises venetoclax, a crystalline Form A of Compound I, or a pharmaceutically acceptable salt, solvate, or solvate salt thereof, and a pharmaceutically acceptable carrier or excipient.

In one embodiment, pharmaceutical composition comprises venetoclax, an amorphous form of Compound I, or a pharmaceutically acceptable salt, solvate, or solvate salt thereof, and a pharmaceutically acceptable carrier or excipient.

In a further embodiment of the present disclosure, a pharmaceutical composition comprising one or more solid forms of Compound I (e.g., a crystalline form such as Form A or an amorphous form), or a pharmaceutically acceptable salt, solvate, or solvate salt thereof, and a pharmaceutically acceptable excipient or adjuvant is provided. The pharmaceutically acceptable excipients and adjuvants are added to the composition or formulation for a variety of purposes. In another embodiment, a pharmaceutical composition comprising one or more solid forms of Compound I, or a pharmaceutically acceptable salt, solvate, or solvate salt thereof, further comprises a pharmaceutically acceptable carrier. In one embodiment, a pharmaceutically acceptable carrier includes a pharmaceutically acceptable excipient, binder, and/or diluent. In one embodiment, suitable pharmaceutically acceptable excipients include, but are not limited to, water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, the pharmaceutical compositions of the present disclosure may additionally contain other adjunct components conventionally found in pharmaceutical compositions, at their art-established usage levels. Thus, for example, the pharmaceutical compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

For the purposes of this disclosure, the solid forms of Compound I of the present disclosure can be formulated for administration by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters.

The solid forms of Compound I disclosed herein can be formulated in accordance with the routine procedures adapted for desired administration route. Accordingly, the solid forms of Compound I disclosed herein can take such forms as suspensions, solutions or emulsions in oily or aqueous vehicles, and can contain formulatory agents such as suspending, stabilizing and/or dispersing agents. The solid forms of Compound I disclosed herein can also be formulated as a preparation for implantation or injection. Thus, for example, the solid forms of Compound I can be formulated with suitable polymeric or hydrophobic materials (e.g., as an emulsion in an acceptable oil) or ion exchange resins, or as sparingly soluble derivatives (e.g., as a sparingly soluble salt). Alternatively, the active ingredient can be in powder form for constitution with a suitable vehicle, e.g., sterile pyrogen-free water, before use. Suitable formulations for each of these methods of administration can be found, for example, in Remington: The Science and Practice of Pharmacy, A. Gennaro, ed., 20th edition, Lippincott, Williams & Wilkins, Philadelphia, Pa.

In certain embodiments, a pharmaceutical composition of the present disclosure is prepared using known techniques, including, but not limited to mixing, dissolving, granulating, dragee-making, levigating, emulsifying, encapsulating, entrapping or tableting processes.

In one embodiment, the present disclosure provides a pharmaceutical composition comprising a compound of formula (I)-(VI) and/or (A)-(H-I), or a pharmaceutically acceptable salt, solvate, or solvate salt thereof, as disclosed herein, combined with a pharmaceutically acceptable carrier. In one embodiment, suitable pharmaceutically acceptable carriers include, but are not limited to, inert solid fillers or diluents and sterile aqueous or organic solutions. Pharmaceutically acceptable carriers are well known to those skilled in the art and include, but are not limited to, from about 0.01 to about 0.1 M and preferably 0.05M phosphate buffer or 0.8% saline. Such pharmaceutically acceptable carriers can be aqueous or non-aqueous solutions, suspensions and emulsions. Examples of non-aqueous solvents suitable for use in the present application include, but are not limited to, propylene glycol, polyethylene glycol, vegetable oils such as olive oil, and injectable organic esters such as ethyl oleate.

Aqueous carriers suitable for use in the present application include, but are not limited to, water, ethanol, alcoholic/aqueous solutions, glycerol, emulsions or suspensions, including saline and buffered media. Oral carriers can be elixirs, syrups, capsules, tablets and the like.

Liquid carriers suitable for use in the present application can be used in preparing solutions, suspensions, emulsions, syrups, elixirs and pressurized compounds. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators.

Liquid carriers suitable for use in the present application include, but are not limited to, water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and *arachis* oil). For parenteral administration, the carrier can also include an oily ester such as ethyl oleate and isopropyl myristate. Sterile liquid carriers are useful in sterile liquid form comprising solid forms of Compound I for parenteral administration. The liquid carrier for pressurized compounds disclosed herein can be halogenated hydrocarbon or other pharmaceutically acceptable propellant.

Solid carriers suitable for use in the present application include, but are not limited to, inert substances such as lactose, starch, glucose, methyl-cellulose, magnesium stearate, dicalcium phosphate, mannitol and the like. A solid carrier can further include one or more substances acting as flavoring agents, lubricants, solubilizers, suspending agents, fillers, glidants, compression aids, binders or tablet-disintegrating agents; it can also be an encapsulating material. In powders, the carrier can be a finely divided solid which is in admixture with the finely divided active compound. In tablets, the active compound is mixed with a carrier having the necessary compression properties in suitable proportions and compacted in the shape and size desired. The powders and tablets preferably contain up to 99% of the active compound. Suitable solid carriers include, for example, calcium phosphate, magnesium stearate, talc, sugars, lactose, dextrin, starch, gelatin, cellulose, polyvinylpyrrolidine, low melting waxes and ion exchange resins. A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach.

Parenteral carriers suitable for use in the present application include, but are not limited to, sodium chloride solution, Ringer's dextrose, dextrose and sodium chloride, lactated Ringer's and fixed oils. Intravenous carriers include fluid and nutrient replenishers, electrolyte replenishers such as those based on Ringer's dextrose and the like. Preservatives and other additives can also be present, such as, for example, antimicrobials, antioxidants, chelating agents, inert gases and the like.

Carriers suitable for use in the present application can be mixed as needed with disintegrants, diluents, granulating agents, lubricants, binders and the like using conventional techniques known in the art. The carriers can also be sterilized using methods that do not deleteriously react with the compounds, as is generally known in the art.

Diluents may be added to the formulations of the present invention. Diluents increase the bulk of a solid pharmaceutical composition and/or combination and may make a pharmaceutical dosage form containing the composition and/or combination easier for the patient and care giver to handle. Diluents for solid compositions and/or combinations include, for example, microcrystalline cellulose (e.g., AVICEL), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol, and talc.

Additional embodiments relate to the pharmaceutical formulations wherein the formulation is selected from the group consisting of a solid, powder, liquid and a gel. In certain embodiments, a pharmaceutical composition of the present invention is a solid (e.g., a powder, tablet, a capsule, granulates, and/or aggregates). In certain of such embodiments, a solid pharmaceutical composition comprising one or more ingredients known in the art, including, but not limited to, starches, sugars, diluents, granulating agents, lubricants, binders, and disintegrating agents.

Solid pharmaceutical compositions that are compacted into a dosage form, such as a tablet, may include excipients whose functions include helping to bind the active ingredient and other excipients together after compression. Binders for solid pharmaceutical compositions and/or combinations include acacia, alginic acid, carbomer (e.g., carbopol), carboxymethylcellulose sodium, dextrin, ethyl cellulose, gelatin, guar gum, gum tragacanth, hydrogenated vegetable oil, hydroxyethyl cellulose, hydroxypropyl cellulose (e.g., KLUCEL), hydroxypropyl methyl cellulose (e.g., METHOCEL), liquid glucose, magnesium aluminum silicate, maltodextrin, methylcellulose, polymethacrylates, povidone (e.g., KOLLIDON, PLASDONE), pregelatinized starch, sodium alginate, and starch.

The dissolution rate of a compacted solid pharmaceutical composition in the patient's stomach may be increased by the addition of a disintegrant to the composition and/or combination. Disintegrants include alginic acid, carboxymethylcellulose calcium, carboxymethylcellulose sodium (e.g., AC-DI-SOL and PRIMELLOSE), colloidal silicon dioxide, croscarmellose sodium, crospovidone (e.g., KOLLIDON and POLYPLASDONE), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB), potato starch, and starch.

Glidants can be added to improve the flowability of anon-compacted solid composition and/or combination and to improve the accuracy of dosing. Excipients that may function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition and/or combination to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that may be included in the composition and/or combination of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In certain embodiments, a pharmaceutical composition of the present invention is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

Liquid pharmaceutical compositions can be prepared using one or more solid forms of Compound I, or a pharmaceutically acceptable salt, solvate, or solvate salt thereof, and any other solid excipients where the components are dissolved or suspended in a liquid carrier such as water, vegetable oil, alcohol, polyethylene glycol, propylene glycol, or glycerin.

For example, formulations for parenteral administration can contain as common excipients sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers can be useful excipients to control the release of active compounds. Other potentially useful parenteral delivery systems include ethylene-vinyl acetate copolymer particles, osmotic pumps, implantable infusion systems, and liposomes. Formulations for inhalation administration contain as excipients, for example, lactose, or can be aqueous solutions containing, for example, polyoxyethylene-9-auryl ether, glycocholate and deoxycholate, or oily solutions for administration in the form of nasal drops, or as a gel to be applied intranasally. Formulations for parenteral administration can also include glycocholate for buccal administration, methoxysalicylate for rectal administration, or citric acid for vaginal administration.

Liquid pharmaceutical compositions can contain emulsifying agents to disperse uniformly throughout the composition and/or combination an active ingredient or other excipient that is not soluble in the liquid carrier. Emulsifying agents that may be useful in liquid compositions and/or combinations of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as aspartame, lactose, sorbitol, saccharin, sodium saccharin, sucrose, aspartame, fructose, mannitol, and invert sugar may be added to improve the taste.

Preservatives and chelating agents such as alcohol, sodium benzoate, butylated hydroxyl toluene, butylated hydroxyanisole, and ethylenediamine tetraacetic acid may be added at levels safe for ingestion to improve storage stability.

A liquid composition can also contain a buffer such as guconic acid, lactic acid, citric acid or acetic acid, sodium guconate, sodium lactate, sodium citrate, or sodium acetate. Selection of excipients and the amounts used may be readily determined by the formulation scientist based upon experience and consideration of standard procedures and reference works in the field.

In one embodiment, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Formulations for intravenous administration can comprise solutions in sterile isotonic aqueous buffer. Where necessary, the formulations can also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where the solid form of Compound I is to be administered by infusion, it can be dispensed in a formulation with an infusion bottle containing sterile pharmaceutical grade water, saline or dextrose/water. Where the solid form of Compound I is administered by injection, an ampule of sterile water for injection or saline can be provided so that the ingredients can be mixed prior to administration.

Suitable formulations further include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

In certain embodiments, a pharmaceutical composition of the present invention is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition of the present invention comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition of the present invention comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80 and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition of the present invention comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

Appropriate pharmaceutical compositions of the present disclosure can be determined according to any clinically-acceptable route of administration of the composition to the subject. The manner in which the composition is administered is dependent, in part, upon the cause and/or location. One skilled in the art will recognize the advantages of certain routes of administration. The method includes administering an effective amount of the therapeutically active agent or one or more solid forms of Compound I (or composition comprising the therapeutic agent or Compound I) to achieve a desired biological response, e.g., an amount effective to alleviate, ameliorate, or prevent, in whole or in part, a symptom of a condition to be treated, e.g., oncology and neurology disorders. In various aspects, the route of administration is systemic, e.g., oral or by injection. The therapeutic agents or Compound I, or pharmaceutically acceptable salts or derivatives thereof, are administered orally, nasally, transdermally, pulmonary, inhalationally, buccally, sublingually, intraperintoneally, subcutaneously, intramuscularly, intravenously, rectally, intrapleurally, intrathecally, intraportally, and parenterally. Alternatively or in addition, the route of administration is local, e.g., topical, intra-tumor and pen-tumor. In some embodiments, the solid form of Compound I is administered orally.

In certain embodiments, a pharmaceutical composition of the present disclosure is prepared for oral administration. In certain of such embodiments, a pharmaceutical composition is formulated by combining one or more agents and pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for transmucosal administration. In certain of such embodiments, penetrants appropriate to the barrier to be permeated are used in the formulation. Such penetrants are generally known in the art.

In certain embodiments, a pharmaceutical composition is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a pharmaceutical agent of the invention and a suitable powder base such as lactose or starch.

In other embodiments the solid forms of Compound I of the present disclosure are administered by the intravenous route. In further embodiments, the parenteral administration may be provided in a bolus or by infusion.

In certain embodiments, a pharmaceutical composition is prepared for rectal administration, such as a suppository or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, and lanolin and water in oil emulsions. Exemplary suitable cream bases include, but are not limited to, cold cream and hydrophilic ointment.

In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more solid forms of Compound I, or a pharmaceutically acceptable salt, solvate, or solvate salt thereof, are formulated as a prodrug. In certain embodiments, upon in vivo administration, a prodrug is chemically converted to the biologically, pharmaceutically or therapeutically more active form. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing a solid form of Compound I is the corresponding active form. In certain embodiments, a prodrug comprises a short peptide (poly aminoacid) bound to an acid group. In certain of such embodiments, the peptide is cleaved upon administration to form the corresponding active form.

In certain embodiments, a prodrug is produced by modifying a pharmaceutically active compound such that the Compound I will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

In various aspects, the amount of the one or more solid forms of Compound I, or a pharmaceutically acceptable salt, solvate, or solvate salt thereof can be administered at about 0.001 mg/kg to about 100 mg/kg body weight (e.g., about 0.01 mg/kg to about 10 mg/kg or about 0.1 mg/kg to about 5 mg/kg).

The concentration of a disclosed solid forms of Compound I in a pharmaceutically acceptable mixture will vary depending on several factors, including the dosage of the solid forms of Compound I to be administered, the pharmacokinetic characteristics of the solid form(s) employed, and the route of administration. The agent may be administered in a single dose or in repeat doses. The dosage regimen utilizing the solid forms of Compound I of the present invention is selected in accordance with a variety of factors including type, species, age, weight, sex and medical condition of the patient; the severity of the condition to be treated; the route of administration; the renal and hepatic function of the patient; and the particular solid forms or salt thereof employed. Treatments may be administered daily or more frequently depending upon a number of factors, including the overall health of a patient, and the formulation and route of administration of the selected form(s). An ordinarily skilled physician or veterinarian can readily determine and prescribe the effective amount of the drug required to prevent, counter or arrest the progress of the condition.

The solid forms of Compound I, or a pharmaceutically acceptable salt, solvate, or solvate salt thereof, or pharmaceutical compositions of the present disclosure may be manufactured and/or administered in single or multiple unit dose forms.

Therapeutic Use

The crystalline forms and the pharmaceutical compositions of the present disclosure find use in any number of methods. For example, in some embodiments the crystalline forms and the pharmaceutical compositions are useful in methods for modulating androgen receptor (AR). In some embodiments, modulating androgen receptor (AR) activity is in a mammalian cell. In some embodiments, modulating androgen receptor (AR) can be in a subject in need thereof (e.g., a mammalian subject) and for treatment of any of the described conditions or diseases.

In one embodiment, the modulating AR is binding to AR. In other embodiments, the modulating AR is inhibiting AR.

In one embodiment, the modulating AR is modulating AR N-terminal domain (NTD).

In one embodiment, the modulating AR is binding to AR NTD. In other embodiments, the modulating AR is inhibiting AR NTD. In one embodiment, the modulating AR is modulating AR N-terminal domain (NTD). In some embodiments, modulating the AR is inhibiting transactivation of androgen receptor N-terminal domain (NTD).

In other embodiments, modulating androgen receptor (AR) activity is for treatment of at least one indication selected from the group consisting of: prostate cancer, breast cancer, ovarian cancer, bladder cancer, pancreatic cancer, hepatocellular cancer, endometrial cancer, salivary gland carcinoma, hair loss, acne, hirsutism, ovarian cysts, polycystic ovary disease, precocious puberty, spinal and bulbar muscular atrophy, age related macular degeneration, and combinations thereof. For example, in some embodiments, the indication is prostate cancer. In other embodiments, the prostate cancer is primary/localized prostate cancer, locally advanced prostate cancer, recurrent prostate cancer, metastatic prostate cancer, advanced prostate cancer, or metastatic castration-resistant prostate cancer (CRPC), or hormone-sensitive prostate cancer. While in other embodiments, the prostate cancer is androgen dependent prostate cancer. In other embodiments, the spinal and bulbar muscular atrophy is Kennedy's disease.

In one embodiment of the present disclosure, a method of treating a condition associated with cell proliferation in a patient in need thereof is provided. In one embodiment, the present invention provides a method of treating cancer or tumors. In another embodiment, the present invention provides a method of treating prostate cancer or breast cancer. In another embodiment, the present invention provides a method of treating prostate cancer.

In one embodiment of the present disclosure, a method of reducing, inhibiting, or ameliorating cell proliferation in a patient in need thereof is provided. In one embodiment, the reducing, inhibiting, or ameliorating in the method disclosed herein, is in vivo. In another embodiment, the reducing, inhibiting, or ameliorating is in vitro.

In one embodiment, the cells in the method disclosed herein, are a cancer cells. In one embodiment, the cancer cells are a prostate cancer cells. In one embodiment, the prostate cancer cells are cells of primary/localized prostate cancer (newly diagnosed or early stage), locally advanced prostate cancer, recurrent prostate cancer (e.g., prostate cancer which was not cured with primary therapy), metastatic prostate cancer, advanced prostate cancer (e.g., after castration for recurrent prostate cancer), metastatic castration-resistant prostate cancer (CRPC), or hormone-sensitive prostate cancer. In another embodiment, the prostate cancer cells are cells of a metastatic castration-resistant prostate cancer. In other embodiments, the prostate cancer cells are an androgen-dependent prostate cancer cells or an androgen-independent prostate cancer cells. In one embodiment, the cancer cells are breast cancer cells.

In one embodiment, the condition or disease associated with cell proliferation is cancer. In one embodiment of any one of the methods disclosed herein, the cancer is selected from the group consisting of: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy, and age-related macular degeneration. In one embodiment, the condition or disease is prostate cancer. In one embodiment, prostate cancer is selected from primary/localized prostate cancer, locally advanced prostate cancer, recurrent prostate cancer, metastatic prostate cancer, advanced prostate cancer, metastatic castration-resistant prostate cancer (CRPC), or hormone-sensitive prostate cancer. In another embodiment, the prostate cancer is a metastatic castration-resistant prostate cancer. In some embodiments, the prostate cancer is an androgen-dependent prostate cancer cells or an androgen-independent prostate cancer. In one embodiment, the condition or disease is breast cancer. In one embodiment, the breast cancer is AR-positive triple negative breast cancer.

In another embodiment of the present disclosure, a method for reducing or preventing tumor growth, comprising contacting tumor cells with a pharmaceutical composition or a combination as disclosed herein.

In one embodiment, reducing or preventing tumor growth includes reduction in tumor volume. In one embodiment, reducing or preventing tumor growth includes complete elimination of tumors. In one embodiment, reducing or preventing tumor growth includes stopping or halting the existing tumor to grow. In one embodiment, reducing or preventing tumor growth includes reduction in the rate of tumor growth. In one embodiment, reducing or preventing tumor growth includes reduction in the rate of tumor growth such that the rate of tumor growth before treating a patient with the methods disclosed herein (r1) is faster than the rate of tumor growth after said treatment (r2) such that r1>r2.

In one embodiment, the reducing or preventing in the method disclosed herein is in vivo. In another embodiment, the treating is in vitro.

In one embodiment, the tumor cell in the method disclosed herein is selected from prostate cancer, breast cancer, ovarian cancer, endometrial cancer, or salivary gland carcinoma. In one embodiment, the tumor cells are prostate cancer tumor cells. In one embodiment, the prostate cancer tumor cells are tumor cells of primary/localized prostate cancer, locally advanced prostate cancer, recurrent prostate cancer, metastatic prostate cancer, advanced prostate cancer, metastatic castration-resistant prostate cancer (CRPC), or hormone-sensitive prostate cancer. In other embodiments, the prostate cancer is a metastatic castration-resistant prostate cancer. In some embodiments, the prostate cancer is androgen-dependent prostate cancer or androgen-independent prostate cancer. In another embodiment, the tumor cells are is breast cancer tumor cells.

Therapeutic Use Related to Androgen Receptor Driven Gene Expression

In one embodiment, the present disclosure provides a method for treating a subject having a cancer, comprising, obtaining a sample of the cancer before and/or after treatment of the subject with a solid form of Compound I or a pharmaceutically acceptable salt, solvate, or solvate salt thereof.

In one embodiment of the present disclosure, a method of treating a patient with abnormal androgen receptor driven gene activity with a solid form of Compound I or a pharmaceutically acceptable salt, solvate, or solvate salt thereof, alone or in combination with a second therapeutic agent is provided.

In one embodiment, the present disclosure provides a method for treating a subject having a cancer, comprising, obtaining a sample of the cancer before treatment with a solid form of Compound I, and determining in the sample, the expression level of an androgen receptor driven genes. In another specific embodiment, after testing the expression level of androgen receptor driven genes, the subject is administered a solid form of Compound I or a pharmaceutically acceptable salt, solvate, or solvate salt thereof, alone and or in combination with a second therapeutically active agent as disclosed herein. In a specific embodiment, the genes are one or more selected from the group consisting of KLK2, FKBP5, TMPRSS2, KLK3, NCAPD3, NKX3-1, NDRG1, STEAP4, FAM105A, AKAP12, PMEPA1, PLPP1, SNA12, ACSL3, ERRF11, CDC6, ELL2, CENPN, RHOU, EAF2, SGK1, SLC16A6, TIPARP, IGFIR, CCND1, ADAMTS1, and PRR15L.

In one embodiment, the present disclosure provides a method of treating cancer in a subject having abnormal gene expression of one or more androgen receptor driven genes, comprising administering to the subject a solid form of Compound I or a pharmaceutically acceptable salt, solvate, or solvate salt thereof. In one embodiment of any one of the methods disclosed herein, the androgen receptor driven gene is an androgen receptor full-length driven gene. In one embodiment, the androgen receptor driven gene is an androgen receptor V7 driven gene. In one embodiment of any one of the methods disclosed herein, the gene with an abnormal activity is selected from KLK2, FKBP5, TMPRSS2, KLK3, NCAPD3, NKX3-1, NDRG1, STEAP4, FAM105A, AKAP12, PMEPA1, PLPP1, SNA12, ACSL3, ERRF11, CDC6, ELL2, CENPN, RHOU, EAF2, SGK1, SLC16A6, TIPARP, IGFIR, CCND1, ADAMTS1, or PRR15L. In one embodiment of the methods disclosed herein, cancer is selected from prostate cancer, breast cancer, ovarian cancer, endometrial cancer, or salivary gland carcinoma. In one embodiment, the cancer is prostate cancer. In one embodiment, the prostate cancer is selected from primary/localized prostate cancer, locally advanced prostate cancer, recurrent prostate cancer, metastatic prostate cancer, advanced prostate cancer, metastatic castration-resistant prostate cancer (CRPC), or hormone-sensitive prostate cancer. In other embodiments, the prostate cancer is a metastatic castration-resistant prostate cancer. In some embodiments, the prostate cancer is androgen-dependent prostate cancer or androgen-independent prostate cancer. In another embodiment, the cancer is breast cancer. In a specific embodiment, the solid form of Compound I is crystalline Form A. In a specific embodiment, the solid form of Compound I is an amorphous form.

In one embodiment, the present disclosure provides a method of treating cancer in a subject having abnormal gene expression of one or more androgen receptor driven genes, comprising administering to the subject a solid form of Compound I or a pharmaceutically acceptable salt, solvate, or solvate salt thereof. In one embodiment, the solid form of Compound I is crystalline Form A or an amorphous form in combination with a second therapeutically active agent as disclosed herein. In a specific embodiment, the second therapeutically active agent is a nonsteroidal antiandrogen (NSAA). In one embodiment of the pharmaceutical composition of the present disclosure, the androgen receptor ligand-binding domain inhibitor is enzalutamide, apalutamide, darolutamide, bicalutamide, nilutamide, flutamide, ODM-204, or TAS3681. In one embodiment, the androgen receptor ligand-binding domain inhibitor is enzalutamide.

In one embodiment of any one of the methods disclosed herein, the androgen receptor driven gene is an androgen receptor full-length driven gene. In one embodiment, the androgen receptor driven gene is an androgen receptor V7 driven gene. In one embodiment of any one of the methods disclosed herein, the gene with an abnormal activity is selected from KLK2, FKBP5, TMPRSS2, KLK3, NCAPD3, NKX3-1, NDRG1, STEAP4, FAM105A, AKAP12, PMEPA1, PLPP1, SNA12, ACSL3, ERRF11, CDC6, ELL2, CENPN, RHOU, EAF2, SGK1, SLC16A6, TIPARP, IGFIR, CCND1, ADAMTS1, or PRR15L. In one embodiment of the methods disclosed herein, cancer is selected from prostate cancer, breast cancer, ovarian cancer, endometrial cancer, or salivary gland carcinoma. In one embodiment, the cancer is prostate cancer. In one embodiment, the prostate cancer is selected from primary/localized prostate cancer, locally advanced prostate cancer, recurrent prostate cancer, metastatic prostate cancer, advanced prostate cancer, metastatic castration-resistant prostate cancer (CRPC), or hormone-sensitive prostate cancer. In other embodiments, the prostate cancer is a metastatic castration-resistant prostate cancer. In some embodiments, the prostate cancer is androgen-dependent prostate cancer or androgen-independent prostate cancer. In another embodiment, the cancer is breast cancer. In a specific embodiment, the solid form of Compound I is crystalline Form A and the second therapeutically active agent is enzalutamide. In a specific embodiment, the solid form of Compound I is an amorphous form and the second therapeutically active agent is enzalutamide.

In one embodiment, the present disclosure provides a method for treating a subject having a cancer, comprising, obtaining a sample of the cancer after treatment with an androgen receptor modulator, and determining, in the sample, the expression level of an androgen receptor driven gene, where if the gene expression level, when compared to a reference standard level, is decreased before or after treatment with the androgen receptor modulator, then proceeding with or resuming treatment of the subject with a therapeutically effective amount of the androgen receptor modulator and/or a second therapeutical active agent. In a specific embodiment, the gene is selected from one or more of the group consisting of KLK2, FKBP5, TMPRSS2, KLK3, NCAPD3, NKX3-1, NDRG1, STEAP4, FAM105A, AKAP12, PMEPA1, PLPP1, SNA12, ACSL3, ERRF11, CDC6, ELL2, CENPN, RHOU, EAF2, SGK1, SLC16A6, TIPARP, IGFIR, CCND1, ADAMTS1, and PRR15L. In one embodiment, an androgen receptor modulator administered before the sample of cancer is obtained can be the same or different from an androgen receptor modulator administered after the androgen receptor driven gene expression levels are assessed. In one embodiment, the androgen receptor modulator is a solid form of Compound I or a pharmaceutically acceptable salt, solvate, or solvate salt thereof.

In one embodiment, the present disclosure provides a method for treating a subject having a cancer, comprising, obtaining a sample of the cancer after treatment with an androgen receptor modulator, and determining, in the sample, the expression level of an androgen receptor driven gene, where if the gene expression level, when compared to a reference standard level, is decreased before or after treatment with the androgen receptor modulator, then proceeding with or resuming treatment of the subject with a therapeutically effective amount of the androgen receptor modulator or a different androgen receptor modulator and a second therapeutic agent, wherein the gene is selected from one or more of the group consisting of KLK2, FKBP5, TMPRSS2, KLK3, NCAPD3, NKX3-1, NDRG1, STEAP4, FAM105A, AKAP12, PMEPA1, PLPP1, SNA12, ACSL3, ERRF11, CDC6, ELL2, CENPN, RHOU, EAF2, SGK1, SLC16A6, TIPARP, IGFIR, CCND1, ADAMTS1, and PRR15L. In one embodiment, the second therapeutic agent is an androgen receptor ligand-binding domain inhibitor is enzalutamide, apalutamide, darolutamide, bicalutamide, nilutamide, flutamide, ODM-204, or TAS3681. In one embodiment, the androgen receptor ligand-binding domain inhibitor is enzalutamide. In one embodiment, the second therapeutic agent is a Bcl-2 inhibitor. In one embodiment, the Bcl-2 inhibitor is venetoclax. In one embodiment, the second therapeutic agent is an androgen receptor N-terminal domain inhibitor. In one embodiment, the androgen receptor modulator is a solid form of Compound I or a pharmaceutically acceptable salt, solvate, or solvate salt thereof.

In one embodiment, the present disclosure provides a method for treating a subject having a cancer, comprising, obtaining a sample of the cancer after treatment with an androgen receptor modulator, and determining, in the sample, the expression level of an androgen receptor driven genes, where if the gene expression level, when compared to a reference standard level, is decreased before or after treatment with the androgen receptor modulator, then proceeding with or resuming treatment of the subject with a therapeutically effective amount of a solid form of Compound I or a pharmaceutically acceptable salt, solvate, or solvate salt thereof, and enzalutamide, wherein the gene is selected from KLK2, FKBP5, TMPRSS2, KLK3, NCAPD3, NKX3-1, NDRG1, STEAP4, FAM105A, AKAP12, PMEPA1, PLPP1, SNA12, ACSL3, ERRF11, CDC6, ELL2, CENPN, RHOU, EAF2, SGK1, SLC16A6, TIPARP, IGFIR, CCND1, ADAMTS1, or PRR15L. In one embodiment, the androgen receptor modulator is a solid form of Compound I.

In one embodiment, the present disclosure provides a method for treating a subject having a cancer, comprising, obtaining a sample of the cancer after treatment with a solid form of Compound I or a pharmaceutically acceptable salt, solvate, or solvate salt thereof, and determining, in the sample, the expression level of an androgen receptor driven genes, where if the gene expression level, when compared to a reference standard level, is decreased before or after treatment with a solid form of Compound I or a pharmaceutically acceptable salt, solvate, or solvate salt thereof, then proceeding with or resuming treatment of the subject with a therapeutically effective amount of the solid form of Compound I or a pharmaceutically acceptable salt, solvate, or solvate salt thereof. In a specific embodiment, enzalutamide may be co-administered as second therapeutic agent. In another specific embodiment, the gene is selected from KLK2, FKBP5, TMPRSS2, KLK3, NCAPD3, NKX3-1, NDRG1, STEAP4, FAM105A, AKAP12, PMEPA1, PLPP1, SNA12, ACSL3, ERRF11, CDC6, ELL2, CENPN, RHOU, EAF2, SGK1, SLC16A6, TIPARP, IGFIR, CCND1, ADAMTS1, or PRR15L.

In one embodiment, the present disclosure provides a method for treating a subject having a cancer, comprising, obtaining a sample of the cancer after treatment with an androgen receptor modulator, and determining, in the sample, the expression level of an androgen receptor driven genes, where if the gene expression level, when compared to a reference standard level, is decreased before or after treatment with the androgen receptor modulator, then proceeding with or resuming treatment of the subject with a therapeutically effective amount of a solid form of Compound I or a pharmaceutically acceptable salt, solvate, or solvate salt thereof, wherein the gene is selected from one or more selected from the group consisting of KLK2, FKBP5, TMPRSS2, KLK3, NCAPD3, NKX3-1, NDRG1, STEAP4, FAM105A, AKAP12, PMEPA1, PLPP1, SNA12, ACSL3, ERRF11, CDC6, ELL2, CENPN, RHOU, EAF2, SGK1, SLC16A6, TIPARP, IGFIR, CCND1, ADAMTS1, and PRR15L. In one embodiment, the androgen receptor modulator is a solid form of Compound I or a pharmaceutically acceptable salt, solvate, or solvate salt thereof.

In one embodiment, the present disclosure provides a method for treating a subject having a cancer, comprising, obtaining a sample of the cancer after treatment with a solid form of Compound I or a pharmaceutically acceptable salt, solvate, or solvate salt thereof, and determining, in the sample, the expression level of an androgen receptor driven genes, where if the gene expression level, when compared to a reference standard level, is decreased before or after treatment with a solid form of Compound I or a pharmaceutically acceptable salt, solvate, or solvate salt thereof, then proceeding with or resuming treatment of the subject with a therapeutically effective amount of the solid form of Compound I or a pharmaceutically acceptable salt, solvate, or solvate salt thereof, wherein the gene is selected from one or more selected from the group consisting of KLK2, FKBP5, TMPRSS2, KLK3, NCAPD3, NKX3-1, NDRG1, STEAP4, FAM105A, AKAP12, PMEPA1, PLPP1, SNA12, ACSL3, ERRF11, CDC6, ELL2, CENPN, RHOU, EAF2, SGK1, SLC16A6, TIPARP, IGFIR, CCND1, ADAMTS1, and PRR15L.

In one embodiment of the methods disclosed herein, cancer is selected from prostate cancer, breast cancer, ovarian cancer, endometrial cancer, or salivary gland carcinoma. In one embodiment, the cancer is prostate cancer. In one embodiment, the prostate cancer is selected from primary/localized prostate cancer, locally advanced prostate cancer, recurrent prostate cancer, metastatic prostate cancer, advanced prostate cancer, metastatic castration-resistant prostate cancer (CRPC), or hormone-sensitive prostate cancer. In other embodiments, the prostate cancer is a metastatic castration-resistant prostate cancer. In some embodiments, the prostate cancer is androgen-dependent prostate cancer or androgen-independent prostate cancer. In another embodiment, the cancer is breast cancer.

In one embodiment of any one of the methods disclosed herein, the androgen receptor modulator is a solid form of Compound I or a pharmaceutically acceptable salt, solvate, or solvate salt thereof. In one embodiment, the solid form of Compound I is crystalline Form A. In one embodiment, the solid form of Compound I is an amorphous form. In one embodiment, the solid form of Compound I is Material B, C, or D.

In one embodiment of any one of the methods disclosed herein, the androgen receptor driven gene is an androgen receptor full-length driven gene. In one embodiment, the androgen receptor driven gene is an androgen receptor V7 driven gene.

In one embodiment of any one of the methods disclosed herein, the gene with an abnormal activity is selected from KLK2, FKBP5, TMPRSS2, KLK3, NCAPD3, NKX3-1, NDRG1, STEAP4, FAM105A, AKAP12, PMEPA1, PLPP1, SNA12, ACSL3, ERRF11, CDC6, ELL2, CENPN, RHOU, EAF2, SGK1, SLC16A6, TIPARP, IGF1R, CCND1, ADAMTS1, or PRR15L. See WO 2020/198710, which is hereby incorporated by reference in its entirety.

Having now generally described the invention, the same will be more readily understood through reference to the following examples, which are provided by way of illustration and are not intended to be limiting of the present invention.

EXAMPLES

The disclosure now being generally described, it will be more readily understood by reference to the following examples which are included merely for purposes of illustration of certain aspects and embodiments of the present invention, and are not intended to limit the invention General Procedures—Analytical Methods X-Ray Powder Diffraction (XRPD)

Figures labeled "Image by PatternMatch v3.0.4" were generated using unvalidated software. XRPD patterns were collected with a PANalytical X'Pert PRO MPD diffractometer or a PANalytical Empyrean diffractometer using an incident beam of Cu radiation produced using an Optix long, fine-focus source. An elliptically graded multilayer mirror was used to focus Cu Kα X-ray radiation through the specimen and onto the detector. Prior to the analysis, a silicon specimen (NIST SRM 640e) was analyzed to verify the observed position of the Si (111) peak is consistent with the NIST-certified position. A specimen of the sample was sandwiched between 3-μm-thick films and analyzed in transmission geometry. A beam-stop, short antiscatter extension, and antiscatter knife edge, were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 5.5. The data acquisition parameters for each pattern are displayed above the image (X'Pert PRO MPD) or within the Data Viewer v. 1.8 image (Empyrean) of each pattern in the Data section of this report.

XRPD Indexing

The high-resolution XRPD patterns were indexed using proprietary SSCI software (Triads™, see U.S. Pat. No. 8,576,985) or X'Pert High Score Plus 2.2a (2.2.1) in this study. Indexing and structure refinement are computational studies. Agreement between the allowed peak positions, marked with red bars, and the observed peaks indicates a consistent unit cell determination. Successful indexing of the pattern indicates that the sample is composed primarily of a single crystalline phase. Space groups consistent with the assigned extinction symbol, unit cell parameters, and derived quantities are tabulated below each figure showing tentative indexing solution. To confirm the tentative indexing solution, the molecular packing motifs within the crystallographic unit cells must be determined. No attempts at molecular packing were performed.

Thermogravimetry (TGA) and TGA/DSC Combo Analysis

TGA and TGA/DSC Combo analyses were performed using a Mettler-Toledo TGA/DSC3+ analyzer. Temperature and enthalpy adjustments were performed using indium, tin, and zinc, and then verified with indium. The balance was verified with calcium oxalate. The sample was placed in an open aluminum pan. The pan was hermetically sealed, the lid pierced, then inserted into the TG furnace. A weighed aluminum pan configured as the sample pan was placed on the reference platform. The furnace was heated under nitrogen. The data acquisition parameters are displayed in the images in the Figure section or Data section of this report.

Temperature Modulated Differential Scanning Calorimetry (TMDSC)

TMDSC was performed using Mettler-Toledo DSC3+ differential scanning calorimeter. TOPEM® overlays the isothermal or ramped temperature with a time series of random temperature pulses of different durations. A tau lag adjustment is performed with indium, tin, and zinc. The temperature and enthalpy are adjusted with octane, phenyl salicylate, indium, tin and zinc. The adjustment is then verified with octane, phenyl salicylate, indium, tin, and zinc. The sample was placed into a hermetically sealed aluminum DSC pan, and the weight was accurately recorded. The pan lid was pierced then inserted into the DSC cell. A weighed aluminum pan configured as the sample pan was placed on the reference side of the cell. The data was collected from −50° C. to 160° C. with a modulation amplitude of ±0.25° C. and a 15 to 30 second period with an underlying heating rate of 2° C./minute.

Single Crystal X-Ray Diffraction (SCXRD)

1. Preparation of the Single Crystal Sample: A solution of Compound I in acetone was prepared and filtered through a 0.2-μm nylon filter into a clean glass vial covered with perforated foil. The sample was allowed to evaporate slowly to dryness at ambient temperature. A single crystal was carefully removed from the vial wall for analysis.

2. Data Collection: A colorless plate having approximate dimensions of 0.28×0.12×0.04 mm3, was mounted on a polymer loop in random orientation. Preliminary examination and data collection were performed on a Rigaku SuperNova diffractometer, equipped with a copper anode microfocus sealed X-ray tube (Cu Kα λ=1.54184 Å) and a Dectris Pilatus3 R 200K hybrid pixel array detector. Cell constants and an orientation matrix for data collection were obtained from least-squares refinement using the setting angles of 6525 reflections in the range $4.7930° < \theta < 77.0370°$. The space group was determined by the program CRYSALISPRO (CrysAlisPro 1.171.38.41r, Rigaku Oxford Diffraction, 2015) to be $P2_1/c$ (international tables no. 14). The data were collected to a maximum diffraction angle (2θ) of 155.124° at room temperature.

3. Data Reduction: Frames were integrated with CRYSALISPRO. A total of 13457 reflections were collected, of which 5294 were unique. Lorentz and polarization corrections were applied to the data. The linear absorption coefficient is 3.352 mm$^{-1}$ for Cu Kα radiation. An empirical absorption correction using CRYSALISPRO was applied. Transmission coefficients ranged from 0.789 to 1.000. Intensities of equivalent reflections were averaged. The agreement factor for the averaging was 2.22% based on intensity.

4. Structure Solution and Refinement: The structure was solved by direct methods using SHELXT (see Sheldrick, G.

M. *Acta Cryst.* 2015, A71, 3-8). The remaining atoms were located in succeeding difference Fourier syntheses. The structure was refined using SHELXL-2014 (see Sheldrick, G. M. *Acta Cryst.* 2008, A64, 112-122; Id.). Hydrogen atoms residing on nitrogen were refined independently. Hydrogen atoms residing on carbon were included in the refinement but restrained to ride on the atom to which they are bonded. The structure was refined in full-matrix least-squares by minimizing the function:

$$\Sigma w(|F_o|^2 - |F_c|^2)^2$$

where the weight, w, is defined as $1/[\sigma^2(F_o^2) + (0.1009\ P)^2 + (0.9289\ P)]$, where $P = (F_o^2 + 2F_c^2)/3$. Scattering factors were taken from the "International Tables for Crystallography" (International Tables for Crystallography, Vol. C, Kluwer Academic Publishers: Dordrecht, The Netherlands, 1992, Tables 4.2.6.8 and 6.1.1.4). Of the 5294 reflections used in the refinements, only the reflections with intensities larger than twice their uncertainty [I>2□(I)], 4317, were used in calculating the fit residual, R. The final cycle of refinement included 351 variable parameters, 15 restraints, and converged with respective unweighted and weighted agreement factors of:

$$R = \sum |F_o - F_c| / \sum F_o = 0.0559$$

$$R_w = \sqrt{\left(\sum w(F_o^2 - F_c^2)^2 / \sum w(F_o^2)^2\right)} = 0.1711$$

The standard deviation of an observation of unit weight (goodness of fit) was 1.05. The highest peak in the final difference Fourier had an electron density of 0.674 e/Å$^3$. The minimum negative peak had a value of −0.649 e/Å$^3$.

5. Calculated X-ray Powder Diffraction (XRPD) Pattern: A calculated XRPD pattern was generated for Cu radiation using MERCURY (Macrae, C. F. Edgington, P. R. McCabe, P. Pidcock, E. Shields, G. P. Taylor, R. Towler M. and van de Streek, J. *J. Appl. Cryst.*, 2006, 39, 453-457) and the atomic coordinates, space group, and unit cell parameters from the single crystal structure.

6. Atomic Displacement Ellipsoid and Packing Diagrams: The atomic displacement ellipsoid diagram was prepared using MERCURY. Atoms are represented by 50% probability anisotropic thermal ellipsoids.

Abbreviations

| Abbreviations/Acronyms | Full Name/Description |
|---|---|
| agg. | Aggregates |
| B/E | Birefringence/extinction |
| B | Birefringence |
| d | Day(s) |
| FC | Fast cooling |
| FD | Freeze drying (lyophilization) |
| FE | Fast evaporation |
| h | Hour(s) |
| LIMS | Laboratory information management system |
| ppt | Precipitation |
| RE | Rotary evaporation |
| RT | Room temperature |
| SC | Slow cooling |
| SE | Slow evaporation |
| T$_g$ | Glass transition temperature |
| UM | Unknown morphology |
| VF | Vacuum filtration |
| v/v | Volume/Volume |

Example 1: Synthesis and Characterization of Crystalline Form A of N-(4-((4-(2-(3-chloro-4-(2-chloroethoxy)-5-cyanophenyl)propan-2-yl)phenoxy)methyl)pyrimidin-2-yl)methanesulfonamideN-(4-((4-(2-(3-chloro-4-(2-chloroethoxy)-5-cyanophenyl)propan-2-yl)phenoxy)methyl)pyrimidin-2-yl)methanesulfonamide (Compound I)

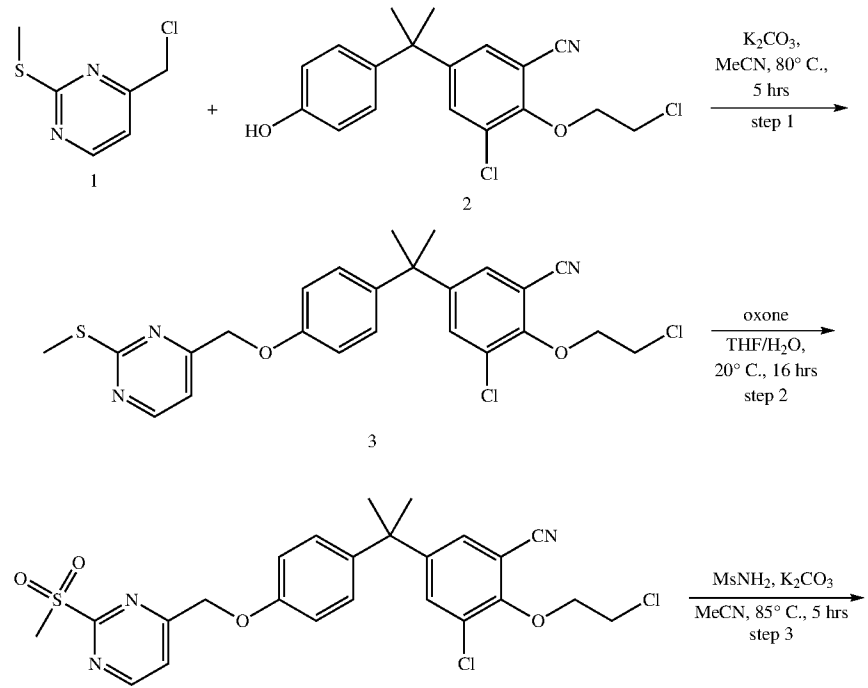

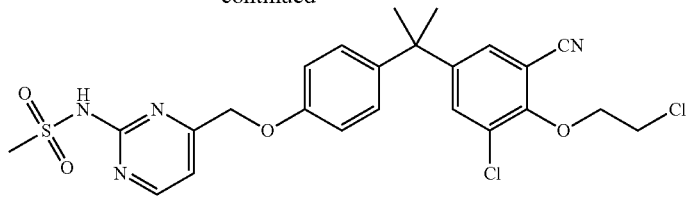

Compound I

Step 1: A mixture of 4-(chloromethyl)-2-methylsulfanyl-pyrimidine (1) (324 mg, 1.86 mmol), 3-chloro-2-(2-chloroethoxy)-5-(2-(4-hydroxyphenyl)propan-2-yl)benzonitrile (2) (0.5 g, 1.43 mmol) and $K_2CO_3$ (493 mg, 3.57 mmol) in MeCN (4 mL) was stirred at 80° C. for 5 hrs. LCMS and HPLC showed the reaction was completed and 81.4% of the desired product formed. The resulting mixture was quenched with sat.$NH_4Cl$ (10 mL) and extracted with EtOAc (10 mL×3). The combined organic layers were washed with brine (10 mL), dried over $Na_2SO_4$, filtered and concentrated under reduced pressure. The residue was purified by MPLC to give 3-chloro-2-(2-chloroethoxy)-5-(2-(4-((2-(methylthio)pyrimidin-4-yl)methoxy)phenyl)propan-2-yl)benzonitrile (3) (0.54 g, yield: 77.4%) as colorless syrup. $^1$H NMR (400 MHz, $CDCl_3$) δ=8.54 (d, J=4.8 Hz, 1H), 7.45 (d, J=2.4 Hz, 1H), 7.32 (d, J=2.4 Hz, 1H), 7.22 (d, J=5.2 Hz, 1H), 7.12 (d, J=8.8 Hz, 2H), 6.89 (d, J=8.8 Hz, 2H), 5.09 (s, 2H), 4.43 (t, J=6.4 Hz, 2H), 3.88 (t, J=6.4 Hz, 2H), 2.59 (s, 3H), 1.65 (s, 6H). after work up: HPLC (220 nm): 94.7%. LCMS (220 nm): 93.5%. Exact Mass: 487.1; found 488.0/490.0.

Step 2: To a suspension of 3-chloro-2-(2-chloroethoxy)-5-(2-(4-((2-(methylthio)pyrimidin-4-yl)methoxy) phenyl) propan-2-yl)benzonitrile (3) (1.07 g, 2.19 mmol) in THF (20 mmL) was added a suspension of Oxone (5.39 g, 8.76 mmol) in water (20 mL) at 20° C. The mixture was stirred at 20° C. for 16 hrs. LCMS and HPLC showed the reaction was completed and 93.0% of the desired product formed. The resulting mixture was quenched with sat.$Na_2SO_3$. The aqueous layer was extracted with EtOAc (30 mL×3). The combined organic layers were washed with brine (30 mL), dried over $Na_2SO_4$, filtered and concentrated under reduced pressure to give 3-chloro-2-(2-chloroethoxy)-5-(2-(4-((2-(methylsulfonyl)pyrimidin-4-yl) methoxy)phenyl)propan-2-yl)benzonitrile (4) (1.04 g, yield: 91.2%) as colorless syrup. $^1$H NMR (400 MHz, $CDCl_3$) δ=8.94 (d, J=4.8 Hz, 1H), 7.85 (d, J=4.8 Hz, 1H), 7.45 (d, J=2.4 Hz, 1H), 7.31 (d, J=2.4 Hz, 1H), 7.15 (d, J=8.8 Hz, 2H), 6.91 (d, J=8.8 Hz, 2H), 5.30 (s, 2H), 4.43 (t, J=6.4 Hz, 2H), 3.88 (t, J=6.0 Hz, 2H), 3.40 (s, 3H), 1.66 (s, 6H). IPC detection: HPLC (220 nm): 92.956%. LCMS (220 nm): 93.0%. Exact Mass: 519.1; found 520.1/522.1.

Step 3: A suspension of 3-chloro-2-(2-chloroethoxy)-5-(2-(4-((2-(methylsulfonyl)pyrimidin-4-yl)methoxy) phenyl) propan-2-yl)benzonitrile (4) (30 mg, 0.058 mmol), methanesulfonamide (11 mg, 0.12 mmol) and $K_2CO_3$ (15.9 mg, 0.12 mmol) in MeCN (2 mL) was stirred at 85° C. for 5 hrs. LCMS showed the reaction was completed and 91.6% of the desired product formed. The resulting mixture was partitioned between EtOAc (2 mL) and aq.$NH_4Cl$ (2 mL). The aqueous layer was extracted with EtOAc (2 mL×3). The combined organic layers were washed with brine (2 mL), dried over $Na_2SO_4$, filtered and concentrated under reduced pressure to give Compound I, Form A (40 mg) as yellow solid. $^1$H NMR (400 MHz, $CDCl_3$) δ=8.77 (br s, 1H), 8.64 (d, J=4.8 Hz, 1H), 7.45 (d, J=2.4 Hz, 1H), 7.32 (d, J=2.4 Hz, 1H), 7.29 (d, J=5.2 Hz, 1H), 7.13 (d, J=8.8 Hz, 2H), 6.90 (d, J=8.8 Hz, 2H), 5.11 (s, 2H), 4.43 (t, J=6.0 Hz, 2H), 3.88 (t, J=6.0 Hz, 2H), 3.48 (s, 3H), 1.65 (s, 6H). IPC detection: LCMS (220 nm): 91.6% purity. Exact Mass: 534.1; found 535.1/537.2.

XRPD spectrum was obtained for Form A as shown in FIG. 1 and Tables 1A-1B. The sample likely contains small amount of NaCl. The sharp peaks at 27.3±0.2 and at 31.7±0.2 degrees two-theta is consistent with the presence of NaCl. Form A was determined successfully in this study, and the results indicate it is an anhydrous/unsolvated material.

TGA/DSC thermograms were also obtained for Form A as shown in FIG. 2. By TGA, a weight loss of 2.2 wt % was observed from 50-230° C., which is likely due to the loss of residual solvents in the sample. The dramatic change in the slope of the thermogram starting at about 284° C. (onset) is likely associated with the decomposition of the material. By DSC, an endotherm is observed at approximately 182° C. (onset), which could be due to the melting of the material.

Figure 3:
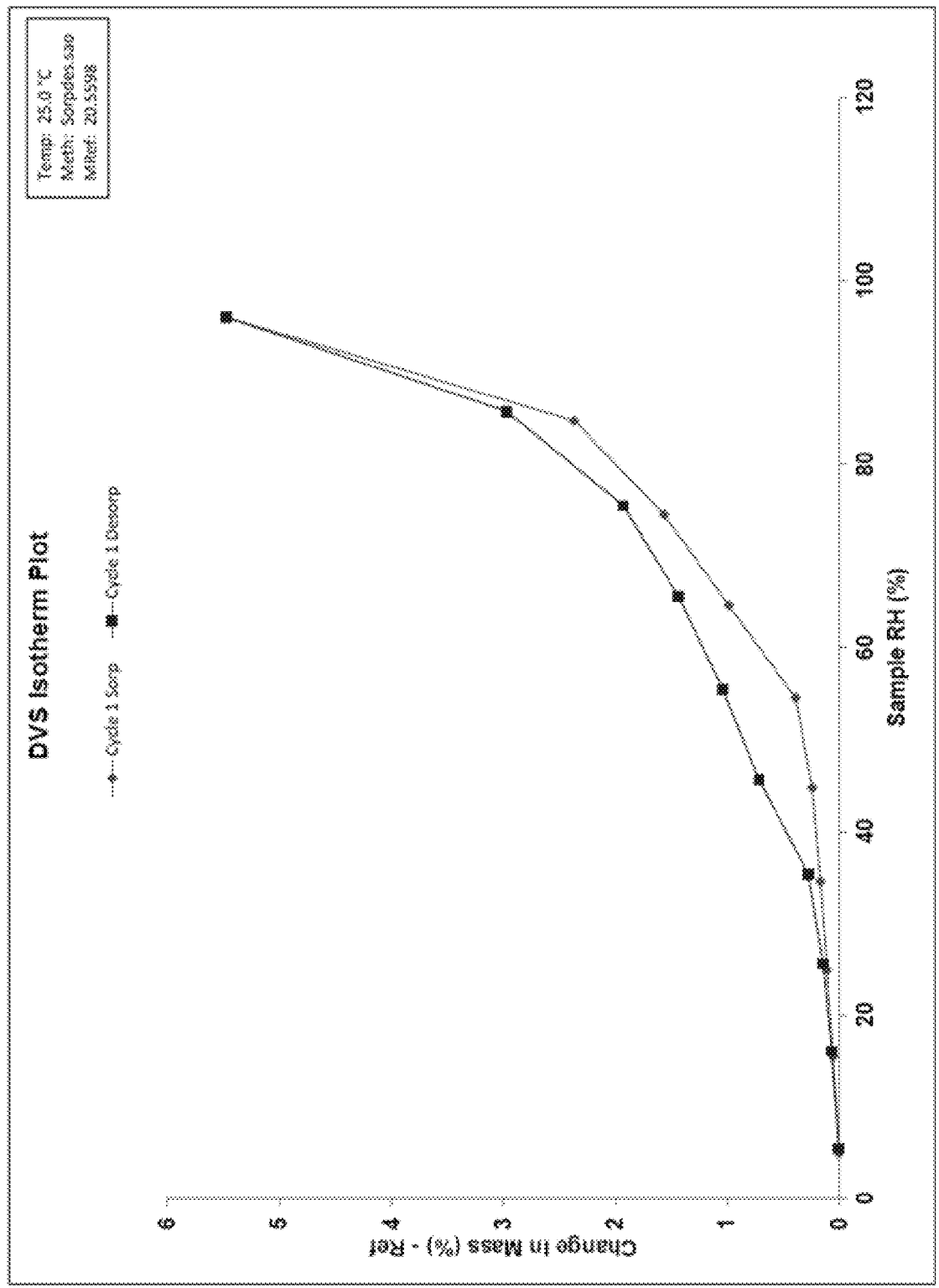
FIG. 3 shows dynamic vapor sorption (DVS) profile of crystalline Form A of Compound I.

DVS (dynamic vapor sorption) analysis was carried out on Form A (Table 2, FIG. 3). The DVS profile of Form A displayed a total of 5.474% weight gain during sorption from 5% to 95% RH, with the majority of the weight gain occurred above 55% RH (1.978 wt % gain from 55% to 85% RH and 3.106 wt % gain from 85% RH to 95% RH). During desorption from 95% RH to 5% RH, the sample displayed 5.472% weight loss, and some hysteresis was observed from 95% to 25% RH. The DVS data suggest that Form A exhibits low hygroscopicity within 5%-55% RH, limited hygroscopicity within 55%-85% RH, and significant hygroscopicity within 85%-95% RH.

Solids recovered after DVS analysis was consistent with Form A by XRPD analysis.

TABLE 2

DVS Isotherm Analysis

| | Target RH (%) | Sample RH (%) | Sorp Mass Change (%) | Sample RH (%) | Desorp Mass Change (%) | Hysteresis |
|---|---|---|---|---|---|---|
| Cycle 1 | 5.0 | 4.9 | 0.000 | 5.4 | 0.002 | |
| | 15.0 | 15.4 | 0.055 | 16.1 | 0.060 | 0.013 |
| | 25.0 | 24.9 | 0.111 | 25.6 | 0.146 | 0.036 |
| | 35.0 | 34.5 | 0.169 | 35.3 | 0.277 | 0.108 |
| | 45.0 | 44.8 | 0.242 | 45.6 | 0.716 | 0.474 |
| | 55.0 | 54.5 | 0.390 | 55.5 | 1.040 | 0.650 |
| | 65.0 | 64.6 | 0.906 | 65.6 | 1.438 | 0.452 |
| | 75.0 | 74.5 | 1.567 | 75.5 | 1.931 | 0.364 |
| | 85.0 | 84.7 | 2.368 | 85.8 | 2.072 | 0.604 |
| | 95.0 | 96.0 | 5.474 | 96.0 | 5.474 | |

Example 2: Solubility Experiments and Polymorph Screening Experiments

The approximate solubility of Compound I in various organic solvents was determined by adding solvent aliquots to weighed samples Compound I. Weighed samples of Compound I were treated with aliquots of the test solvents or solvent mixtures at ambient temperature. Complete dissolution of the test material was determined by visual inspection. Solubility was estimated based on the total solvent volume used to provide complete dissolution. The actual solubility may be greater than the value calculated because of the use of solvent aliquots that were too large or due to a slow rate of dissolution. If complete dissolution was not achieved during the experiment, the solubility is expressed as "less than" (<). If complete dissolution was achieved by only one aliquot addition, the value is reported as "larger than" (>).

A summary of the approximate solubility of Compound I in various organic solvents is provided in Table 3.

TABLE 3

Approximate Solubility of Compound I

| Solvent | Solubility (mg/mL) (a) | Initial Observation | Observation after Storage (48 h) |
|---|---|---|---|
| acetone | 5.3 (c) | — | — |
| ACN | 2.04 (c) | — | — |
| DCM | 20 | clear anther solution | clear brown solution |
| dioxant | >107 (b) | clear brown solution | settled solids |
| DMA | >79 | clear brown solution | clear amber solution |
| DMSO | >12 (c) | — | — |
| Et$_2$O | <2 | cloudy off-white suspension | settled solids |
| EtOAc | 1.97 (c) | — | — |
| EtOH | 0.17 (c) | — | — |
| iPrOAc | <1 | cloudy off-white suspension | settled solids |
| MEK | 6 | clear amber solution | clear yellow/amber solution |
| MeOH | 0.21 (c) | — | — |
| MTBE | <1 | cloudy white suspension | settled solids |
| NMP | >117 | clear brown solution | clear brown solution |
| THF | 54 | clear amber solution | fine yellow suspension |
| toluene | 1 | cloudy beige solution | settled solids |

(a): Unless otherwise specified, solubilities are estimated at ambient temperature and reported to the nearest mg/mL; if complete dissolution was not achieved, the value is reported as "<"; if complete dissolution was achieved with one aliquot of solvent, the value is reported as ">"; the actual solubility may be larger than the value calculated because of the use of solvent aliquots that were too large or due to a slow rate of dissolution.
(b): Based on observations during the screen on samples at much larger scales, the approximate solubility in p-dioxane is within 35-103 mg/mL.
(c): Equilibrium solubility data acquired at 24 hours.

Various method of polymorph screening was conducted as described below.

The slurry-trituration experiments were conducted by stirring Compound I in specified organic solvents or solvent mixtures at various temperatures for 4-12 days. Sufficient amounts of solids of Compound I were added to selected solvents or solvent mixtures so that excess solids remained. The mixtures were then triturated with stir bars at designated temperatures for specified periods of time. Solids were isolated by centrifugation using Spin-X centrifuge tubes equipped with a 0.45 μm nylon filter. Solids were air dried before analysis.

A summary of experimental conditions and results is included in Table 4. Based on XRPD analysis, all slurry-trituration experiments generated solids that are consistent with Form A of Compound I.

TABLE 4

Polymorph Screen of Compound I - Slurry-Trituration Experiments

| Solvent | Conditions (a) | Observation | XRPD Result |
|---|---|---|---|
| acetone | RT, 12 d | beige solution, beige solids | Form A |
| ACN | RT, 12 d | beige solution, beige solids | Form A |
| dioxane | RT, 4 d | suspension, beige solids; analyzed wet | Form A |
| 4:1 (v/v) dioxane/heptane | RT, 7 d | beige solution, beige solids | Form A |
| DCM | RT, 12 d | orange solution, beige solids | Form A |
| 2:1 (v/v) DCM/MeOH | RT, 7 d | beige solution beige solids | Form A |
| EtOAc | RT, 12 d | beige solution, beige solids | Form A |
| MEK | RT, 12 d | beige solution, beige solids | Form A |
| THF | RT, 5 d | wet beige solids, dried during analysis | Form A |
| 1:1 (v/v) THF/MeOH | RT, 7 d | beige solution, beige solids | Form A |
| iPrOAc | 50° C., 7 d | beige solutions, beige solids, UM, B/E | Form A |
| MTBE | 50° C., 7 d | beige solution, beige solids, UM, minor B/E | Form A |
| MeOH | 50° C., 7 d | beige solution, beige solids, UM | Form A |
| EtOH | 50° C., 7 d | beige solution, beige solids, UM, minor B/E | Form A |
| toluene | 50° C., 7 d | beige solution beige solids, UM | Form A |

(a): Temperatures and time are approximate.

To examine the propensity of Compound I to exist as hydrates, the slurry-trituration experiments were also conducted in selected aqueous mixtures with high water activities ($A_w \geq \sim 0.7$). As shown in Table 5, all the water activity slurries generated Form A of Compound I.

TABLE 5

Polymorph Screen of Compound I - Water Activity Slurries

| Solvent (a) | $A_w$ (b) | Conditions | Observations | XRPD Results |
|---|---|---|---|---|
| acetone/H$_2$O (80/20) | 0.82 | RT, 9 d | beige solids | Form A |
|  |  | 50° C., 6 d | beige solids | Form A |
| HFIPA/H$_2$O (80/20) | 1.41 | RT, 6 d | beige solids | Form A |
| DMF/H$_2$O (50/50) | 0.70 | RT, 6 d | beige solids | Form A |

(a): Solvent ratios are approximate and by volume.
(b): Water activity values are approximate and represent the water activity of the solvent system at 25° C. The activity coefficient calculations are based on modeling the interactions between functional groups present in the components. These calculated water activity values were not verified experimentally.

Polymorph screening was performed using various solvent-based approaches including evaporation, cooling, solvent/anti-solvent addition, and combinations of the techniques. For slow cooling (SC) and fast cooling (FS) experiments, saturated or concentrated solutions of Compound I were prepared in selected solvents at elevated temperatures and filtered through pre-warmed 0.2-μm nylon filters (unless specified in Table 6) into pre-warmed clean vials at the temperature. Solutions were then removed from the heating plate and left at ambient conditions (FC), or allowed to cool to ambient temperature on the heating plate with heat turned off (SC). If no handleable amount of solids appeared in vials, samples were moved to sub-ambient conditions. If not handleable amount of solids appeared after sub-ambient storage, the experiment was converted to an anti-solvent addition experiment.

For solvent/anti-solvent addition (SAS) experiments, Sub-ambient solutions from cooling attempts, or saturated/ concentrated solutions of Compound I prepared in selected solvents were filtered through 0.2-μm nylon filters into specified antisolvent at ambient temperature. Samples were either isolated immediately for analysis, or stirred at specified conditions before isolation. Detailed cooling and anti-solvent addition experimental conditions, observations, and XRPD results are summarized in Table 6.

When using dioxane as the solvent during solvent/anti-solvent addition attempts, it was observed that the choice of an anti-solvent significantly impacts the experimental results. As detailed in Table 6, the addition of a dioxane solution into $H_2O$ generated Form A, while the addition into heptane or hexanes yielded Material B or Material D, respectively. Insufficient amount of solids were observed when a dioxane solution was added into $Et_2O$. In all these attempts, the solvent ratio was kept constant at 1:3 (v/v) of dioxane/anti-solvent.

TABLE 6

Polymorph Screen of Compound I - Cooling and Anti-Solvent Addition

| Solvent (a) | Conditions | Observations | XRPD Results |
|---|---|---|---|
| 1:1 acetone/heptane | 1) API solution (e.g., Compound I solution) in 10 mL acetone filtered into 10 mL heptane<br>2) stirred, RT, 12 d (days) | 1) clear solution<br>2) clear solution | — |
| 1:2 ACN/$H_2O$ | 1) SC in ACN, 50° C. to RT, kept 3 d<br>2) kept at 2-8° C., 7 d<br>3) kept in freezer, 5 d<br>4) added cold solution into $H_2O$, centrifuged | 1) clear solution<br>2) clear yellow solution<br>3) clear yellow solution<br>4) white cloudy solution, wet beige solids, needles, B/E | Form A |
| 1:3 dioxane/$Et_2O$ | 1) API solution in 3 mL dioxane filtered into 9 mL $Et_2O$<br>2). shaken then let sat on bench for 5 min<br>3) stirred, RT, 1 d | 1) solution became hazy but no apparent solids<br>2) solids observed<br>3) no apparently increase in solids amount | IS |
| 1:3 dioxane/heptane | 1) API solution in 5 mL dioxane filtered into 15 mL heptane, shaken<br>2) VF | 1) immediate white ppt, pink suspension<br>2) pink solids, minor B/E, UM | Material B |
| | 1) API solution in 5 mL dioxane filtered into 15 mL heptane, shaken<br>2) centrifuged, analyzed wet | 1) immediate white ppt, pink suspension<br>2) pink solids, needles, B/E; analyzed wet | Material B |
| | 1) API solution in 5 mL dioxane filtered into 15 mL heptane, shaken<br>2) stirred, RT, 3 d | 1) immediate white ppt, pink suspension<br>2) milky suspension, beige solids | Material B |
| | 1) API solution in 5 mL dioxane filtered into 15 mL heptane, shaken<br>2) stirred, RT, 15 d | 1) white solids, needles & agg., B/E | Material B |
| 1:3 dioxane/hexanes | 1) API solution in 3 mL dioxane filtered into 9 mL hexanes; shaken<br>2) stirred, RT, 1 d; centrifuged | 1) solution turned cloudy immediately upon addition; solids on the side and bottom<br>2) beige solids; agg., UM, partial B; analyzed damp | Material D |
| 1:3 dioxane/$H_2O$ | 1) API solution in 3 mL dioxane filtered into 9 mL H2O<br>2) centrifuged | 1) immediate ppt<br>2) beige solids; agg. of B/E particles; analyzed wet | Form A |
| 1:2 EtOAc/EtOH | 1) SC in EtOAc, 50° C. to RT<br>2) kept at 2-8° C., 4 d<br>3) kept in freezer, 5 d<br>4) added cold solution into EtOH, centrifuged | 1) clear solution<br>2) clear yellow solution<br>3) clear yellow solution<br>4) clear solution, no solids | — |
| 1:3 MEK/$Et_2O$ | 1) FC in MEK, 50° C. to RT<br>2) kept at 2-8° C., 7 d<br>3) kept in freezer, 5 d<br>4) added cold solution into $Et_2O$, centrifuged | 1) clear solution<br>2) clear yellow solution<br>3) clear yellow solution<br>4) clear solution, no solids | — |
| 1:3 THF/MeOH | 1) FC in THF, 50° C. to RT<br>2) kept at 2-8° C., 7 d<br>3) kept in freezer, 5 d<br>4) added cold solution into MeOH, centrifuged | 1) clear solution<br>2) clear yellow solution<br>3) clear yellow solution<br>4) clear solution, no solids | — |
| 3:10 THF/hexanes | 1) API solution in 2 mL THF filtered into 10 mL hexanes<br>2) VF | 1) immediate white ppt<br>2) pink solids, B/E, UM | Form A |

(a) Solvent ratios are by volume. MEK = methyl ethyl ketone

Evaporation studies were conducted. For fast evaporation (FE) and slow evaporation (SE), solutions of Compound I were prepared in selected solvents and filtered through 0.2-μm nylon filters into clean glass vials, and allowed to evaporate at ambient temperature from open vials (FE) or from vials covered with perforated aluminum foil (SE). Fast evaporation was assisted with a steady flow of $N_2$ gas where indicated. Detailed experimental conditions, observations, and XRPD results for evaporation studies are summarized in Table 7.

TABLE 7

Polymorph Screen of Compound I - Evaporation

| Solvent | Condition | Observation | XRPD Result |
|---|---|---|---|
| acetone | SE, RT | orange solids, dendritic particles, B/E, single crystal | Form A (a) |
| DCM | FE, RT | beige solids UM, B/E | Form A |
| DMSO | FE, RT, $N_2$ assisted | beige/brown solids, UM, B/E | Form A |
| MEK | FE, RT | yellow solids, UM, B/E | Form A |
| THF | SE, RT | beige solids, UM, B/E | Form A |

(a) identified by single crystal x-ray diffraction

The majority of the experimental conditions for polymorph screening generated solids that are consistent with Form A.

Figure 4:
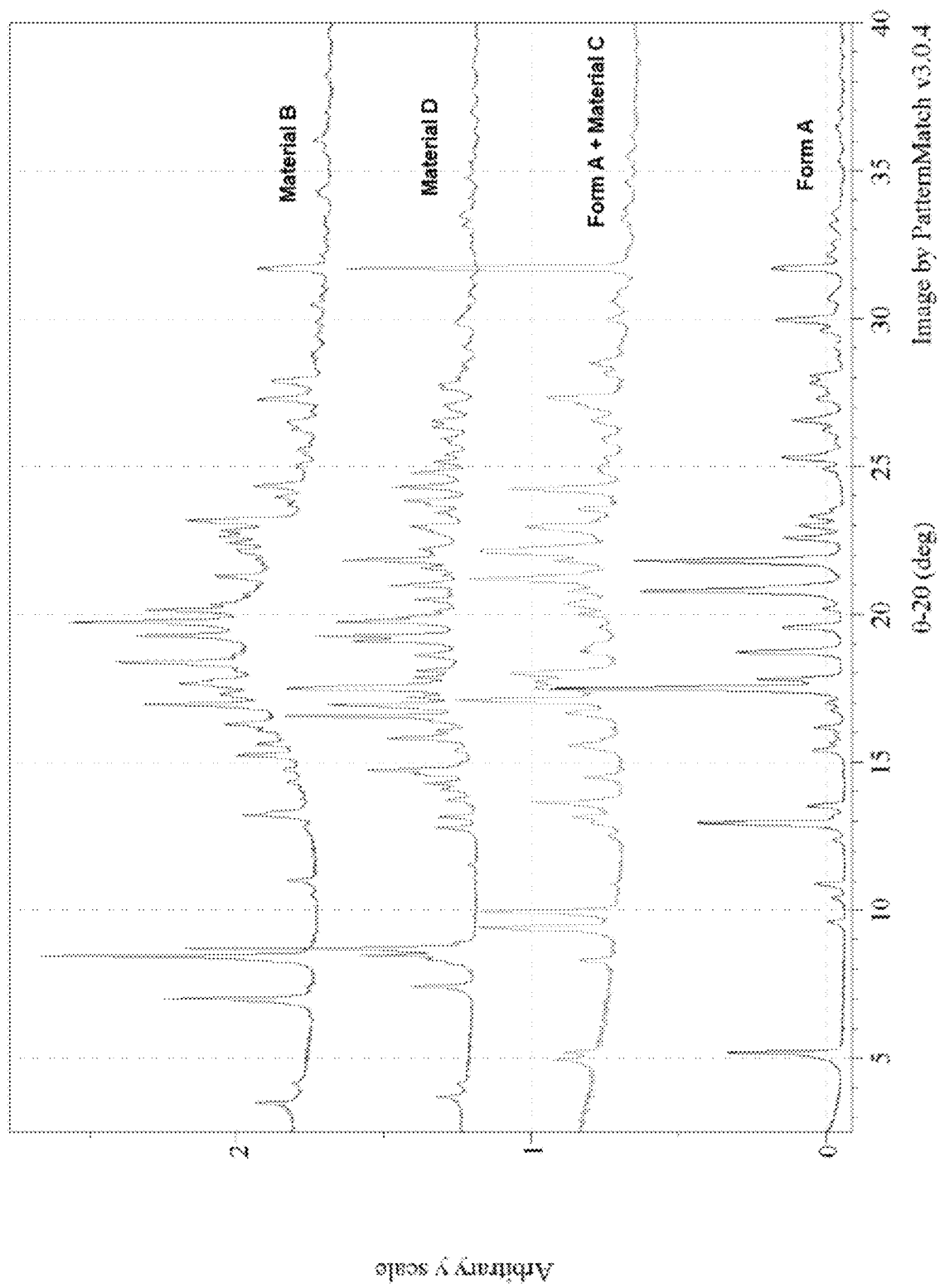
FIG. 4 shows XRPD spectrum overlay of Compound I in crystalline Form A, Material C with crystalline Form A, Material B, and Material D.

Example 3: Observation of Materials B, C, and D in Polymorph Screening Experiments As shown in Example 2, multiple solvent/anti-solvent attempts were performed in 1:3 (v/v) dioxane/heptane (Table 6), which consistently produced Compound I in a form labeled as Material B. See FIG. 4 for XRPD spectrum of Material B. Indexing attempts on XRPD pattern of Material B were not successful.

Material B was found to be unstable upon drying (Table 8), and therefore it was not further characterized. A mixture of Form A and Material C was obtained when Material B was dried at 65-66° C. under vacuum. See FIG. 4 for XRPD spectrum of Material C with Form A. When dried at ambient conditions on a filter paper, Material B converted to a disordered Material C. Based on experimental conditions to generate Material B and its drying studies, without being bound to any theory, Material B could be a solvated material which can convert to Material C upon drying.

TABLE 8

Drying Study on Material B

| Material | Conditions (a) | Observations | XRPD Results |
|---|---|---|---|
| Material B | 65-66° C., vacuum, 5 d | beige solids, UM, B | Material C + Form A |
| Material B | RT, on filter paper, 3 d | beige solids, UM | disordered Material C + peaks |
| Material D | 50-52° C., vacuum, 3 d | beige solids, UM partial B | Form A |

(a) Temperatures and time are approximate.

In order to evaluate the relative stability between Form A and Material C, a competitive slurry was performed. About equal amounts (by mass) of Material C (mixture w/some Form A) and Form A were added to acetone so that solids persisted and were stirred at room temperature for 9 days. Solids were isolated by centrifugation using Spin-X centrifuge tubes equipped with a 0.45 μm nylon filter. Beige solids were observed. By XRPD, the post-slurry solids are consistent with a pure phase of Form A indicating Form A is more stable than Material C under the examined condition. Material C could be an anhydrous material.

Material D was observed in 1:3 (v/v) dioxane/hexanes by solvent/anti-solvent addition followed by ambient slurry for 1 day (Table 5). Based on visual observations, Material D and Material B appear to have some similarity in their XRPD patterns. See FIG. 4 for XRPD spectrum of Material D. Indexing attempts on XRPD pattern of Material D were not successful.

Further analyses, including $^1$H NMR and TGA/DSC were performed on Material D. The $^1$H NMR spectrum of Material D is consistent with the provided chemical structure of Compound I. Based on the NMR spectrum, Material D contains about 0.9 mol/mol of dioxane and trace amount of hexanes.

Figure 5:
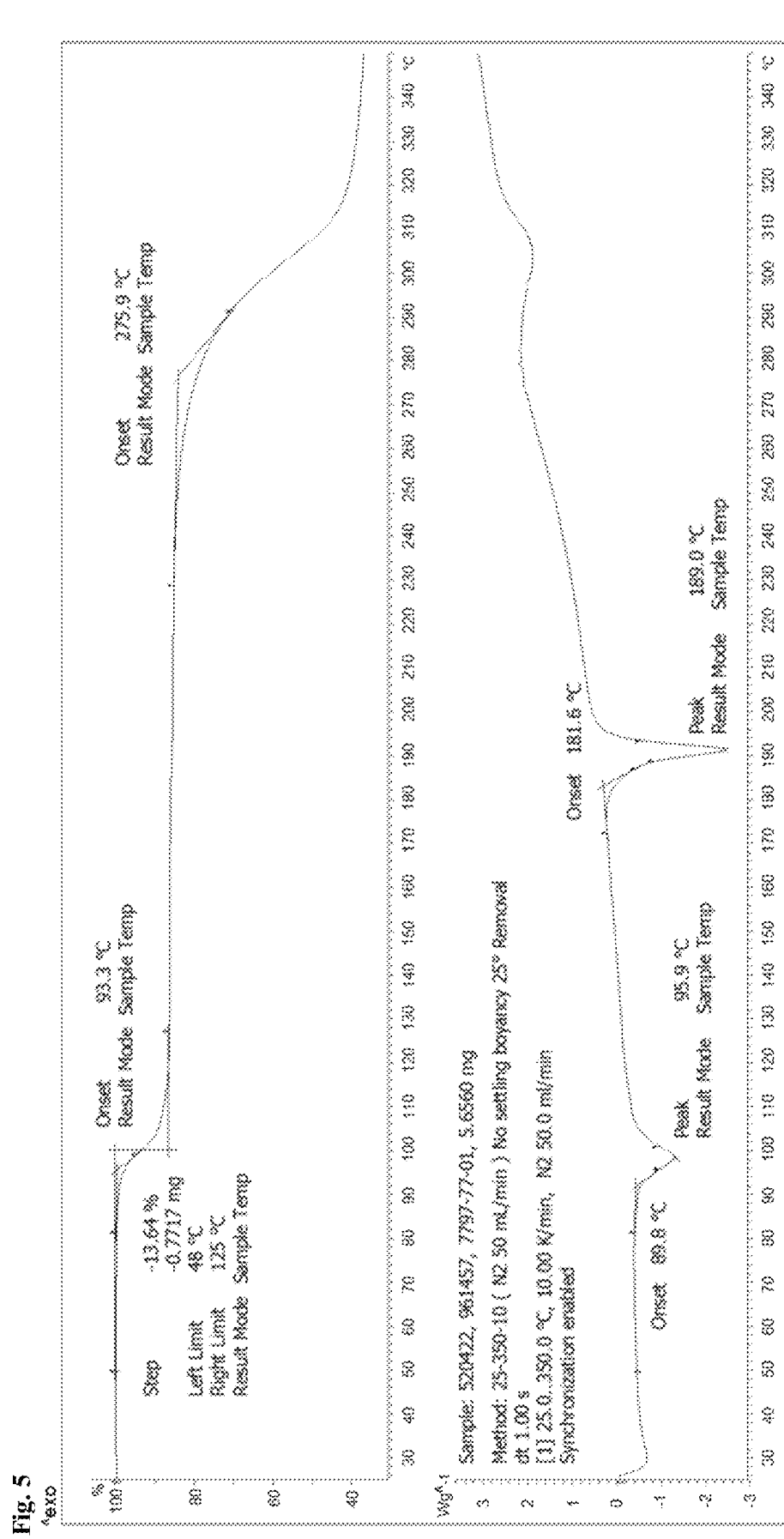
FIG. 5 shows thermogravimetric analysis (TGA)/differential scanning calorimetry (DSC) thermograms of Material D of Compound I.

The TGA/DSC thermograms of Material D are shown in FIG. 5. By TGA, a step-like weight loss is observed with an onset at about 93° C., indicating Material D is a solvated material. The sample displays a weight loss of 13.6 wt % within 48-125° C., corresponding to ~0.96 moles of dioxane, which is consistent with the NMR data. The DSC thermogram shows an endotherm at about 90° C. (onset), which is consistent with the TGA step-like weight loss and is likely due to desolvation of Material D. Upon further heating, a sharp endotherm is observed at 182° C. (onset), which could be due to melting of Form A. Material D likely converts to Form A upon desolvation.

The endotherm observed at 182° C. is likely due to Form A melting because Material D was observed to desolvate into Form A by XRPD when dried at 50-52° C./vacuum conditions for 3 days (FIG. 6). Based on characterization data and the drying result, without being bound to any theory, Material D is likely a solvated material of Compound I.

Example 4. Amorphous Form of Compound I

Variety of solvent-based techniques, including rotary evaporation and lyophilization, were carried out to screen for an amorphous form of Compound I. Experimental conditions, observations, and XRPD results are detailed in Table 9.

TABLE 9

Experiments to Screen for an Amorphous Form of Compound I

| Solvent | Condition | Observation | XRPD Result |
|---|---|---|---|
| DCM | 1) dissolved 198 mg in 20 mL DCM, filtered | 1) clear orange solution | x-ray amorphous + NaCl |
|  | 2) RE @ 63° C. | 2) beige solids, some B noticed, but mostly no B |  |
|  | 3) secondary dried @ vacuum, RT, 1 d | 3) — |  |
|  | 1) dissolved 205 mg in 20 mL DCM, filtered | 1) clear orange solution | disordered Form A |
|  | 2) RE @ 61° C. | 2) beige solids |  |
|  | 3) secondary dried @ vacuum, RT, 3 d | 3) beige glassy solids |  |
| dioxane | 1) FD, 6 d | 1) white fluffy solids, no B, UM | disordered |

Rotary evaporation experiments were performed using DCM as a solvent. Dilute solutions of Compound I were prepared in DCM and filtered through 0.2-μm nylon filters into a clear round bottom flasks. The flasks were attached to a rotary evaporator and immersed in a water bath at specified temperatures and DCM was rapidly evaporated to dryness under vacuum. The samples underwent secondary drying under vacuum at room temperature in a vacuum oven before XRPD testing.

The sample generated from the first rotary evaporation experiment was secondary dried at ambient temperature under vacuum for 1 day and then analyzed by XRPD. By XRPD, the sample displays broad halos with crystalline peaks due to NaCl, indicating successful generation of an amorphous form of Compound I ("x-ray amorphous"). See FIG. 7, third spectrum from bottom.

Materials described as "x-ray amorphous" are typically characterized further by thermal analysis where the appearance of a glass transition ($T_g$) provides support for the non-crystalline nature of the material. Temperature modulated DSC was performed on the material to investigate the $T_g$ (Table 10). As shown in FIG. 8, $T_g$ was observed at approximately 61° C. as a step change in the reversing heat flow signal. On further heating, an exotherm likely due to crystallization was observed at about 91° C. (peak). The endotherm at about 178° C. (onset) could be, without bound to any theory, due to melting of the crystallized material, which could be Form A based on crystallization study (Table 11). The endotherm has a slightly lower temperature than the endotherm observed for Form A (182° C., FIG. 2), which could be due to the specimen containing an amorphous or disordered portion (i.e., not completely crystallized during the analysis).

TABLE 10

Analysis of Selected Material

| Material | Analysis | Results (a) |
| --- | --- | --- |
| Form A | SCXRD | crystal structure successfully determined |
| Material D | ¹H NMR | consistent with the chemical structure of EPI-7386; contains dioxane (~0.9 mol/mol) and trace hexanes |
|  | TGA/DSC | TGA: |
|  |  | 13.6 wt % loss from 48-125° C. |
|  |  | 93° C. (step, onset) |
|  |  | 276° C. (decomp. onset) |
|  |  | DSC: |
|  |  | 90° C. (endo, onset) |
|  |  | 182° C. (endo, onset) |
| x-ray amorphous (w/NaCl) | ¹H NMR | consistent with the chemical structure of EP1-7386; contains trace DCM (~0.004 mol/mol) |
|  | TGA | 1.0 wt % loss from 45-200° C. |
|  |  | 280° C. (decomp. onset) |
|  | TMDSC | Reversing heat flow: |
|  |  | 61° C. ($T_g$, midpoint) |
|  |  | ΔCp 0.4 J/g·° C. |
|  |  | Total heat flow: |
|  |  | 91° C. (exo, peak) |
|  |  | 178° C. (endo, onset) |

(a) Temperatures from DSC and TGA are rounded to the whole numbers; ΔCp and wt % from TGA are rounded to one decimal place.

TABLE 11

Crystallization Study of Amorphous or Disordered forms of Compound I

| Solvent | Starting Material | Conditions (a) | Observations | XRPD Results |
| --- | --- | --- | --- | --- |
| — | Amorphous | 1) stored at RT, desiccator, 10 d | 1) minor B | disordered Form A |
| acetone | Disordered | 1) stirred, RT, 4 d | 1) white solids | Form A |
| H₂O |  | 1) stirred, RT, 4 d | 1) white solids | Form A |

(a) Times are approximate.

Figure 9:
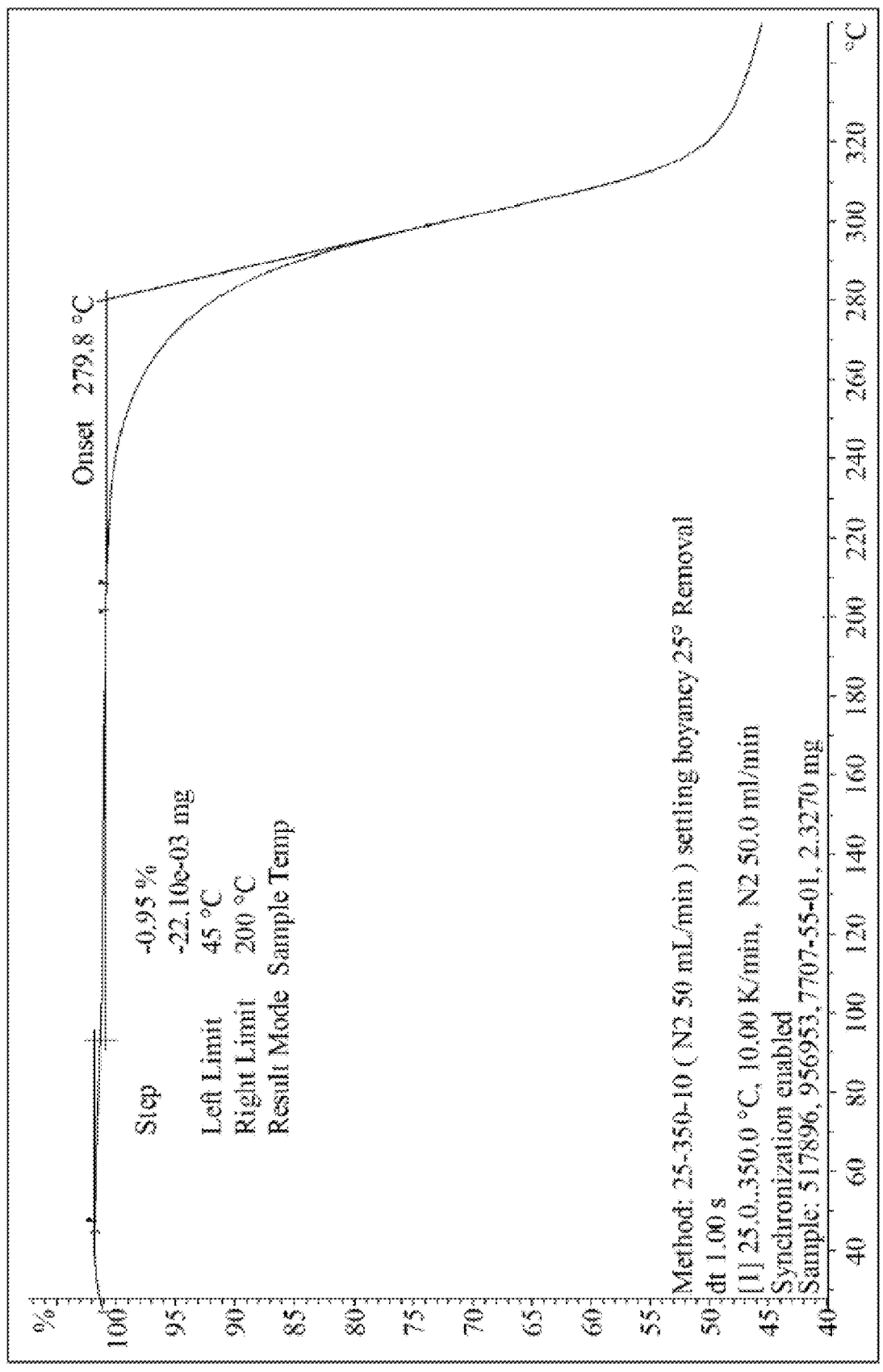
FIG. 9 shows a TGA thermogram of an amorphous form of Compound I.

Further analyses including ¹H NMR and TGA were also collected on this amorphous sample (Table 10). The ¹H NMR spectrum was consistent with the chemical structure of Compound I and contains trace amount of DCM. By TGA (FIG. 9), about 1.0 wt % loss is observed from 45-200° C., which is likely due to the residual DCM and moisture in the material. The dramatic change in the slope of the TGA thermogram starting at 280° C. (onset) is likely associated with the decomposition of the material. This amorphous form of Compound I was observed to become disordered Form A upon ambient storage in a desiccator for about 10 days (FIG. 10, top spectrum), indicating amorphous Compound I is physically not stable and crystallizes into Form A at ambient temperature. A repeated rotary evaporation attempt from DCM solution generated disordered Compound I Form A (FIG. 7, second spectrum from bottom) after the sample was secondary dried at ambient temperature under vacuum for 3 days, which provides further evidence that amorphous Compound I is not physically stable.

One lyophilization experiment targeting amorphous Compound I was performed from a diluted solution in dioxane. A dilute solution of Compound I in dioxane was prepared and flash frozen by filtering it through a 0.2-μm nylon filter into a clean glass flask in dropwise. The glass flask was pre-cooled to −78° C. in a dry ice/acetone bath. The sample was attached to a Labconco FreeZone 71040 Benchtop-Freeze Dryer and lyophilized for 6 days.

Figure 7:
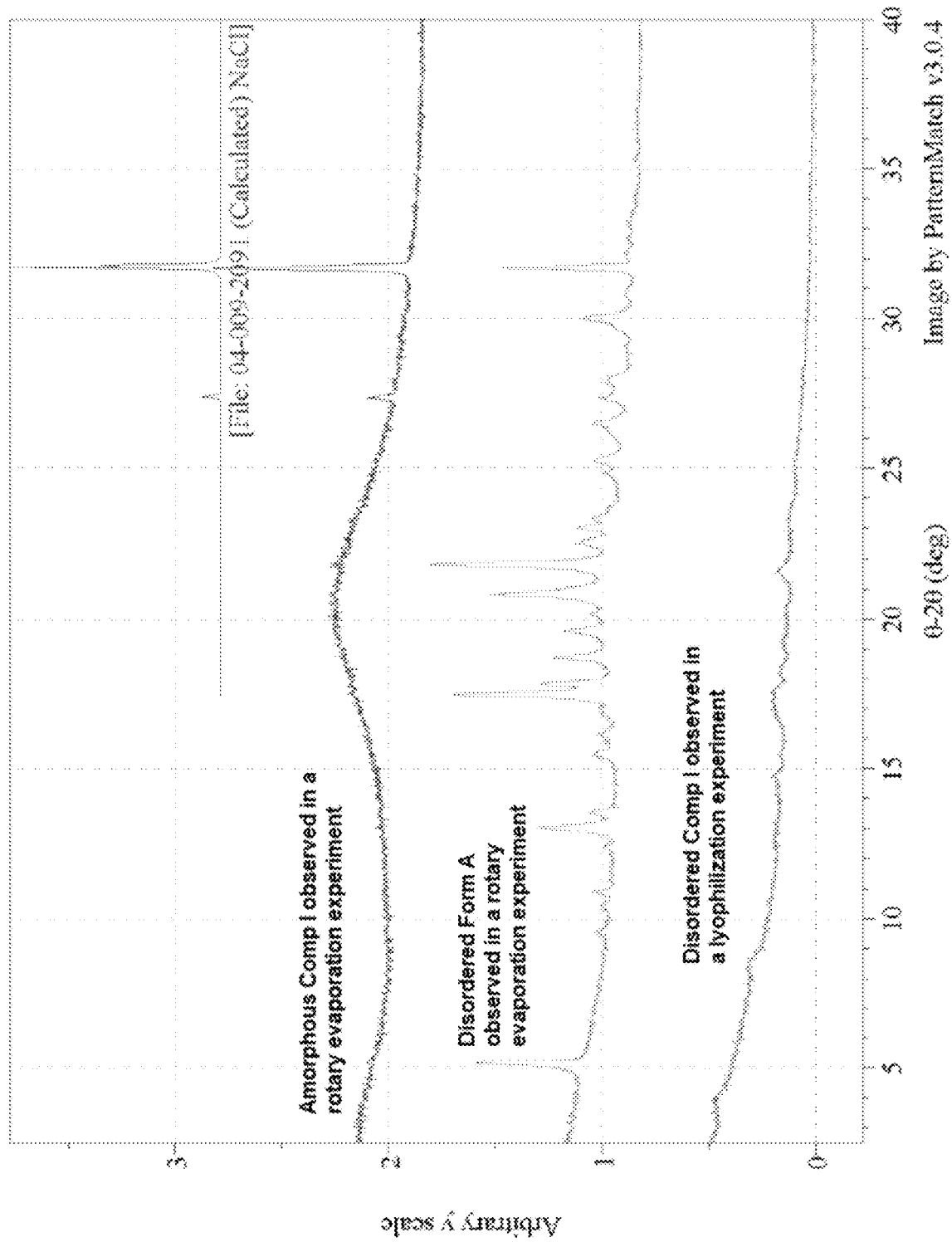
FIG. 7 shows XRPD spectrum overlay of NaCl, amorphous form of Compound I, disordered Form A of Compound I, and disordered form of Compound I.
Figure 10:
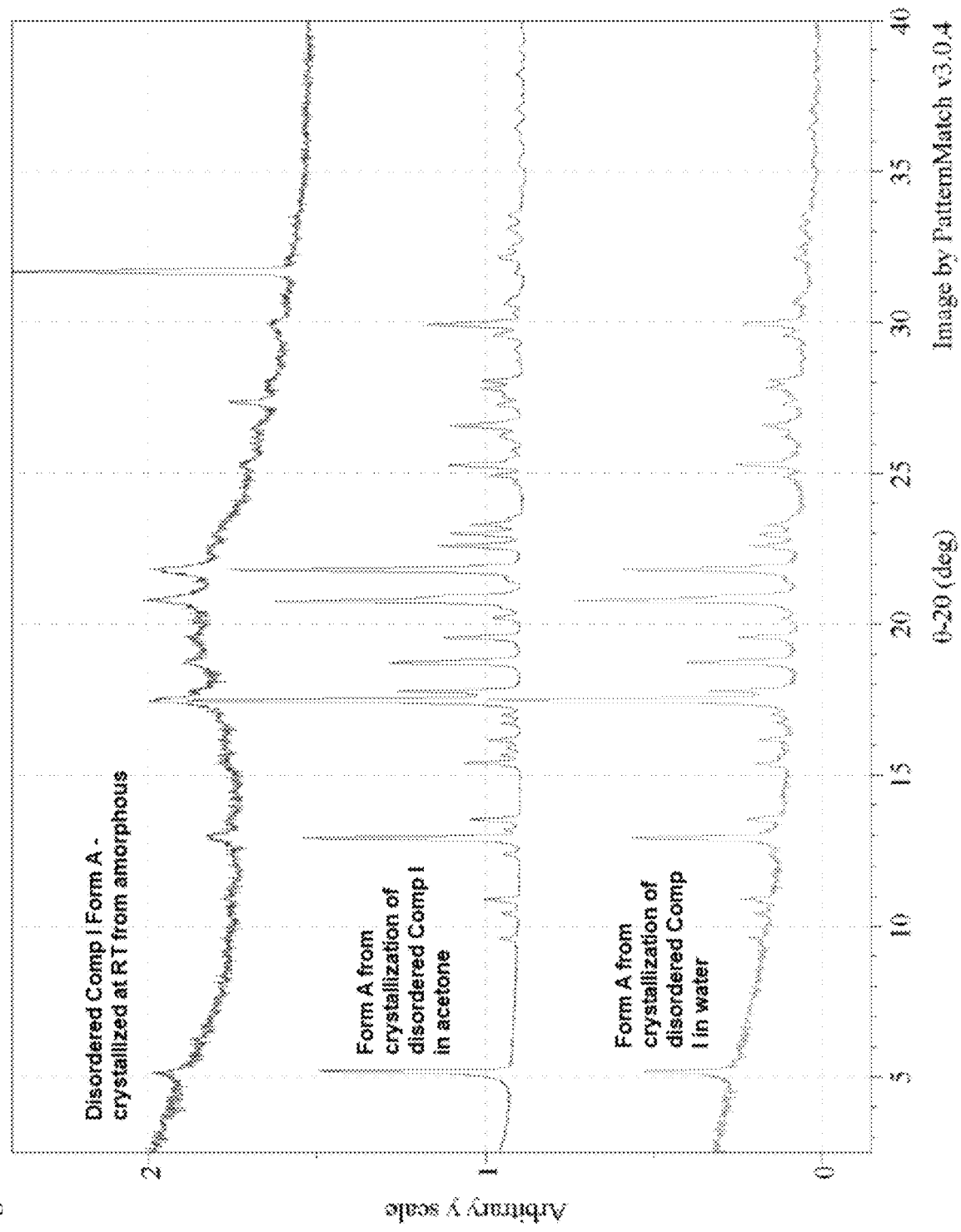
FIG. 10 shows XRPD spectrum overlay of disordered Form A and Form A obtained from crystallization experiments of amorphous and disordered Compound I.

The resulting solids were found to be disordered Compound I by XRPD (FIG. 7, bottom spectrum). Crystallization studies were performed on this disordered material (Table 10) and solids were stirred in acetone and H₂O for 4 days at ambient conditions. Both experiments generated crystalline Form A (FIG. 10, bottom two spectra).

Solubility: Generally, the solubility of an amorphous form is higher than that of the corresponding crystal form, due to the lack of crystalline lattice forces in the amorphous state. Solubility of the amorphous form of Compound I was studied by slow addition of the amorphous form from an organic stock solution into the pH 6.5 phosphate-buffered saline (PBS) solution or 0.5% wt simulated intestinal fluid (SIF) in pH 6.5 PBS. When the amorphous solubility is reached, a drug-rich phase forms which typically scatters light (e.g., liquid-liquid phase separation or LLPS), which can be detected by scattering of UV/Visible light and/or by dynamic light scattering (DLS).

Figure 16:
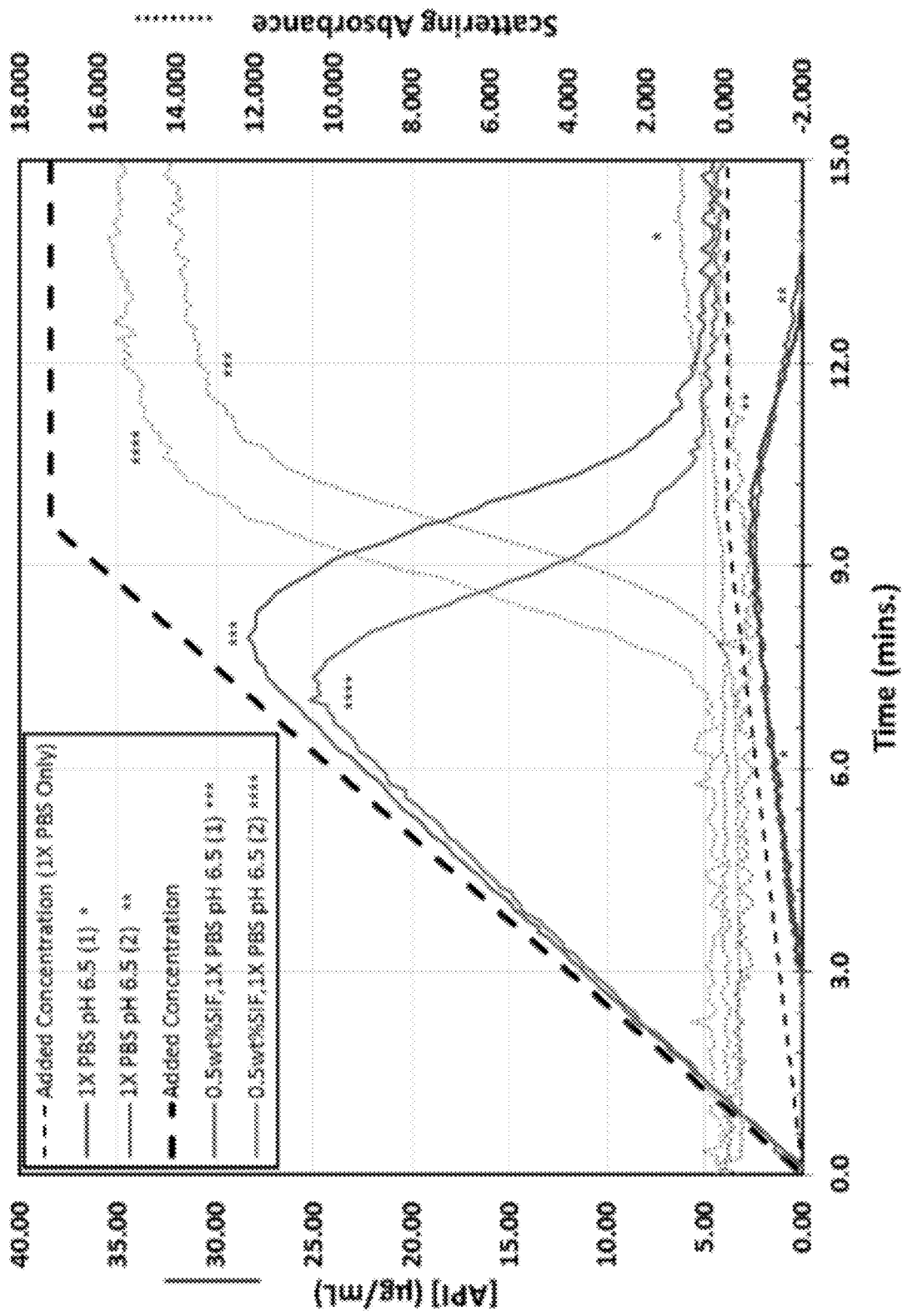
FIG. 16 shows solubility of amorphous form of Compound I.

No scattering event prior to crystallization was observed. Based on the data obtained, the amorphous solubility in pH 6.5 PBS and 0.5% SIF (pH 6.5) was >2.5 μg/mL and >25 μg/mL, respectively (FIG. 16). While an exact concentration could not be determined in this test, the amorphous solubility appears to be at least 20× higher than the crystalline solubility in simulated intestinal media. FIG. 16 shows concentration (solids lines) and scattering (dotted lines) vs.

time during addition of a 95:5 THF:Water solution of amorphous form of Compound I into blank PBS or 0.5% SIF in PBS.

Example 5. Single Crystal Structure Determination for Form a of Compound I

During the screen, single crystals of Form A were observed by slow evaporation from an acetone solution (Table 7). A suitable single crystal was therefore selected and analyzed by single-crystal X-ray diffractometry, and the structure of Form A was determined successfully.

The crystal system is monoclinic and the space group is $P2_1/c$. The cell parameters and calculated volume are: a=17.5550(2) Å, b=10.96169(13) Å, c=13.7961(2) Å, $\alpha$=90°, $\beta$=104.5717(15°), $\gamma$=90°, and V=2569.40(6) Å$^3$. In one embodiment, single crystals of Form A has a density of about 1.384 g/cm$^3$. The molecular weight is 535.43 g/mol with Z=4, resulting in a calculated density of 1.384 g/cm$^3$. Standard uncertainty is written in crystallographic parenthesis notation, e.g. 0.123(4) is equivalent to 0.123±0.004.

Figure 11:
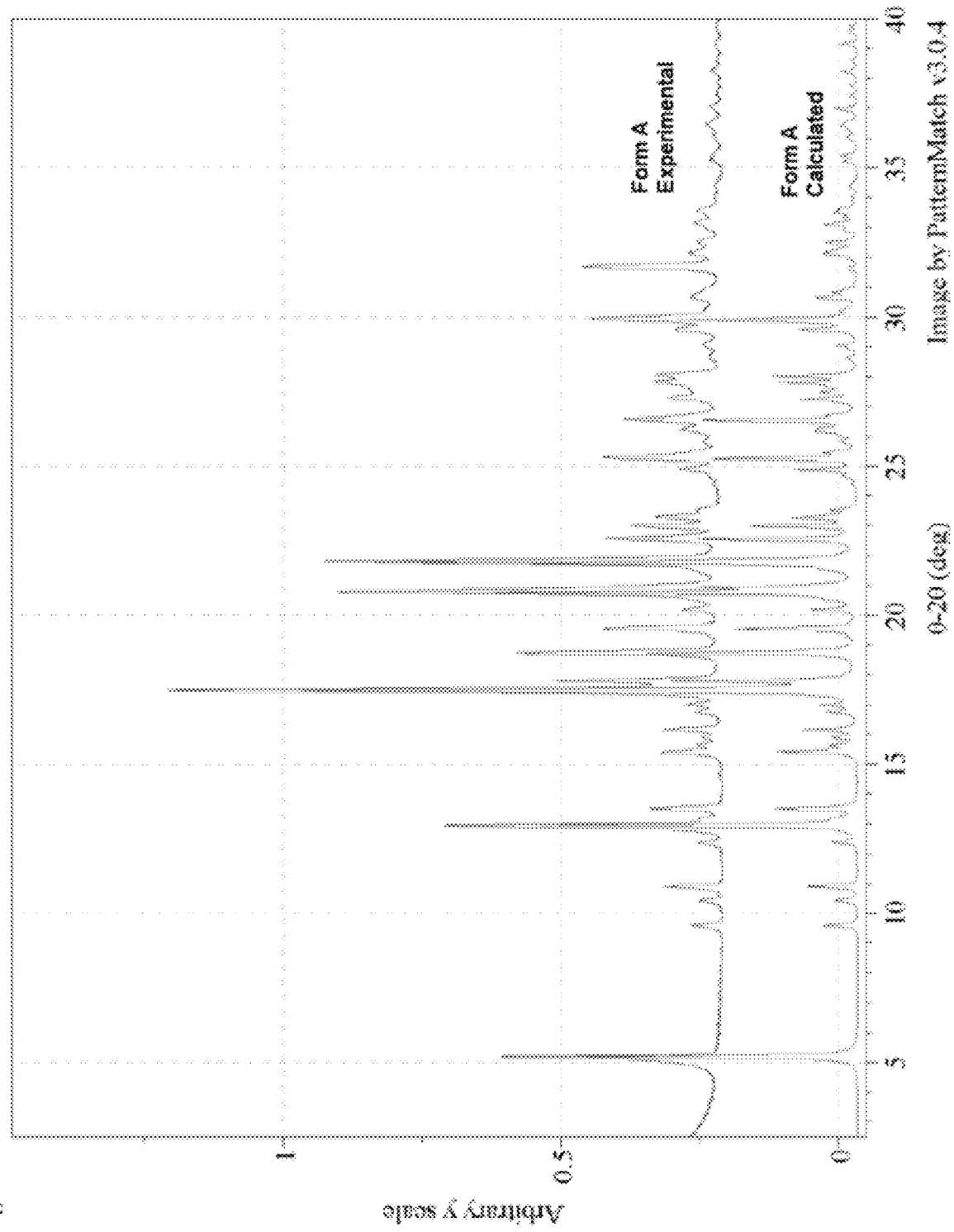
FIG. 11 shows XRPD spectrum overlay of Form A of Compound obtained experimentally and calculated pattern of Form A from single crystal data.

The quality of the structure obtained was high, as indicated by the fit residual, R, of 0.0559 (5.59%). R-factors in the range 2%-6% are quoted to be the most reliably determined structures (Glusker, Jenny Pickworth et al. *Crystal Structure Analysis: A Primer*, 2$^{nd}$ ed.; Oxford University press: New York, 1985; p. 87). The asymmetric unit was determined to contain one Compound I molecule. The cyano and chlorine moieties on the phenyl ring were found to be rotationally disordered by 180°, refining to 78% in the predominant orientation. The calculated XRPD pattern of Form A from the single crystal data is shown in FIG. 11, along with the experimental pattern acquired (see Example 1).

Example 6. Activity of Exemplary Compounds in Cellular Assays

LNCaP cells were transiently transfected with the PSA (6.1 kb)-luciferase reporter for 24 h, and then treated with indicated concentration of representative compounds with synthetic androgen, R1881 (1 nM) for 24 h. After 24 h of incubation with R1881, the cells were harvested, and relative luciferase activities were determined. To determine the IC$_{50}$, treatments were normalized to the maximum activity with androgen-induction (in the absence of test compounds, vehicle only) (Table 12).

Luciferase Assay: Lysates were thawed on ice then collected into V-bottom 96-well tissue culture plates. Lysates were centrifuged at 4° C. for 5 minutes at 4000 rpm. To measure luminescence of LNCaP cell lysates the Firefly Luciferase Assay System (Promega) was employed, according to manufacturer's protocol.

Statistical analyses were performed using GraphPad Prism (Version 6.01 for Windows; La Jolla, Calif., USA). Comparisons between treatment and control groups were compared using Two-Way ANOVA with post-hoc Dunnett's and Tukey's tests. Differences were considered statistically significant at P values less than 0.05. Densitometric quantification of relative AR levels was determined by Image.

Reference Compound X and EPI-002 have the following structures:

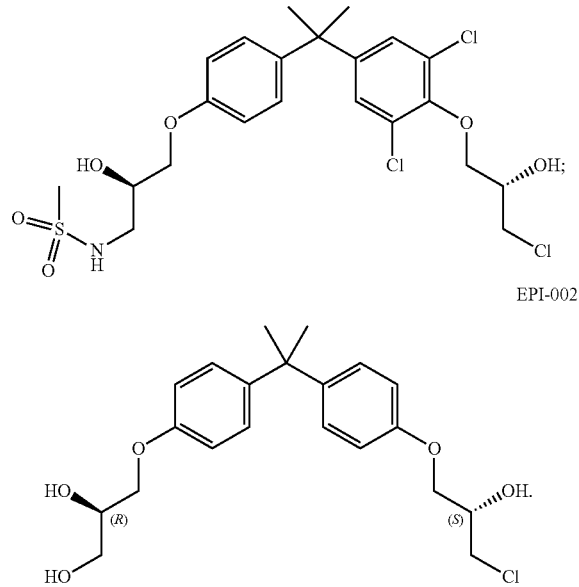

The PSA-Luc % inhibition IC$_{50}$ values Compound I is shown in Table 12.

TABLE 12

IC$_{50}$ of Compound I on Androgen-Induced PSA-Luciferase Activity

| Compound ID | Androgen-induced PSA-luciferase IC$_{50}$ (nM) | n |
|---|---|---|
| X | 1054 | 3 |
| Compound I | 535 | 2 |
| EPI-002 | 9580 | 2 |
| Enzalutamide | 189 | 8 |
| Bicalutamide | 306 | 2 |

Cell Proliferation Assay: Cell proliferation/viability was measured in LNCaP and PC3 cells with Alamar blue, and proliferation was measured in LN-CaP95 cells with BrdU incorporation. In LNCaP cells, AR specific proliferation is calculated by measuring the difference between control cells treated with or without 0.1 nM R1881. See Table 13.

TABLE 13

IC$_{50}$ of Compound I on Cell Proliferation/Viability

| | Cellular Proliferation/Viability IC$_{50}$ (μM) | | |
|---|---|---|---|
| Compound ID | LNCaP | PC-3 | LNCaP95 |
| X | 3.00 | >10 | 4.00 |
| Compound I | 0.44 | >10 | 3.78 |
| EPI-002 | 9.00 | >10 | ~20 |
| Enzalutamide | 0.35 | >10 | >10 |

Figure 12:
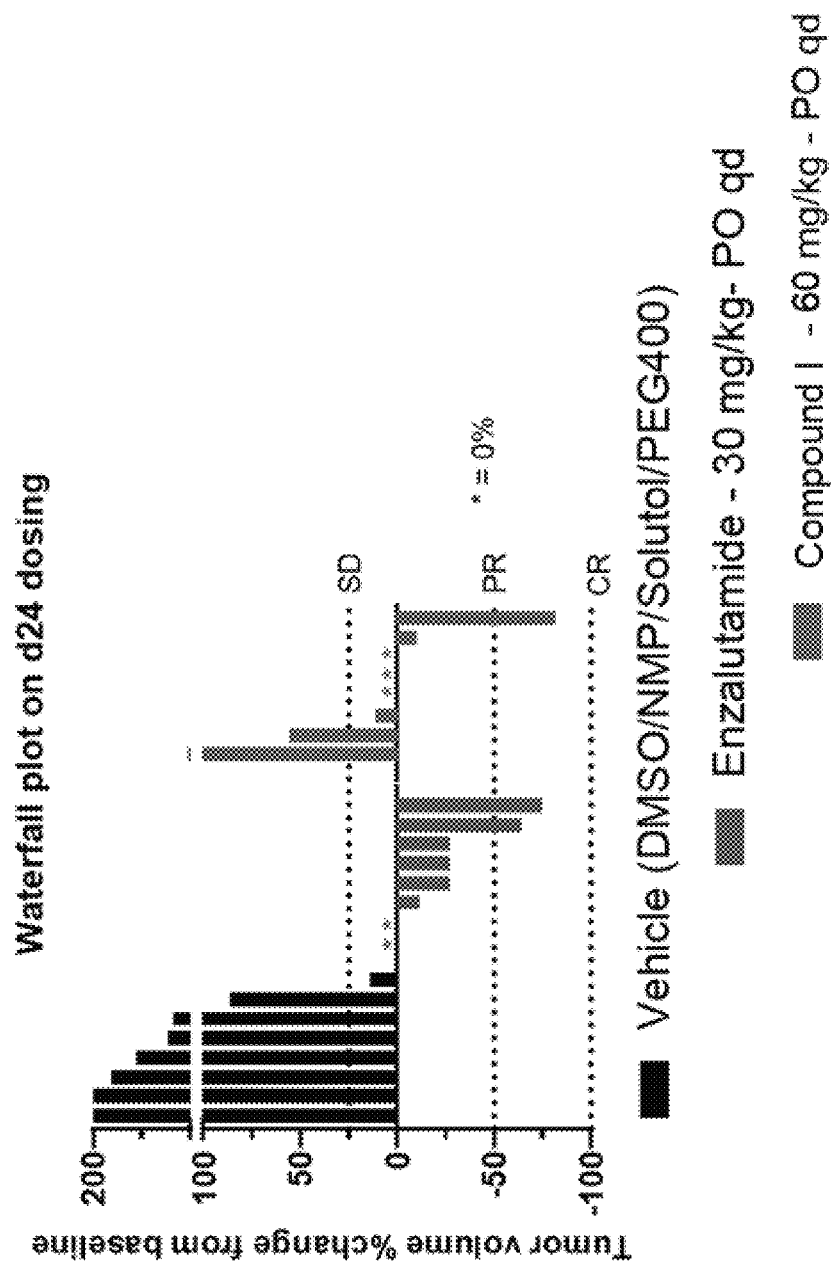
FIG. 12 shows individual tumor volume change from baseline measured at the end of experiment for oral administration of representative compounds to male NCG mice bearing LNCaP tumors

Example 7: In Vivo Activity of Representative Compounds in LNCaP Xenografts Model Tumor growth was measured in male NCG mice bearing LNCaP tumors. Castration was performed when tumors reached ~100 mm$^3$ and dosing (60 mg/kg PO qd) started 1 week after castration. Body weight of the mice were captured biweekly in the animals which showed no drug related toxicity. Individual tumor volume change from baseline measured at the end of the experiment. See FIG. 12. Data demonstrated that the representative compounds showed activity and induced partial regressions of tumor growth. The $C_{min}$ at 5 mg/kg PO and extrapolated $C_{min}$ in efficacy of the representative compounds are shown in Table 14.

TABLE 14

$C_{min}$ at 5 mg/kg PO and $C_{min}$ at 5 mg/kg PO

| Compound ID | Cmin at 5 mg/kg PO (μM) | Cmin at 5 mg/kg PO (μM) |
|---|---|---|
| Compound I | 0.68 | 8.18 |
| Enzalutamide | 3.80 | 22.8 |

Example 8: Solid Dispersion Composition Study 1

Compound I has very low crystalline solubility and very high amorphous solubility enhancement. It crystallizes rapidly from supersaturated aqueous solutions, dosed alone or with pre-dissolved precipitation-inhibiting polymers. Amorphous form of Compound I has a moderate glass transition temperature (Tg=62° C.) and partially re-crystallizes during heating of the amorphous form (Class 2 glass former).

Based on these characteristics, compositions were prepared at 10% active loading with 5 different polymers or polymer blends (Table 15). All manufactured formulations were amorphous by x-ray powder diffraction (XRPD).

TABLE 15

Compositions

| SDD No. | Compositions | Yield (%) | Potency (mgA/g) |
|---|---|---|---|
| A | 10/90 Compound I/HPMCAS-H | 93 | 104 ± 0.1 |
| B | 10/80/10 Compound I/HPMCAS-H/Soluplus | 96 | 107 ± 0.1 |
| C | 10/90 Compound I/HPMCAS-L | 94 | 102 ± 0.3 |
| D | 10/90 Compound I/PVP K30 | 91 | 106 ± 0.3 |
| E | 10/90 Compound I/Eudragit L100 | 95 | 102 ± 0.1 | mgA/g = milligrams of Compound I per gram of SDD composition

Five spray dried dispersion (SDD) compositions were successfully manufactured with high yields on a Bend Lab Dryer with 35 kg/hr drying capacity (BLD-35). All SDDs were sprayed at the same atomization pressure (120 psig). After spray drying, the SDDs were secondary dried in a heating vacuum tray dryer for about 24 hours to remove residual solvent. Manufacturing parameters are listed in Table 16.

TABLE 16

SDD composition manufacturing summary

| | |
|---|---|
| Batch size (g) | 3 |
| Solvent (w/w) | 9/1 DCM/methanol |
| Solids Content (wt %) | 4 |
| Atomizer | Schlick 2.0 |
| Drying Gas Flow Rate (g/min) | 500 |
| Solution Flow-rate (g/min) | ~35 |
| Atomization Pressure (psig) | 120 |
| Inlet Temperature (° C.) | 71 (for SDD-A); 77 (for SDD-B to SDD-E) |
| Outlet Temperature (° C.) | 35 |

All SDDs contained amorphous form of Compound I by X-ray diffraction analysis (FIG. 13). The Tg of each SDD was dominated by the type of polymer as determined by modulated differential scanning calorimetry (mDSC). A water or solvent loss peak is observed for each SDD, being most intense for SDD composition D (FIG. 14). The solid lines of the mDSC thermograms of FIG. 14 are the reverse heat flow and the dashed lines are the non-reversing heat flow. Summary of the mDSC data is listed in Table 17.

TABLE 17

Tabulated mDSC data for SDD compositions

| SDD No. | Tg (° C.) | ΔCp (J/(g° C.)) |
|---|---|---|
| A | 99 ± 0.5 | 0.33 ± 0.02 |
| B | 97 ± 0.6 | 0.33 ± 0.03 |
| C | 98 ± 0.2 | 0.34 ± 0.02 |
| D | 145 ± 0.03 | 0.29 ± 0.01 |
| E | 176 ± 2.0 | 0.41 ± 0.10 |

Example 9: Solid Dispersion Composition Study 2

SDD compositions G-M of Compound I were successfully manufactured with high yields on a Bend Lab Dryer with 35 kg/hr drying gas capacity (BLD-35) (Table 18). All SDDs were sprayed at the same atomization pressure (120 psig). After spray drying, the SDDs were secondary dried in a heating vacuum tray dryer at 40° C. for about 23 hours to remove residual solvent. Manufacturing parameters are listed in Table 19.

Secondary Drying was monitored by headspace gas chromatography in a separate tray drying space for an SDD composition of Table 18. Prior to secondary drying (wet sample), residual solvent in the SDD composition of Table 18 at storage temperature of 5° C. and 30° C. in sealed, stainless steel containers. Some solvent loss during storage and/or sampling was observed. SDD dried quickly during secondary drying, falling below ICH limits for residual DCM (600 ppm limit and permitted daily exposure of 6.0 mg/day) in less than 2 hours. Data supports secondary drying step of about 6 hours.

All manufactured formulations (stored at 2-8° C. after manufacturing) were amorphous by x-ray powder diffraction (XRPD), exhibiting the expected amorphous halo with no evidence of crystalline Compound I after manufacturing.

TABLE 18

SDD Compositions

| SDD No. | Compositions | Yield (%) | Potency (mgA/g) |
|---|---|---|---|
| A[1] | 10/90 Compound I/HPMCAS-H | 93 | 104 ± 0.1 |
| G | 15/85 Compound I/HPMCAS-H | 95 | 157 |
| H | 20/80 Compound I/HPMCAS-H | 94 | 209 |
| I | 25/75 Compound I/HPMCAS-H | 96 | 261 |
| J | 30/70 Compound I/HPMCAS-H | 93 | 314 |
| K | 60/40 Compound I/Eudragit L100 | 91 | 616 |
| L | 20/70/10 Compound I/PVP-VA64/Soluplus | 91 | 215 |
| M | 20/80 Compound I/Soluplus | 101 | 210 |

[1]From Example 8. mgA/g = milligrams of Compound I per gram of SDD composition

TABLE 19

| SDD composition manufacturing summary | |
|---|---|
| Batch size (g) | 5-10 g |
| Solvent (w/w) | 9/1 DCM/methanol |
| Solids Content (wt %) | 4 |
| Atomizer | Schlick 2.0 |
| Drying Gas Flow Rate (g/min) | 500 |
| Solution Flow-rate (g/min) | ~35 |
| Atomization Pressure (psig) | 120 |
| Inlet Temperature (° C.) | 90 (SDD-G); 85 (SDD-H and SDD-I); 84 (SDD-J); 76 (SDD-K); 75 (SDD-L and SDD-M) |
| Outlet Temperature (° C.) | 35 |

Tg of selected SDD compositions were determined by modulated differential scanning calorimetry (mDSC). The dry Tg (Tg determined under dry conditions) decreased with increased loading of Compound I. The dry Tg of all the SDD compositions showed sufficiently high for storage under dry conditions Table 20. The Tg decreased at elevated RH due to plasticization by absorbed water. SDD compositions I and K absorbed about 3% water at 75% RH while SDD composition M absorbed about 6% water, which is consistent with the decrease in Tg at 75% RH observed for SDD composition M.

TABLE 20

Tabulated mDSC data for SDD compositions

| SDD No. | Dry Tg (° C.) | 75% RH Tg (° C.) | Water at 75% RH (wt %) |
|---|---|---|---|
| A | 101.2 | — | — |
| G | 91.6 | — | — |
| H | 89 | — | — |
| I | 79.4 | 60.3 | 3 |
| K | 67.5 | 58.4 | 3 |
| M | 69.8 | 28.9 | 6 |

Example 10: Solid Dispersion Composition Study 3

SDD compositions H-J and N-R of Compound I were successfully manufactured with high yields on a Bend Lab Dryer with 35 kg/hr drying gas capacity (BLD-35) (Table 21). All SDDs were sprayed at the same atomization pressure (120 psig). After spray drying, the SDDs were secondary dried in a heating vacuum tray dryer at 40° C. with 3 liters per minute or 2.5 liters per minute of $N_2$ sweep gas for about 18.5-23 hours to remove residual solvent. Manufacturing parameters are listed in Table 22.

TABLE 21

SDD Compositions

| SDD No. | Compositions | Yield (%) | Potency (mgA/g) | Residual MeOH (wt %) | Residual DCM (wt %) |
|---|---|---|---|---|---|
| H | 20/80 Compound I/HPMCAS-H | 82 | 210 | ND | ND |
| I | 25/75 Compound I/HPMCAS-H | 85 | 260 | ND | ND |
| J | 30/70 Compound I/HPMCAS-H | 96 | 310 | ND | ND |
| N | 35/65 Compound I/HPMCAS-H | 95 | 360 | ND | ND |
| O | 40/60 Compound I/HPMCAS-H | 96 | 410 | ND | 0.01 |
| P | 45/55 Compound I/HPMCAS-H | 93 | 450 | <LOQ | 0.03 |
| Q | 50/50 Compound I/HPMCAS-H | 93 | 500 | <LOQ | 0.06 |
| R | 75/25 Compound I/HPMCAS-H | 93 | 750 | <LOQ | 0.09 | mgA/g = milligrams of Compound I per gram of SDD composition; LOQ = limit of quantification

TABLE 22

| SDD composition manufacturing summary | |
|---|---|
| Batch size (g) | 1-15 g |
| Solvent (w/w) | 9/1 DCM/methanol |
| Solids Content (wt %) | 4 |
| Atomizer | Schlick 2.0 |
| Drying Gas Flow Rate (g/min) | 500 |
| Solution Feed Rate (g/min) | 30-44 |
| Atomization Pressure (psig) | 120 |
| Inlet Temperature (° C.) | 92 (SDD-H and SDD-N); 100 (SDD-I); 97 (SDD-J); 89 (SDD-0); 85 (SDD-P, SDD-Q, and SDD-R) |
| Outlet Temperature (° C.) | 40-42 |

All manufactured formulations (stored at 2-8° C. after manufacturing) were amorphous by x-ray powder diffraction (XRPD), exhibiting the expected amorphous halo with no evidence of crystalline Compound I after manufacturing (FIG. 15).

The patents and publications listed herein describe the general skill in the art and are hereby incorporated by reference in their entireties for all purposes and to the same extent as if each was specifically and individually indicated to be incorporated by reference. In the case of any conflict between a cited reference and this specification, the specification shall control. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments may be modified or varied, without departing from the invention, as appreciated by those skilled in the art in light of the above teachings. It is therefore to be understood that, within the scope of the claims and their equivalents, the invention may be practiced otherwise than as specifically described.

What is claimed:

1. A method for treating prostate cancer in a subject in need thereof, comprising administering a therapeutically effective amount of an amorphous form of Compound I:

(Compound I)

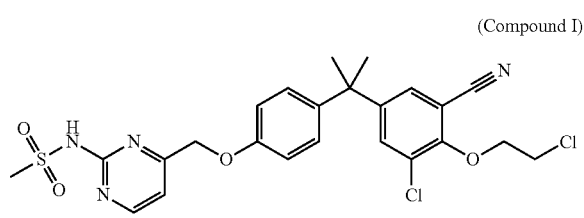 [SMILES: CC(C)(c1ccc(OCc2ccnc(NS(C)(=O)=O)n2)cc1)c1cc(Cl)c(OCCCl)c(C#N)c1]

or a pharmaceutically acceptable salt, solvate, or solvate salt thereof.

2. The method of claim 1, wherein the amorphous form of Compound I is anhydrous or non-solvated.

3. The method of claim 1, wherein the amorphous form of Compound I is not present as a pharmaceutically acceptable salt.

4. The method of claim 1, wherein the amorphous form of Compound I exhibits an XRPD pattern substantially similar to FIG. 7 (third spectrum from bottom), provided that peaks at 27.3±0.2 and 31.7±0.2 degrees two-theta are excluded.

5. The method of claim 1, wherein the amorphous form of Compound I exhibits a differential scanning calorimetry (DSC) thermogram comprising an exotherm peak at about 91° C.

6. The method of claim 1, wherein the amorphous form of Compound I exhibits a differential scanning calorimetry (DSC) thermogram comprising an endotherm peak which onset at about 178° C.

7. The method of claim 1, wherein the amorphous form of Compound I exhibits a glass transition temperature at about 61° C.

8. The method of claim 1, wherein the amorphous form of Compound I exhibits a thermogravimetric analysis (TGA) thermogram comprising a change in slope which onset at about 280° C.

9. The method of claim 1, wherein the amorphous form of Compound I has a purity of about 95% or higher.

10. The method of claim 1, wherein the amorphous form of Compound I has a purity of about 99% or higher.

11. The method of claim 1, wherein the amorphous form of Compound I exhibits an X-ray powder diffraction (XRPD) pattern substantially similar to any one of the patterns shown in FIGS. 13 and 15.

12. The method of claim 11, wherein the amorphous form of Compound I exhibits an XRPD pattern substantially similar to a pattern labeled as SDD-A, SDD-B, SDD-C, SDD-D, or SDD-E in FIG. 13 or a pattern labeled as SDD-H, SDD-I, SDD-J, SDD-N, SDD-O, SDD-O, SDD-P, SDD-Q, or SDD-R in FIG. 15.

13. The method of claim 11, wherein the amorphous form of Compound I exhibits a glass transition temperature (Tg) in the range of about 60° C. to about 180° C. as measured by differential scanning calorimeter.

14. The method of claim 11, wherein the amorphous form of Compound I exhibits a glass transition temperature (Tg) in the range of about 60° C. to about 90° C. as measured by differential scanning calorimeter.

15. The method of claim 11, wherein the amorphous form of Compound I has a purity in the range of about 80% to about 99%.

16. The method of claim 11, wherein the amorphous form of Compound I has a purity of about 95% or higher.

17. The method of claim 11, wherein the amorphous form of Compound I comprises less than 10% of crystalline form of Compound I or a pharmaceutically acceptable salt, solvate, stereoisomer or prodrug thereof.

18. The method of claim 11, wherein the amorphous form of Compound I comprises less than 5% of crystalline form of Compound I or a pharmaceutically acceptable salt, solvate, stereoisomer or prodrug thereof.

19. The method of claim 1, further comprising administering one or more additional therapeutic agents to the subject.

20. The method of claim 19, wherein the one or more additional therapeutic agents is an androgen receptor ligand-binding domain inhibitor or an inhibitor of CYP17.

21. The method of claim 19, wherein the one or more additional therapeutic agents comprises enzalutamide, apalutamide, darolutamide, bicalutamide, nilutamide, flutamide, ODM-204, TAS3681, galeterone, abiraterone, or abiraterone acetate.

22. The method of claim 1, wherein the prostate cancer is primary prostate cancer, localized prostate cancer, locally advanced prostate cancer, recurrent prostate cancer, advanced prostate cancer, metastatic prostate cancer, non-metastatic castration-resistant prostate cancer, metastatic castration-resistant prostate cancer, or hormone-sensitive prostate cancer.

23. The method of claim 1, wherein the prostate cancer is metastatic castration-resistant prostate cancer.

24. The method of claim 1, wherein the prostate cancer expresses full-length androgen receptor or truncated androgen receptor splice variant.

25. The method of claim 21, wherein the additional therapeutic agent comprises enzalutamide.

26. The method of claim 21, wherein the additional therapeutic agent comprises apalutamide.

27. The method of claim 21, wherein the additional therapeutic agent comprises darolutamide.

28. The method of claim 21, wherein the additional therapeutic agent comprises abiraterone.

29. The method of claim 21, wherein the additional therapeutic agent comprises abiraterone acetate.

30. The method of claim 21, wherein the additional therapeutic agent comprises bicalutamide.

\* \* \* \* \*